United States Patent
Ou et al.

(10) Patent No.: US 11,468,557 B2
(45) Date of Patent: Oct. 11, 2022

(54) FREE ORIENTATION FOURIER CAMERA

(71) Applicant: California Institute of Technology, Pasadena, CA (US)

(72) Inventors: Xiaoze Ou, Pasadena, CA (US); Changhuei Yang, Alhambra, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/658,019

(22) Filed: Mar. 13, 2015

(65) Prior Publication Data
US 2015/0264250 A1    Sep. 17, 2015

Related U.S. Application Data

(60) Provisional application No. 61/952,318, filed on Mar. 13, 2014.

(51) Int. Cl.
*G06T 7/00* (2017.01)
*G02B 27/46* (2006.01)
*A61B 5/00* (2006.01)

(52) U.S. Cl.
CPC ............ *G06T 7/0012* (2013.01); *G02B 27/46* (2013.01); *A61B 5/0059* (2013.01); *A61B 5/444* (2013.01)

(58) Field of Classification Search
CPC ................ G01B 9/02091; G01B 9/02044; A61B 3/102; A61B 5/0066; G01J 3/2823;
(Continued)

(56) References Cited

U.S. PATENT DOCUMENTS 4,873,653 A    10/1989  Grosskopf
4,917,494 A     4/1990  Poole et al.
(Continued)

FOREIGN PATENT DOCUMENTS

CN    1688254 A    10/2005
CN    1932565 A     3/2007
(Continued)

OTHER PUBLICATIONS

U.S. Appl. No. 14/960,252, filed Dec. 4, 2015 entitled "Multiplexed Fourier Ptychography Imaging Systems and Methods".
(Continued)

*Primary Examiner* — Farhan Mahmud
(74) *Attorney, Agent, or Firm* — Sheila Martinez-Lemke; Weaver Austin Villeneuve & Sampson LLP

(57) ABSTRACT

Certain aspects pertain to Fourier camera systems and methods. In one aspect, a Fourier camera comprises a first optical system, a second optical system, a variable aperture filter, and a light detector. The first optical system configured to receive illumination reflected from a curved sample surface. The variable aperture filter configured to move an aperture to a plurality of aperture locations in a Fourier plane, wherein the aperture filters light from the first optical system to the second optical system. The light detector configured to receive light from the second optical system, and configured to acquire a plurality of raw intensity images of the curved sample surface corresponding to the plurality of aperture locations, wherein the raw images are iteratively updated in overlapping regions in Fourier space to generate a focused, substantially uniform resolution image of the curved sample surface, and wherein the overlapping regions correspond to the plurality of aperture locations.

30 Claims, 13 Drawing Sheets

(58) Field of Classification Search
CPC ...... G01J 3/02; G01J 3/0208; G01N 21/4795;
G01N 21/6458; G02B 27/46; G02B
21/06; G02B 21/367; G02B 21/365;
G03H 1/0443; H04N 5/2254
See application file for complete search history.

(56) References Cited

U.S. PATENT DOCUMENTS

| | | |
|---|---|---|
| 5,475,527 A | 12/1995 | Hackel et al. |
| 6,144,365 A | 11/2000 | Young et al. |
| 6,154,196 A | 11/2000 | Fleck et al. |
| 6,320,174 B1 | 11/2001 | Tafas et al. |
| 6,320,648 B1 | 11/2001 | Brueck et al. |
| 6,747,781 B2 | 6/2004 | Trisnadi |
| 6,759,949 B2 | 7/2004 | Miyahara |
| 6,905,838 B1 | 6/2005 | Bittner |
| 7,436,503 B1 | 10/2008 | Chen et al. |
| 7,460,248 B2 | 12/2008 | Kurtz et al. |
| 7,706,419 B2 | 4/2010 | Wang et al. |
| 7,738,095 B2 | 6/2010 | Gardner, Jr. et al. |
| 7,787,588 B1 | 8/2010 | Yun et al. |
| 8,271,251 B2 | 9/2012 | Schwartz et al. |
| 8,313,031 B2 | 11/2012 | Vinogradov |
| 8,497,934 B2 | 7/2013 | Milnes et al. |
| 8,624,968 B1 | 1/2014 | Hersee et al. |
| 8,654,201 B2 | 2/2014 | Lim et al. |
| 8,942,449 B2 | 1/2015 | Maiden |
| 9,029,745 B2 | 5/2015 | Maiden |
| 9,343,494 B2 | 5/2016 | Lee et al. |
| 9,426,455 B2 | 8/2016 | Horstmeyer et al. |
| 9,497,379 B2 | 11/2016 | Ou et al. |
| 9,829,695 B2 | 11/2017 | Kim et al. |
| 9,864,184 B2 | 1/2018 | Ou et al. |
| 9,892,812 B2 | 2/2018 | Zheng et al. |
| 9,983,397 B2 | 5/2018 | Horstmeyer et al. |
| 9,993,149 B2 | 6/2018 | Chung et al. |
| 9,998,658 B2 | 6/2018 | Ou et al. |
| 10,162,161 B2 | 12/2018 | Horstmeyer et al. |
| 10,168,525 B2 | 1/2019 | Kim et al. |
| 10,222,605 B2 | 3/2019 | Kim et al. |
| 10,228,550 B2 | 3/2019 | Ou et al. |
| 10,401,609 B2 | 9/2019 | Ou et al. |
| 10,419,665 B2 | 9/2019 | Ou et al. |
| 10,568,507 B2 | 2/2020 | Chung et al. |
| 10,606,055 B2 | 3/2020 | Horstmeyer et al. |
| 10,652,444 B2 | 5/2020 | Horstmeyer et al. |
| 10,665,001 B2 | 5/2020 | Horstmeyer et al. |
| 10,679,763 B2 | 6/2020 | Zheng et al. |
| 10,684,458 B2 | 6/2020 | Chung et al. |
| 10,718,934 B2 | 7/2020 | Horstmeyer et al. |
| 10,732,396 B2 | 8/2020 | Kim et al. |
| 10,754,138 B2 | 8/2020 | Kim et al. |
| 10,754,140 B2 | 8/2020 | Chan et al. |
| 11,092,795 B2 | 8/2021 | Chung et al. |
| 2001/0055062 A1 | 12/2001 | Shioda et al. |
| 2002/0141051 A1 | 10/2002 | Vogt et al. |
| 2003/0116436 A1 | 6/2003 | Amirkhanian et al. |
| 2003/0118223 A1 | 6/2003 | Rahn et al. |
| 2004/0057094 A1 | 3/2004 | Olszak et al. |
| 2004/0146196 A1 | 7/2004 | Van Heel |
| 2004/0190762 A1 | 9/2004 | Dowski, Jr. et al. |
| 2005/0211912 A1 | 9/2005 | Fox |
| 2006/0098293 A1 | 5/2006 | Garoutte et al. |
| 2006/0158754 A1 | 7/2006 | Tsukagoshi et al. |
| 2006/0173313 A1 | 8/2006 | Liu et al. |
| 2006/0291707 A1 | 12/2006 | Kothapalli et al. |
| 2007/0057184 A1 | 3/2007 | Uto et al. |
| 2007/0133113 A1 | 6/2007 | Minabe et al. |
| 2007/0159639 A1 | 7/2007 | Teramura et al. |
| 2007/0171430 A1 | 7/2007 | Tearney et al. |
| 2007/0189436 A1 | 8/2007 | Goto et al. |
| 2007/0206200 A1* | 9/2007 | Lindner ............ G01B 11/2441 356/511 |
| 2007/0269826 A1 | 11/2007 | Geddes |
| 2008/0101664 A1* | 5/2008 | Perez ................ G06K 9/00033 382/125 |
| 2008/0182336 A1 | 7/2008 | Zhuang et al. |
| 2008/0192343 A1 | 8/2008 | Miyawaki et al. |
| 2008/0205833 A1 | 8/2008 | Fu et al. |
| 2009/0008580 A1* | 1/2009 | Luberek ............. G03F 7/70191 250/559.1 |
| 2009/0046164 A1 | 2/2009 | Shroff et al. |
| 2009/0079987 A1 | 3/2009 | Ben-Ezra et al. |
| 2009/0125242 A1 | 5/2009 | Choi et al. |
| 2009/0284831 A1 | 11/2009 | Schuster et al. |
| 2009/0316141 A1 | 12/2009 | Feldkhun |
| 2010/0135547 A1 | 6/2010 | Lee et al. |
| 2010/0271705 A1 | 10/2010 | Hung |
| 2011/0075928 A1 | 3/2011 | Jeong et al. |
| 2011/0181869 A1 | 7/2011 | Yamaguchi et al. |
| 2011/0192976 A1 | 8/2011 | Own et al. |
| 2011/0235863 A1 | 9/2011 | Maiden |
| 2011/0255163 A1 | 10/2011 | Merrill et al. |
| 2012/0069344 A1 | 3/2012 | Liu |
| 2012/0099803 A1 | 4/2012 | Ozcan et al. |
| 2012/0105618 A1 | 5/2012 | Brueck et al. |
| 2012/0118967 A1 | 5/2012 | Gerst |
| 2012/0157160 A1 | 6/2012 | Ozcan et al. |
| 2012/0176673 A1 | 7/2012 | Cooper |
| 2012/0182541 A1 | 7/2012 | Canham |
| 2012/0218379 A1 | 8/2012 | Ozcan et al. |
| 2012/0248292 A1 | 10/2012 | Ozcan et al. |
| 2012/0250032 A1* | 10/2012 | Wilde ................ G01B 9/02047 356/521 |
| 2012/0281929 A1 | 11/2012 | Brand et al. |
| 2013/0057748 A1 | 3/2013 | Duparre et al. |
| 2013/0083886 A1 | 4/2013 | Carmi et al. |
| 2013/0093871 A1 | 4/2013 | Nowatzyk et al. |
| 2013/0094077 A1 | 4/2013 | Brueck et al. |
| 2013/0100525 A1 | 4/2013 | Chiang et al. |
| 2013/0170767 A1 | 7/2013 | Choudhury et al. |
| 2013/0182096 A1 | 7/2013 | Boccara et al. |
| 2013/0223685 A1 | 8/2013 | Maiden |
| 2014/0007307 A1 | 1/2014 | Routh, Jr. et al. |
| 2014/0029824 A1 | 1/2014 | Shi et al. |
| 2014/0043616 A1 | 2/2014 | Maiden et al. |
| 2014/0050382 A1 | 2/2014 | Adie et al. |
| 2014/0085629 A1 | 3/2014 | Bodkin et al. |
| 2014/0118529 A1 | 5/2014 | Zheng et al. |
| 2014/0126691 A1 | 5/2014 | Zheng et al. |
| 2014/0133702 A1 | 5/2014 | Zheng et al. |
| 2014/0139840 A1 | 5/2014 | Judkewitz et al. |
| 2014/0152801 A1 | 6/2014 | Fine et al. |
| 2014/0153692 A1 | 6/2014 | Larkin et al. |
| 2014/0160236 A1 | 6/2014 | Ozcan et al. |
| 2014/0160488 A1 | 6/2014 | Zhou |
| 2014/0217268 A1 | 8/2014 | Schleipen et al. |
| 2014/0267674 A1 | 9/2014 | Mertz et al. |
| 2014/0347672 A1 | 11/2014 | Pavilion et al. |
| 2014/0368812 A1 | 12/2014 | Humphry et al. |
| 2015/0003714 A1 | 1/2015 | McCarty et al. |
| 2015/0036038 A1 | 2/2015 | Horstmeyer et al. |
| 2015/0044098 A1 | 2/2015 | Smart et al. |
| 2015/0054979 A1 | 2/2015 | Ou et al. |
| 2015/0160450 A1 | 6/2015 | Ou et al. |
| 2015/0286042 A1 | 10/2015 | Hilbert et al. |
| 2015/0331228 A1 | 11/2015 | Horstmeyer et al. |
| 2016/0088205 A1 | 3/2016 | Horstmeyer et al. |
| 2016/0110584 A1 | 4/2016 | Remiszewski et al. |
| 2016/0156880 A1 | 6/2016 | Teich et al. |
| 2016/0178883 A1 | 6/2016 | Horstmeyer et al. |
| 2016/0202460 A1 | 7/2016 | Zheng |
| 2016/0210763 A1 | 7/2016 | Horstmeyer et al. |
| 2016/0216208 A1 | 7/2016 | Kim et al. |
| 2016/0216503 A1 | 7/2016 | Kim et al. |
| 2016/0266366 A1 | 9/2016 | Chung et al. |
| 2016/0320595 A1 | 11/2016 | Horstmeyer et al. |
| 2016/0320605 A1 | 11/2016 | Ou et al. |
| 2016/0341945 A1 | 11/2016 | Ou et al. |
| 2017/0061599 A1 | 3/2017 | Remiszewski et al. |
| 2017/0146788 A1 | 5/2017 | Waller et al. |
| 2017/0178317 A1 | 6/2017 | Besley et al. |
| 2017/0188853 A1 | 7/2017 | Nakao et al. |

(56) References Cited

U.S. PATENT DOCUMENTS

| | | |
|---|---|---|
| 2017/0273551 A1 | 9/2017 | Chung et al. |
| 2017/0299854 A1 | 10/2017 | Kim et al. |
| 2017/0354329 A1 | 12/2017 | Chung et al. |
| 2017/0363853 A1 | 12/2017 | Besley |
| 2017/0371141 A1 | 12/2017 | Besley |
| 2018/0045569 A1 | 2/2018 | Nath et al. |
| 2018/0048811 A1 | 2/2018 | Waller et al. |
| 2018/0078447 A1 | 3/2018 | Viner et al. |
| 2018/0078448 A9 | 3/2018 | Shockley, Jr. et al. |
| 2018/0088309 A1 | 3/2018 | Ou et al. |
| 2018/0120553 A1 | 5/2018 | Leshem et al. |
| 2018/0231761 A1 | 8/2018 | Dai et al. |
| 2018/0307017 A1 | 10/2018 | Horstmeyer et al. |
| 2018/0316855 A1 | 11/2018 | Ou et al. |
| 2018/0329194 A1 | 11/2018 | Small et al. |
| 2018/0348500 A1 | 12/2018 | Naaman, III et al. |
| 2018/0373016 A1 | 12/2018 | Leshem et al. |
| 2019/0049712 A1 | 2/2019 | Kim et al. |
| 2019/0056578 A1 | 2/2019 | Horstmeyer et al. |
| 2019/0077610 A1 | 3/2019 | Flammann |
| 2019/0097523 A1 | 3/2019 | Schaefer |
| 2019/0097524 A1 | 3/2019 | Lin |
| 2019/0137753 A1 | 5/2019 | Chan et al. |
| 2019/0317311 A1 | 10/2019 | Kim et al. |
| 2019/0331902 A1 | 10/2019 | Ou et al. |
| 2019/0391382 A1 | 12/2019 | Chung et al. |
| 2020/0186705 A1 | 6/2020 | Ou et al. |
| 2021/0082595 A1 | 3/2021 | Zheng et al. |

FOREIGN PATENT DOCUMENTS

| | | |
|---|---|---|
| CN | 1311392 C | 4/2007 |
| CN | 101372179 A | 2/2009 |
| CN | 101408623 A | 4/2009 |
| CN | 101680848 A | 3/2010 |
| CN | 101726366 A | 6/2010 |
| CN | 101743519 A | 6/2010 |
| CN | 101868740 A | 10/2010 |
| CN | 101872033 A | 10/2010 |
| CN | 101957183 A | 1/2011 |
| CN | 102292662 A | 12/2011 |
| CN | 102608597 A | 7/2012 |
| CN | 102629371 A | 8/2012 |
| CN | 102652680 A | 9/2012 |
| CN | 102753935 A | 10/2012 |
| CN | 103096804 A | 5/2013 |
| CN | 103154662 A | 6/2013 |
| CN | 103201648 A | 7/2013 |
| CN | 103377746 A | 10/2013 |
| CN | 103842799 A | 6/2014 |
| CN | 104101993 A | 10/2014 |
| CN | 104181686 A | 12/2014 |
| CN | 104200449 A | 12/2014 |
| EP | 1 640 706 A1 | 3/2006 |
| EP | 0 760 109 B1 | 4/2007 |
| JP | 2007-299604 | 11/2007 |
| JP | 2008-147629 A | 6/2008 |
| JP | 2010-012222 A | 1/2010 |
| KR | 10-1998-0075050 | 11/1998 |
| TW | 201428339 A | 7/2014 |
| WO | WO 96/28751 A1 | 9/1996 |
| WO | WO9953469 | 10/1999 |
| WO | WO 2002/102128 A1 | 12/2002 |
| WO | WO 2003/062744 A1 | 7/2003 |
| WO | WO 2004/034121 A2 | 4/2004 |
| WO | WO 2008-116070 | 9/2008 |
| WO | WO 2011-093043 | 8/2011 |
| WO | WO 2012/037182 A1 | 3/2012 |
| WO | WO 2014/033459 A1 | 3/2014 |
| WO | WO 2014/070656 A1 | 5/2014 |
| WO | WO 2015/017730 A1 | 2/2015 |
| WO | WO 2015/027188 A1 | 2/2015 |
| WO | WO 2016/090331 A1 | 6/2016 |
| WO | WO 2016/106379 A1 | 6/2016 |
| WO | WO 2016/118761 A1 | 7/2016 |
| WO | WO 2016/123156 A1 | 8/2016 |
| WO | WO 2016/123157 A1 | 8/2016 |
| WO | WO 2016/149120 A1 | 9/2016 |
| WO | WO 2016/187591 A1 | 11/2016 |
| WO | WO 2017/066198 A1 | 4/2017 |
| WO | WO 2017081539 A1 | 5/2017 |
| WO | WO 2017081540 A1 | 5/2017 |
| WO | WO 2017081542 A2 | 5/2017 |

OTHER PUBLICATIONS

U.S. Appl. No. 14/979,154, filed Dec. 22, 2015 entitled "Epi-Illumination Fourier Ptychographic Imaging for Thick Samples".
Office Action dated Oct. 5, 2015 in U.S. Appl. No. 14/065,305.
Notice of Allowance dated Dec. 4, 2015 in U.S. Appl. No. 14/065,305.
International Search Report and Written Opinion dated Feb. 21, 2014 in PCT/US2013/067068.
International Preliminary Report on Patentability dated May 14, 2015 in PCT/US2013/067068.
International SearchReport and Written Opinion dated Dec. 5, 2014 in PCT/US2014/052351.
International SearchReport and Written Opinion dated Nov. 13, 2014 in PCT/US2014/049297. .
"About Molemap," [Downloaded from internet at http://molemap.net.au/about-US/], 2 pages.
"Doctor Mole—Skin Cancer App," [Downloaded from internet at http://www.doctormole.com], 1 page.
"Immersion Media," Olympus, Microscopy Resource Center, http://www.olympusmicro.com/primer/anatomy/immersion.html.
"Lytro," [Downloaded from internet at https://www.lytro.com/], 6 pages.
"Melafind," [Downloaded from internet at http://www.melafind.com/], 4 pages.
"TFOCS: Templates for First-Order Conic Solvers," CVX Research, CVX Forum, http://cvxr.com/tfocs/.
Maiden, A. et al., "A new method of high resolution, quantitative phase scanning microscopy," in: M.T. Postek, D.E. Newbury, S.F. Platek, D.C. Joy (Eds.), SPIE Proceedings of Scanning Microscopy, 7729, 2010.
Alexandrov, S. A. et al., "Synthetic Aperture Fourier holographic optical microscopy," Phys. Rev. Lett. 97, 168102 (2006).
Alexandrov, S.et al., "Spatial information transmission beyond a system's diffraction limit using optical spectral encoding of the spatial frequency," Journal of Optics A: Pure and Applied Optics 10, 025304 (2008).
Arimoto, H. et al. "Integral three-dimensional imaging with digital reconstruction," Opt. Lett. 26, 157-159 (2001).
Balan, R. et al., "Painless reconstruction from magnitudes of frame coefficients," J Fourier Anal Appl 15:488-501 (2009).
Bauschke, HH et al., "Phase retrieval, error reduction algorithm, and Fienup variants: a view from convex optimization," J Opt Soc Am A 19:1334-1345 (2002).
Becker, S. et al., "Templates for convex cone problems with applications to sparse signal recovery," Technical report, Department of Statistics, Stanford University, (2010), 48 Pages.
Betti, R., et al., "Observational study on the mitotic rate and other prognostic factors in cutaneous primary melanoma arising from naevi and from melanoma de novo," Journal of the European Academy of Dermatology and Venereology, 2014.
Bian, L. et al., "Fourier ptychographic reconstruction using Wirtinger flow optimization," Opt. Express 23:4856-4866 (2015).
Bian, Z. et al., "Adaptive system correction for robust Fourier ptychographic imaging," Optics express, 2013, 21(26): p. 32400-32410.
Blum, A. et al., "Clear differences in hand-held dermoscopes," JDDG: Journal der Deutschen Dermatologischen Gesellschaft, 2006, 4(12): p. 1054-1057.
Blum, A., et al., Dermatoskopie von Hauttumoren: Auflichtmikroskopie; Dermoskopie; digitale Bildanalyse; mit 28 Tabellen. 2003: Springer DE, Chapter 4 "Dermatoskopisch sichtbare Strukturen" p. 15-66.
Brady, D. et al., "Multiscale gigapixel photography," Nature 486, 386-389 (2012).

(56) References Cited

OTHER PUBLICATIONS

Burer S, Monteiro RDC (2003) A nonlinear programming algorithm for solving semidefinite programs via low-rank factorization. Math Program, Ser B 95:329-357.
Burer, S. et al., "Local minima and convergence in low-rank semidefinite programming. Math Program," Ser A 103:427-444 (2005).
Candes, EJ. et al., "Phase retrieval via matrix completion," SIAM J. Imaging Sci. 6:199-225 (2012).
Candes, EJ. et al., "PhaseLift: exact and stable signal recovery from magnitude measurements via convex programming.," Comm Pure Appl Math 66:1241-1274 (2013).
Candes, EJ. et al., "Soltanolkotabi M Phase retrieval via Wirtinger flow: theory and algorithms," IEEE Trans. Info. Theory 61:1985-2007 (2015).
Chen, T. et al., "Polarization and phase shifting for 3D scanning of translucent objects," Proc. CVPR, (2007).
Chin, L. et al., "Malignant melanoma: genetics and therapeutics in the genomic era," Genes & development, 2006, 20(16): p. 2149-2182.
Colomb, T. et al., "Automatic procedure for aberration compensation in digital holographic microscopy and applications to specimen shape compensation," Appl. Opt. 45, 851-863 (2006).
De Sa, C. et al., "Global convergence of stochastic gradient descent for some non convex matrix problems," Proc. 32nd Int. Conf. Machine Learning (2015).
Denis, L. et al., "Inline hologram reconstruction with sparsity constraints," Opt. Lett. 34, pp. 3475-3477 (2009).
Di, J. et al., "High resolution digital holographic microscopy with a wide field of view based on a synthetic aperture technique and use of linear CCD scanning," Appl. Opt. 47, pp. 5654-5659 (2008).
Dierolf, M. et al., "Ptychographic coherent diffractive imaging of weakly scattering specimens," New J. Phys. 12, 035017 (2010).
Dong, S. et al., "Aperture-scanning Fourier ptychography for 3D refocusing and super-resolution macroscopic imaging," p. 13586-13599 (Jun. 2, 2014).
Eldar, Y.C. et al., "Sparse phase retrieval from short-time Fourier measurements," IEEE Signal Processing Letters 22, No. 5 (2015): 638-642.
Emile, O. et al., "Rotating polarization imaging in turbid media," Optics Letters 21(20), (1996).
Faulkner, H. et al., "Movable aperture lensless transmission microscopy: a novel phase retrieval algorithm," Phys. Rev. Lett. 93, 023903 (2004).
Faulkner, H. M. L. et al., "Error tolerance of an iterative phase retrieval algorithm for moveable illumination microscopy," Ultramicroscopy 103(2), 153-164 (2005).
Fazel, M. (2002) Matrix rank minimization with applications. PhD thesis (Stanford University, Palo Alto, CA).
Feng, P. et al., "Long-working-distance synthetic aperture Fresnel off-axis digital holography," Optics Express 17, pp. 5473-5480 (2009).
Fienup, J. R., "Invariant error metrics for image reconstruction," Appl. Opt. 3 6(3 2), 8352-8357 (1997).
Fienup, J. R., "Lensless coherent imaging by phase retrieval with an illumination pattern constraint," Opt. Express 14, 498-508 (2006).
Fienup, J. R., "Phase retrieval algorithms: a comparison," Appl. Opt. 21, 2758-2769 (1982).
Fienup, J. R., "Reconstruction of a complex-valued object from the modulus of its Fourier transform using a support constraint," J. Opt. Soc. Am. A 4, 118-123 (1987).
Fienup, J. R., "Reconstruction of an object from the modulus of its Fourier transform," Opt. Lett. 3, 27-29 (1978).
Gan, X. et al., "Image enhancement through turbid media under a microscope by use of polarization gating methods," JOSA A 16(9), (1999).
Ghosh, A. et al., "Multiview face capture using polarized spherical gradient illumination," ACM Transactions on Graphics 30(6) (2011).
Goodman, J., "Introduction to Fourier Optics," Roberts & Company Publication, Third Edition, chapters 1-6, pp. 1-172 (2005).
Goodson, A.G., et al., "Comparative analysis of total body and dermatoscopic photographic monitoring of nevi in similar patient populations at risk for cutaneous melanoma," Dermatologic Surgery, 2010, 36(7): p. 1087-1098.
Granero, L. et al., "Synthetic aperture superresolved microscopy in digital lensless Fourier holography by time and angular multiplexing of the object information," Appl. Opt. 49, pp. 845-857 (2010).
Grant, M. et al., "CVX: Matlab software for disciplined convex programming," version 2.0 beta, http://cvxr.com/cvx, (Sep. 2013), 3 pages.
Greenbaum, A. et al., "Increased space-bandwidth product in pixel super-resolved lensfree on-chip microscopy," Sci. Rep. 3, p. 1717 (2013).
Guizar-Sicairos, M., "Phase retrieval with transverse translation diversity: a nonlinear optimization approach," Opt. Express 16, 7264-7278 (2008).
Gunturk, B. K. et al., "Image Restoration: Fundamentals and Advances," vol. 7, Chapter 3, pp. 63-68 (CRC Press, 2012).
Gustafsson, M. G., "Surpassing the lateral resolution limit by a factor of two using structured illumination microscopy," J. Microsc. 198, 82-87 (2000).
Gutzler, T. et al., "Coherent aperture-synthesis, wide-field, high-resolution holographic microscopy of biological tissue," Opt. Lett. 35, pp. 1136-1138 (2010).
Hillman, T. R. et al., "High-resolution, wide-field object reconstruction with synthetic aperture Fourier holographic optical microscopy," Opt. Express 17, pp. 7873-7892 (2009).
Hong, S-H. et al., "Three-dimensional volumetric object reconstruction using computational integral imaging," Opt. Express 12, 483-491 (2004).
Hoppe, W., "Diffraction in inhomogeneous primary wave fields. 1. Principle of phase determination from electron diffraction interference," Acta Crystallogr. A25, 495-501 1969.
Horstmeyer, R. et al., "A phase space model of Fourier ptychographic microscopy," Optics Express, 2014. 22(1): p. 338-358.
Horstmeyer, R. et al., "Overlapped fourier coding for optical aberration removal," Manuscript in preparation, 19 pages (2014).
Hüe, F. et al., "Wave-front phase retrieval in transmission electron microscopy via ptychography," Phys. Rev. B 82, 121415 (2010).
Humphry, M. et al., "Ptychographic electron microscopy using high-angle dark-field scattering for sub-nanometre resolution imaging," Nat. Commun. 3, 730 (2012).
Rodenburg, J., "Ptychography and related diffractive imaging methods," Adv. Imaging Electron Phys.150, 87-184 (2008).
Jaganathan, K. et al., "Phase retrieval with masks using convex optimization," IEEE International Symposium on Information Theory Proceedings (2015): 1655-1659.
Jaganathan, K. et al., "Recovery of sparse 1-D signals from the magnitudes of their Fourier transform," IEEE International Symposium on Information Theory Proceedings (2012): 1473-1477. Do Not Have Copy.
Jaganathan, K. et al., "STFT Phase retrieval: uniqueness guarantees and recovery algorithms," arXiv preprint arXiv: 1508.02820 (2015).
Sun, J. et al., "Coded multi-angular illumination for Fourier ptychography based on Hadamard codes," 5 pages (2015).
Kim, M. et al., "High-speed synthetic aperture microscopy for live cell imaging," Opt. Lett. 36, pp. 148-150 (2011).
Kittler, H., et al., Morphologic changes of pigmented skin lesions: a useful extension of the ABCD rule for dermatoscopy. Journal of the American Academy of Dermatology, 1999. 40(4): p. 558-562.
Levoy, M. et al., "Light field microscopy," ACM Trans. Graphics 25, (2006).
Levoy, M. et al., "Recording and controlling the 4D light field in a microscope using microlens arrays," J. Microsc. 235 (2009).
Li X. et al., "Sparse signal recovery from quadratic measurements via convex programming," SIAM Journal on Mathematical Analysis 45, No. 5 (2013): 3019-3033.
Lohmann, A. W., Dorsch, R. G., Mendlovic, D., Zalevsky, Z. & Ferreira, C., "Space-bandwidth product of optical signals and systems," J. Opt. Soc. Am. A 13, pp. 470-473 (1996).
Lue, N. et al., "Live Cell Refractometry Using Hilbert Phase Microscopy and Confocal Reflectance Microscopy," The Journal of Physical Chemistry A, 113, p. 13327-13330 (2009).

(56) References Cited

OTHER PUBLICATIONS

Maiden et al., "Superresolution imaging via ptychography," Journal of the Optical Society of America A, Apr. 2011, vol. 28 No. 4, pp. 604-612.
Maiden, A. et al., "An improved ptychographical phase retrieval algorithm for diffractive imaging," Ultramicroscopy 109(10), 1256-1262 (2009).
Maiden, A. M. et al., "Optical ptychography: a practical implementation with useful resolution," Opt. Lett. 35, 2585-2587 (2010).
Marchesini S., "A unified evaluation of iterative projection algorithms for phase retrieval," Rev Sci Instrum 78:011301 (2007).
Marchesini S. et al., "Augmented projections for ptychographic imaging," Inverse Probl 29:115009 (2013).
Marrison, J. et al., "Ptychography—a label free, high-contrast imaging technique for live cells using quantitative phase information," Sci. Rep. 3, 2369 (2013).
Miao et al., "High Resolution 3D X-Ray Diffraction Microscopy," Physical Review Letters, Aug. 19, 2002, vol. 89, No. 8, pp. 1-4.
Mico, V. et al., "Synthetic aperture microscopy using off-axis illumination and polarization coding," Optics Communications, pp. 276, 209-217 (2007).
Mico, V. et al., "Synthetic aperture superresolution with multiple off-axis holograms," JOSA A 23, pp. 3162-3170 (2006).
Mir, M. et al., "Blood screening using diffraction phase cytometry," Journal of Biomedical Optics 15, pp. 027016-027014 (2010).
Mir, M. et al., "Optical measurement of cycle-dependent cell growth," Proceedings of the National Academy of Sciences 108, p. 13124-13129 (2011).
Nayar, S. K. et al., "Fast separation of direct and global components of a scene using high frequency illumination," ACM Transactions on Graphics 25(3) (2006).
Ng, R., et al., "Light field photography with a hand-held plenoptic camera", Computer Science Technical Report CSTR, 2005, 2(11).
Nomura, H. et al., "Techniques for measuring aberrations in lenses used in photolithography with printed patterns," Appl. Opt. 38(13), 2800-2807 (1999).
Ohlsson, H. et al., "Compressive phase retrieval from squared output measurements via semidefinite programming," arXiv:1111.6323 (2011).
Ou, X. et al., "High numerical aperture Fourier ptychography: principle, implementation and characterization," Opt. Express 23:3472-3491 (2015).
Ou, X., et al., "Quantitative phase imaging via Fourier ptychographic microscopy," Optics Letters, 2013, 38(22): p. 4845-4848.
Ou et al., "Embedded pupil function recovery for Fourier ptychographic microscopy," Optics Express 22 (5), pp. 4960-4972 (2014).
Balan, R. et al., "On signal reconstruction without phase, Apphed and Computational Harmonic Analysis 20," No. 3 (2006): 345-356.
Recht, B. et al., "Guaranteed minimum-rank solutions of linear matrix equations via nuclear norm minimization," SIAM Review 52, No. 3 (2010): 471-501.
Reinhard, E. et al., "High Dynamic Range Imaging: Acquisition, Display, and Image-based Lighting" (Morgan Kaufmann, 2010).
Rodenburg, J. M. et al., "A phase retrieval algorithm for shifting illumination," Appl. Phys. Lett. 85, 4795-4797 (2004).
Rodenburg, J. M. et al., "Hard-X-ray lensless imaging of extended objects," Phys. Rev. Lett. 98, 034801 (2007).
Rodenburg, J. M. et al., "The theory of super-resolution electron microscopy via Wigner-distribution deconvolution," Phil, Trans. R. Soc. Lond. A 339, 521-553 (1992).
Schnars, U. et al., "Digital recording and numerical reconstruction of holograms," Measurement Science and Technology, 13, R85 (2002).
Schwarz, C. J. et al., "Imaging interferometric microscopy," Optics letters 28, pp. 1424-1426 (2003).
Shechner, Y.Y.et al., "Polarization-based vision through haze," Apphed Optics 42(3), (2003).
Shechtman, Y. et al., "Sparsity based sub-wavelength imaging with partially incoherent hght via quadratic compressed sensing," Opt Express 19:14807-14822 (2011).

Siegel, R. et al.,, "Cancer statistics 2013," CA: a cancer journal for clinicians, 2013. 63(1): p. 11-30.
Stoecker, W.V., R.K. Rader, and A. Halpern, Diagnostic Inaccuracy of Smartphone Applications for Melanoma Detection: Representative Lesion Sets and the Role for Adjunctive Technologies. JAMA Dermatology, 2013. 149(7): p. 884.
Sun, D. L. et al., "Estimating a signal from a magnitude spectrogram via convex optimization," arXiv:1209.2076 (2012).
Thibault, P. et al., "Probe retrieval in ptychographic coherent diffractive imaging," Ultramicroscopy 109(4), 338-343 (2009).
Thibault, P. et al., "High-resolution scanning X-ray diffraction microscopy," Science 321, 379-382 (2008).
Thomas, L., et al., Semiological value of ABCDE criteria in the diagnosis of cutaneous pigmented tumors. Dermatology, 1998, 197(1): p. 11-17.
Tippie, A.E. et al., "High-resolution synthetic-aperture digital holography with digital phase and pupil correction," Opt. Express 19, p. 12027-12038 (2011).
Turpin, T. et al., "Theory of the synthetic aperture microscope," pp. 230-240 (1995).
Tyson, R., "Principles of Adaptive Optics" (CRC Press, 2010).
Mahajan, V. N., "Zernike circle polynomials and optical aberrations of systems with circular pupils," Appl. Opt. 33(34), 8121-8124 (1994).
Waldspurger, I. et al., "Phase recovery, maxcut and complex semidefinite programming," Mathematical Programming 149, No. 1-2 (2015): 47-81.
Wang, Z. et al., "Tissue refractive index as marker of disease," Journal of Biomedical Optics 16, 116017-116017 (2011).
Watanabe, M. et al., "Telecentric optics for focus analysis," IEEE trans. pattern. anal. mach. intell., 19 1360-1365 (1997).
Wesner J. et al., "Reconstructing the pupil function of microscope objectives from the intensity PSF," in Current Developments in Lens Design and Optical Engineering III, R. E. Fischer, W. J. Smith, and R. B. Johnson, eds., Proc. SPIE 4767, 32-43 (2002).
Wolf, J.A. et al., "Diagnostic Inaccuracy of Smartphone Apphcations for Melanoma Detection," JAMA Dermatology, 2013, 149(7): p. 885-885.
Wu, J. et al., "Focal plane tuning in wide-field-of-view microscope with Talbot pattern illumination," Opt. Lett. 36, 2179-2181 (2011).
Wu, J. et al., "Wide field-of-view microscope based on holographic focus grid illumination," Opt. Lett. 35, 2188-2190 (2010).
Xu, W. et al., "Digital in-line holography for biological apphcations," Proc. Natl Acad. Sci. USA 98, pp. 11301-11305 (2001).
Yuan, C. et al., "Angular multiplexing in pulsed digital holography for aperture synthesis," Optics Letters 33, pp. 2356-2358 (2008).
Zhang Y. et al., "Self-learning based fourier ptychographic microscopy," Optics Express, 16pgs (2015).
Zheng, G. et al., "Characterization of spatially varying aberrations for wide field-of-view microscopy," Opt. Express 21, 15131-15143 (2013).
Zheng, G. et al., "Microscopy refocusing and dark-field imaging by using a simple LED array," Opt. Lett. 36, 3987-3989 (2011).
Zheng, G. et al., "Sub-pixel resolving optofluidic microscope for on-chip cell imaging," Lab Chip 10, pp. 3125-3129 (2010).
Zheng, G. et al., "The ePetri dish, an on-chip cell imaging platform based on subpixel perspective sweeping microscopy (SPSM)," Proc. Natl Acad. Sci. USA 108, pp. 16889-16894 (2011).
Zheng, G. et al., "Wide-field, high-resolution Fourier ptychographic microscopy," Nature Photonics (2013).
Zheng, G.A. et al., "0.5 gigapixel microscopy using a flatbed scanner," Biomed. Opt. Express 5, 1-8 (2014).
Tian, L. et al., "Multiplexed Coded Illumination for Fourier Ptychography with an LED Array Microscope," Optical Society of America, 14 pages (2014).
Schechner, Y., "Multiplexing for Optimal Lighting," IEEE Transactions on Pattern Analysis and Machine Intelligence, vol. 29, No. 8, 1339-1354 (2007).
Ma, W. et al., "Rapid Acquisition of Specular and Diffuse Normal Maps from Polarized Spherical Gradient Illumination," University of Southern California, Institute for Creative Technologies, 12 pages (2007).

(56) References Cited

OTHER PUBLICATIONS

Rowe, M.P. et al., "Polarization-difference imaging: a biologically inspired technique for observation through scattering media," Optics Letters, vol. 20, No. 6, 3 pages (1995).
Gruev, V. et al., "Dual-tier thin film polymer polarization imaging sensor," Optics Express, vol. 18, No. 18, 12 pages (2010).
Preliminary Amendment dated Mar. 17, 2014 filed in U.S. Appl. No. 14/065,280.
Preliminary Amendment dated Apr. 25, 2016 filed in U.S. Appl. No. 14/710,947.
Preliminary Amendment dated Nov. 28, 2016 filed in U.S. Appl. No. 15/206,859.
Preliminary Amendment dated Mar. 17, 2014 filed in U.S. Appl. No. 14/065,305.
Preliminary Amendment dated Nov. 28, 2016 filed in U.S. Appl. No. 15/209,604.
U.S. Notice of Allowance dated Jan. 14, 2016 in U.S. Appl. No. 14/448,850.
U.S. Notice of Allowance dated Jan. 22, 2016 in U.S. Appl. No. 14/466,481.
U.S. Notice of Allowance dated Apr. 13, 2016 in U.S. Appl. No. 14/448,850.
U.S. Notice of Allowance dated Apr. 22, 2016 in U.S. Appl. No. 14/466,481.
U.S. Office Action dated Jul. 14, 2016 in U.S. Appl. No. 15/007,196.
U.S. Notice of Allowance dated Aug. 23, 2016 in U.S. Appl. No. 14/466,481.
U.S. Office Action dated Aug. 16, 2016 in U.S. Appl. No. 14/065,280.
U.S. Office Action dated Sep. 16, 2016 I U.S. Appl. No. 14/065,305.
U.S. Notice of Allowance dated Nov. 2, 2016 in U.S. Appl. No. 14,572,493.
U.S. Office Action dated Nov. 22, 2016 in U.S. Appl. No. 15/003,559.
U.S. Supplemental Notice of Allowance dated Dec. 12, 2016 in U.S. Appl. No. 14/572,493.
U.S. Notice of Allowance dated Jan. 13, 2017 in U.S. Appl. No. 14/065,305.
U.S. Final Office Action dated Jan. 23, 2017 in U.S. Appl. No. 15/007,196.
U.S. Office Action dated Feb. 21, 2017 in U.S. Appl. No. 14/960,252.
U.S. Supplemental Notice of Allowability dated Mar. 2, 2017 in U.S. Appl. No. 14/065,305.
U.S. Notice of Allowance dated Mar. 8, 2017 in U.S. Appl. No. 14/572,493.
U.S. Notice of Allowance dated Mar. 22, 2017 in U.S. Appl. No. 15/007,196.
U.S. Office Action dated Mar. 24, 2017 in U.S. Appl. No. 14/710,947.
U.S. Notice of Allowance dated Mar. 31, 2017 in U.S. Appl. No. 14/572,493.
U.S. Final Office Action dated Apr. 3, 2017 in U.S. Appl. No. 14/065,280.
U.S. Notice of Allowance dated Jun. 9, 2017 in U.S. Appl. No. 14/065,305.
U.S. Notice of Allowance dated Jun. 9, 2017 in U.S. Appl. No. 15/206,859.
U.S. Notice of Allowance dated Jun. 9, 2017 in U.S. Appl. No. 15/007,196.
U.S. Notice of Allowance dated Jun. 20, 2017 in U.S. Appl. No. 14/572,493.
U.S. Supplemental Notice of Allowance dated Jun. 28, 2017 in U.S. Appl. No. 15/206,859.
U.S. Final Office Action dated Jul. 27, 2017 in U.S. Appl. No. 15/003,559.
U.S. Notice of Allowance dated Aug. 16, 2017 in U.S. Appl. No. 15/209,604.
U.S. Notice of Allowance dated Sep. 1, 2017 in U.S. Appl. No. 15/206,859.
European Third-Party Observations, dated Jan. 20, 2016 in EP Application No. 13851670.3.
European Extended Search Report dated Mar. 31, 2016 in EP Application No. 13851670.3.
International Preliminary Report on Patentability dated Mar. 3, 2016 issued in PCT/US2014/052351.
International Preliminary Report on Patentability dated Feb. 11, 2016 issued in PCT/US2014/049297.
International Search Report and Written Opinion dated Feb. 22, 2016 issued in PCT/US2015/064126.
International Search Report and Written Opinion dated Apr. 19, 2016 issued in PCT/US2015/067498.
International Search Report and Written Opinion dated May 4, 2016 issued in PCT/US2016/015001.
International Search Report and Written Opinion dated May 11, 2016 issued in PCT/US2016/015002.
International Search Report and Written Opinion dated Jun. 27, 2016 issued in PCT/US2016/022116.
International Search Report and Written Opinion dated Jun. 30, 2016 issued in PCT/US2016/014343.
International Search Report and Wrtitten Opinion dated Sep. 5, 2016 issued in PCT/US2016/033638.
Chinese Office Action [Description in English] dated Jul. 11, 2016 issued in Application No. CN 201380068831.6.
Chinese Office Action [Description in English] dated Dec. 13, 2016 issued in Application No. CN201480057911.6.
Extended European Search Report dated Feb. 16, 2017 issued in Application No. 14837844.1.
Extended European Search Report dated Feb. 15, 2017 issued in Applicatoin No. 14832857.8.
Chinese Second Office Action [Description in English] dated Feb. 17, 2017 issued in Application No. CN201380068831.6.
International Preliminary Report on Patentability dated Jun. 15, 2017 issued in Application No. PCT/US2015/064126.
European Office Action dated May 16, 2017 issued in European Patent Application No. 13851670.3.
International Preliminary Report on Patentability dated Jul. 6, 2017 issued in Application No. PCT/US2015/067498.
International Preliminary Report on Patentability dated Aug. 3, 2017 issued in Application No. PCT/US2016/014343.
International Preliminary Report on Patentability dated Aug. 10, 2017 issued in Application No. PCT/US2016/015001.
International Preliminary Report on Patentability dated Aug. 10, 2017 issued in Application No. PCT/US2016/015002.
Abramowitz, M., et al., "Field Curvature," Olympus Microscopy Resource Center, 2012 Olympus America Inc., pp. 1-3. [retrieved on Feb. 24, 2016] <URL:http://www.olympusmicro.com/primer/anatomy/fieldcurvature.html>.
Age-Related Macular Degeneration (AMD) | National Eye Institute. 2010 Table, pp. 1-8. [retrieved Apr. 5, 2016] URL: https://www.nei.nih.gov/eyedata/amd™top>.
Bian, L., et al., "Fourier ptychographic reconstruction using Poisson maximum likelihood and truncated Wirtinger gradient," Nature Publishing Group; Scientific Reports, vol. 6, No. 27384, Jun. 10, 2016, pp. 1-10. <doi: 10.1038/srep27384>.
BioTek® Brochure: BioTek's Multi-Mode Microplate Reading Techonologies, BioTek Instruments, Inc. pp. 2. [retrieved on Mar. 14, 2016] URL: http://www.biotek.com>.
Bishara, W., et al., "Holographic pixel super-resolution in portable lensless on-chip microscopy using a fiber-optic array," NIH-PA, Lab Chip, *Author manuscript*; available in PMC Aug. 8, 2011, pp. 1-9. (Published in final edited form as: Lab Chip. Apr. 7, 2011; 11(7): 1276-1279. <doi:10.1039/c01c00684j>).
Bishara, W., et al., "Lensfree on-chip microscopy over a wide field-of-view using pixel super-resolution," Optics Express, vol. 18, No. 11, May 24, 2010, pp. 11181-11191. <doi: 10.1364/OE.18.011181>.
Born, M., et al., "Principles of Optics: Electromagnetic theory of propagation, interference and diffraction of light," Seventh (Expanded) Edition, Cambridge University Press, England 1999, pp. 1-31, [ISBN 0 521 642221 hardback].
Bunk, O., et al., "Influence of the overlap parameter on the convergence of the ptychographical iterative engine," Ultramicroscopy, vol. 108, (2008), pp. 481-487. <doi:10.1016/j.ultramic.2007.08.003>.
Carroll, J., "Adaptive Optics Retinal Imaging: Applications for Studying Retinal Degeneration," Archives of Ophthalmology, vol.

(56) References Cited

OTHER PUBLICATIONS

126, No. 6, Jun. 9, 2008, pp. 857-858, [retrieved Feb. 24, 2016] <doi:10.1001/archopht.126.6.857>.
Chai, A., et al., "Array imaging using intensity-only measurements," IOP Publishing: Inverse Problems, vol. 27, No. 1, Jan. 2011, pp. 1-16. <doi: 10.1088/0266-5611/27/1/015005>.
Chao, W. et al., "Soft X-ray microscopy at a spatial resolution better than 15 nm," Nature|Letters, vol. 435, Jun. 30, 2005, pp. 1210-1213, <doi:10.1038/nature03719>.
Choi, W., et al., "Tomographic phase microscopy," NPG: Nature Methods | Advance Online Publication, Aug. 12, 2007, pp. 1-3, <doi:10.1038/NMETH1078>.
Chung, J., et al., "Counting White Blood Cells from a Blood Smear Using Fourier Ptychographic Microscopy," PLoS One, vol. 10, No. 7, Jul. 17, 2015, pp. 1-10. <doi:10.1371/journal.pone.0133489>.
Chung, J., et al., "Wide field-of-view fluorescence image deconvolution with aberration-estimation from Fourier ptychography," Biomedical Optics Express, vol. 7, No. 2, Feb. 1, 2016, pp. 352-368. <doi: 10.1364/BOE.7.000352>.
Chung, J., et al., *pre-published manuscript of* "Wide-field Fourier ptychographic microscopy using laser illumination source," ArXiv e-prints (Submitted on Feb. 9, 2016 (vl), last revised Mar. 23, 2016 (this version, v2)). [retrieved on May 20, 2016] <URL:arXiv: 1602.02901lv2 [physics.optics] Mar. 23, 2016>.
Debailleul, M., et al., "High-resolution three-dimensional tomographic diffractive microscopy of transparent inorganic and biological samples," Optics Letters, Optical Society of America, vol. 34, No. 1, Jan. 1, 2009, pp. 79-81. <doi: 10.1364/OL.34.000079>.
Dierolf, M., et al., "Ptychographic X-ray computed tomography at the nanoscale," Nature|Letter, vol. 467, Sep. 23, 2010, pp. 436-439, <doi:10.1038/nature09419>.
Dong, S., et al., "FPscope: a field-portable high-resolution microscope using a cellphone lens," Biomedical Optics Express, vol. 5, No. 10, Oct. 1, 2014, pp. 3305-3310. <doi: 10.1364/BOE.5.003305>.
Dong, S., et al., "High-resolution fluorescence imaging via pattern-illuminated Fourier ptychography," Optics Express, vol. 22, No. 17, Aug. 25, 2014, pp. 20856-20870. <doi: 10.1364/OE.22.020856>.
Essen BioScience, "Real-time, quantitative live-cell analysis, IncuCyte© ZOOM System," IncuCyte Zoom System Brochure 2016, pp. 1-4. [retrieved Feb. 25, 2016] [URL: http://www.essenbioscience.com/Incuyte].
Gerke T.D., et al., "Aperiodic volume optics," Nature Photonics, vol. 4, Feb. 7, 2010, pp. 188-193. <doi:10.1038/nphoton.2009.290>.
Godara, P., et al., "Adaptive Optics Retinal Imaging: Emerging Clinical Applications," NIH-PA Author Manuscript; available in PMC Dec. 1, 2011. Published in final edited form as: Optom. Vis. Sci . . . Dec. 2010; 87(12): 930-941. <doi: 10.1097/OPX.0b013e3181ff9a8b>.
Greenbaum, A., et al., "Field-portable wide-field microscopy of dense samples using multi-height pixel super-resolution based lensfree imaging," Lab Chip, The Royal Society of Chemistry, vol. 12, No. 7, Jan. 31, 2012, pp. 1242-1245. [retrieved on Feb. 27, 2016] <URL:http://dx.doi.org/10.1039/C2LC21072J>.
Guo, K., et al., "Optimization of sampling pattern and the design of Fourier ptychographic illuminator," Optics Express, vol. 23, No. 5, Mar. 9, 2015, pp. 6171-6180. <doi: 10.1364/OE.23.006171>.
Gustafsson, M.G.L., "Surpassing the lateral resolution limit by a factor of two using structured illumination microscopy," Journal of Microscopy, vol. 198, Pt. 2, May 2000, pp. 82-87. <doi:10.1046/j.1365-2818.2000.00710.x>.
Haigh, S. J., et al., "Atomic structure imaging beyond conventional resolution limits in the transmission electron microscope," Physical Review Letters, vol. 103, Issue 12, Sep. 18, 2009, pp. 126101.1-126101.4. <doi:10.1103/PhysRevLett.103.126101>.
Han, C., et al., "Wide Field-of-View On-Chip Talbot Fluorescence Microscopy for Longitudinal Cell Culture Monitoring from within the Incubator" Analytical Chemistry, vol. 85, No. 4, Jan. 28, 2013, pp. 2356-2360. <doi:10.1021/ac303356v>.

Hofer, H., et al., "Dynamics of the eye's wave aberration," Journal of Optical Society of America A., vol. 18, No. 3, Mar. 2001, pp. 497-506. <doi: 10.13 64/JOSAA.18.000497>.
Hofer, H., et al., "Organization of the Human Trichromatic Cone Mosaic," The Journal of Neuroscience, vol. 25, No. 42, Oct. 19, 2005, pp. 9669-9679. <doi: 10.1523/JNEUROSCI.2414-05.2005>.
Hoppe, W., "Diffraction in inhomogeneous primary wave fields. 1. Principle of phase determination from electron diffraction interference." Acta Crystallographica Section a—Crystal Physics Diffraction lheoretical and General Crystallography, A25, Jan. 1, 1969, pp. 495-501. (English Machine Translation Incl.).
Horstmeyer, R., et al., "Diffraction tomography with Fourier ptychography," Optica, Optical Society of America, vol. 3, No. 8, Aug. 2016, pp. 827-835. <doi:10.1364/OPTICA.3.000827>.
Horstmeyer, R., et al., "Digital pathology with Fourier Ptychography," Computerized Medical Imaging and Graphics, vol. 42, Jun. 2015, pp. 38-43. <doi:10.1016/j.compmedimag.2014.11.005>.
Horstmeyer, R., et al., "Solving ptychography with a convex relaxation," New Journal of Physics, vol. 17, May 27, 2015, pp. 1-14. <doi: 10.1088/1367-2630/17/5/053044> [URL: http://iopscience.iop.org/1367-2630/17/5/053044].
Horstmeyer, R., et al., "Standardizing the resolution claims for coherent microscopy," Nature Photonics | Commentary, vol. 10, No. 2, Feb. 2016, pp. 68-71. <doi:10.1038/nphoton.2015.279> [URL: http://dx.doi.org/10.1038/nphoton.2015.279].
Joeres, S., et al., "Retinal Imaging With Adaptive Optics Scanning Laser Ophthalmoscopy in Unexplained Central Ring Scotoma," Arch. Ophthalmol., vol. 126, No. 4, Apr. 2008, pp. 543-547. [retrieved Jun. 10, 2015] [URL: http://archopht.jamanetwork.com/].
Jung, J.H., et al., *Author Manuscript of* "Microfluidic-integrated laser-controlled microactuators with on-chip microscopy imaging functionality," Published in final edited form as: Lab Chip, Oct. 7, 2014, vol. 14, No. 19, pp. 3781-3789. <doi: 10.1039/c41c00790e>.
Kawata, S. et al., "Optical microscope tomography. I. Support constraint," Journal Optical Society America A, vol. 4, No. 1, Jan. 1987, pp. 292-297. <doi:10.1364/JOSAA.4.000292>.
Kay, D. B., et al., *Author Manuscript of* "Outer Retinal Structure in Best Vitelliform Macular Dystrophy," Published in final edited form as: JAMA Ophthalmol., Sep. 2013, vol. 131, No. 9, pp. 1207-1215. <doi: 10.1001/jamaophthalmol.2013.387>.
Kim, J., et al., "Incubator embedded cell culture imaging system (EmSight) based on Fourier ptychographic microscopy," Biomedical Optics Express, vol. 7, No. 8, Aug. 1, 2016, pp. 3097-3110, <doi: 10.1364/BOE.7.003097>.
Kim, M., et al., "High-speed synthetic aperture microscopy for live cell imaging," Optics Letters, vol. 36, No. 2, Jan. 15, 2011, pp. 148-150. <doi:10.1364/OL.36.000148>.
Kirkland, A.I., et al., "Multiple beam tilt microscopy for super resolved imaging," Journal of Electron Microscopy (Tokyo) Jan. 1, 1997, vol. 46, No. 1, pp. 11-22. [doi: 10.1093/oxfordjournals.jmicro.a023486].
Kirkland, A.I., et al., "Super-resolution by aperture synthesis: tilt series reconstruction in CTEM," Elsevier Science B.V., Ultramicroscopy 57, Mar. 1995, pp. 355-374, <doi:10.1016/0304-3991(94)00191-O>.
Kozak, I., "Retinal imaging using adaptive optics technology," Saudi Journal of Ophthalmology, vol. 28, No. 2, Feb. 25, 2014, pp. 117-122. <doi:10.1016/j.sjopt.2014.02.005>.
Lauer, V., "New Approach to optical diffraction tomography yielding a vector equation of diffraction tomography and a novel tomographic microscope," Journal of Microscopy, Feb. 2002, vol. 205, No. 2, pp. 165-176. <doi: 10.1046/j.0022-2720.2001.00980.x>.
Lee, K., et al., "Synthetic Fourier transform light scattering," Optics Express, vol. 21, No. 19, Sep. 23, 2013, pp. 22453-22463, <doi:10.1364/OE.21.022453>.
Lu, H., et al., "Quantitative phase imaging and complex field reconstruction by pupil modulation differential phase contrast," Optics Express, vol. 24, No. 22, Oct. 31, 2016, pp. 25345-25361, <doi:10.1364/QE.24.025345>.
Luxexcel® Brochure, "Luxexcel: 3D Printing Service Description" pp. 1-5, [retrieved on Mar. 7, 2016] <URL: http://www.luxexcel.com>.

(56) References Cited

OTHER PUBLICATIONS

Medoff, B.P., et al., "Iterative convolution backprojection algorithms for image reconstruction from limited data," Journal of the Optical Society of America, vol. 73, No. 11, Nov. 1, 1983, pp. 1493-1500, <doi: 10.1364/JQSA.73.001493>.
Meyer, R.R., et al., "A new method for the determination of the wave aberration function of high-resolution TEM. 2. Measurement of the antisymmetric aberrations," Ultramicroscopy, vol. 99, No. 2-3, May 2004, pp. 115-123. <doi: 10.1016/j.ultramic.2003.11.001>.
Moreno, I., "Creating a desired lighting pattern with an LED array," Proceedings of SPIE, Eighth International Conference on Solid State Lighting, vol. 705811, Sep. 2, 2008, pp. 9. <doi:10.1117/12.795673>.
Mrejen, S., et al., "Adaptive Optics Imaging of Cone Mosaic Abnormalities in Acute Macular Neuroretinopathy," Ophthalmic Surgery, Lasers & Imaging Retina, vol. 45, No. 6, Nov./Dec. 2014, pp. 562-569. <doi: 10.3928/23258160-20141118-12>.
Ou, X., et al., "Aperture scanning Fourier ptychographic microscopy," Biomedical Optics Express, vol. 7, No. 8, Aug. 1, 2016, pp. 3140-3150. <doi:10.1364/BOE.7.003140>.
Ou. X., et al., *pre-published manuscript of* "Embedded pupil function recovery for Fourier ptychographic microscopy," (submitted on Dec. 26, 2013 (this version, v1); revised Feb. 12, 2014; accepted Feb. 17, 2014; published Feb. 24, 2014) pp. 1-13. <doi: 10.1364/OE.22.004960>.
Pacheco, S., et al., "Reflective Fourier Ptychography," Journal of Biomedical Optics, vol. 21, No. 2, Feb. 18, 2016, pp. 026010-1-026010-7. <doi: 10.1117/1.JB0.21.2.026010> [retrieved on Mar. 8, 2016] <URL:http://biomedicaloptics.spiedigitallibrary.org>.
Phillips, Z., et al., "Multi-Contrast Imaging and Digital Refocusing on a Mobile Microscope with a Domed LED Array," PLoS One, vol. 10, No. 5, May 13, 2015, pp. 1-13.<doi:10.1371/journal.pone.0124938>.
Reinhard, E., et al., "High Dynamic Range Imaging: Acquisition, Display, and Image-based Lighting" Second Edition § 5.2 HDR Image Capture: Morgan Kaufmann, May 28, 2010, pp. 148-151. <ISBN: 9780123749147>.
Rossi, E.A., et al., "In vivo imaging of retinal pigment epithelium cells in age related macular degeneration," Biomedical Optics Express, vol. 4, No. 11, Nov. 1, 2013, pp. 2527-2539. <doi: 10./1364/BOE.4.002527].
Tam, K., et al., "Tomographical imaging with limited-angle input," Journal of the Optical Society of America, vol. 71, No. 5, May 1981, pp. 582-592. <doi:doi.org/10.1364/JOSA.71.000582>.
Tian, L., et al., "3D differential phase-contrast microscopy with computational illumination using an LED array," Optics Letters, vol. 39, No. 5, Mar. 1, 2014, pp. 1326-1329. <doi:10.1364/OL39.001326>.
Tian, L., et al., "Computational illumination for high-speed in vitro Fourier ptychographic microscropy," Optica: Research Article, vol. 2, No. 10, Oct. 14, 2015, pp. 904-911. <doi:10.1364/OPTICA.2.000904>.
Vulovic, M., et al., "When to use the projection assumption and the weak-phase object approximation in phase contrast cryo-EM," Ultramicroscopy, vol. 136, Jan. 2014, pp. 61-66.<doi:10.1016/j.ultramic.2013.08.002>.
Wang, Q., et al., "Adaptive Optics Microperimetry and OCT Images Show Preserved Function and Recovery of Cone Visibility in Macular Telangiectasia Type 2 Retinal Lesions," Investigative Ophthalmology Visual Science, vol. 56, No. 2, Feb. 2015, pp. 778-786. <doi:10.1167/iovs.14-15576> [retrieved on Apr. 5, 2016] [URL: http://iovs.arvojournals.org].
Williams, A., et al., "Fourier ptychographic microscopy for filtration-based circulating tumor cell enumeration and analysis," Journal of Biomedical Optics, vol. 19, No. 6, Jun. 20, 2014, pp. 066007.1-66007.8. <doi: 10.1117/1.JBO.19.6.066007> [retrieved Feb. 10, 2016] <URL:http://biomedicaloptics.spiedigitallibrary.org>.
Wu, J., et al., "Harmonically matched grating-based full-field quantitative high-resolution phase microscope for observing dynamics of transparent biological samples," Optics Express, vol. 15, No. 26, Dec. 24, 2007, pp. 18141-18155. <doi:10.1364/OE.15.018141>.
Wu, J., et al., "Paired-angle-rotation scanning optical coherence tomography forward-imaging probe," Optics Letters, vol. 31, No. 9, May 1, 2006, pp. 1265-1267. <doi:10.1364/OL.31.001265>.
Yeh, et al., "Experimental robustness of Fourier ptychography phase retrieval algorithms," Optics Express, vol. 23, No. 26, Dec. 28, 2015, pp. 33214-33240. <doi: 10.1364/OE.23.033214>.
Zeiss, C., "Microscopy: Cells Need The Perfect Climate. System Solutions for Live Cell Imaging under Physiological Conditions," ZEISS Product Brochure, Carl Zeiss Microscopy GmbH Co., Feb. 2008, pp. 42. <URL: http://www.zeiss.de/incubation>.
Zhang, Y., et al., "Photoreceptor perturbation around subretinal drusenoid deposits as revealed by adaptive optics scanning laser ophthalmoscopy," HHS Public Access, Am J Ophthalmol. Author Manuscript,Sep. 1, 2015, pp. 22. (Published in final edited form as: Am J Ophthalmol. Sep. 2014; 158(3): 584-96.e1.).
Zheng, G., "Fourier Ptychographic Imaging: A MATLAB tutorial," IOP Concise Physics, Morgan & Claypool Publication, San Rafael, CA., May 2016, pp. 96. <ISBN: 978-1-6817-4272-4 (ebook)> <doi: 10.1088/978-1-6817-4273-1>.
U.S. Office Action dated May 19, 2017 in U.S. Appl. No. 15/081,659.
U.S. Appl. No. 15/081,659, filed Mar. 25, 2016, Chung, J. et al.
U.S. Appl. No. 15/620,674, filed Jun. 12, 2017, Chung, J. et al.
U.S. Appl. No. 15/636,494, filed Jun. 28, 2017, Kim, J. et al.
U.S. Office Action dated Jan. 25, 2018 in U.S. Appl. No. 14/065,280.
Notice of Allowance dated Dec. 4, 2017 in U.S. Appl. No. 14/065,305.
Notice of Allowance dated Jan. 26, 2018 in U.S. Appl. No. 15/209,604.
Notice of Allowance dated Jan. 23, 2018 in U.S. Appl. No. 15/206,859.
Notice of Allowance dated Oct. 11, 2017 in U.S. Appl. No. 14/572,493.
U.S Final Office Action dated Dec. 28, 2017 in U.S. Appl. No. 14/710,947.
U.S. Final Office Action dated Dec. 14, 2017 in U.S. Appl. No. 14/960,252.
U.S. Office Action dated Aug. 31, 2017 in U.S. Appl. No. 15/636,494.
U.S. Notice of Allowance dated Sep. 20, 2017 in U.S. Appl. No. 15/007,196.
U.S. Notice of Allowance dated Jun. 27, 2018 in U.S. Appl. No. 15/636,494.
Office Action dated Nov. 30, 2017 in U.S. Appl. No. 15/007,159.
Office Action dated Apr. 4, 2018 issued in U.S. Appl. No. 15/003,559.
Office Action dated Nov. 3, 2017 in U.S. Appl. No. 15/068,389.
Office Action Interview Summary dated May 3, 2018 in U.S. Appl. No. 15/068,389.
Final Office Action dated Jun. 6, 2018 issued in U.S. Appl. No. 15/068,389.
Notice of Allowance dated Oct. 20, 2017 in U.S. Appl. No. 15/081,659.
Notice of Allowance dated Feb. 9, 2018 in U.S. Appl. No. 15/081,659.
Office Action dated Apr. 13, 2018 issued in U.S. Appl. No. 15/160,941.
European Extended Search Report dated Jun. 6, 2018 issued in Application No. 15865492.1.
Extended European Search Report dated Jul. 3, 2018 issued in Application No. EP 15874344.3.
Chinese Third Office Action [Summary in English] dated Jul. 24, 2017 issued in Application No. 201380068831.6.
Chinese First Office Action [Summary in English] dated Aug. 2, 2017 issued in Application No. CN 201480054301.0.
Australian Office Action dated Sep. 18, 2017 issued in Application No. AU 2014296034.
International Preliminary Report on Patentability dated Sep. 28, 2017 issued in Application No. PCT/US2016/022116.
Japanese Office Action dated Oct. 17, 2017 issued in Application No. 2015-539884.
Chinese Office Action [Summary in English] dated Oct. 26, 2017 issued in CN 201480057911.6.
International Preliminary Report on Patentability dated Nov. 30, 2017 issued in PCT/US2016/033638.
Australian Examination Report 1/Office Action dated Jan. 18, 2018 issued in AU 2014308673.
Chinese First Office Action dated Feb. 24, 2018 issued in CN 201680003937.1.

(56) References Cited

OTHER PUBLICATIONS

Abrahamsson, S., et al., "Fast multicolor 3D imaging using aberration-corrected mulitfocus microscopy," Brief Communications: Nature Methods, vol. 10, No. 1, Jan. 2013, pp. 60-65, <doi:10.1038/nmeth.2277>.
Holloway, J., et al. "SAVI: Synthetic apertures for long-range, subdiffraction-limited visible imaging using Fourier ptychography," Science Advances | Research Article, vol. 3, No. 4, Apr. 14, 2017, pp. 1-11. <doi:10.1126/sciadv.1602564> [retrieved on Nov. 28, 2017] <URL:http://advances.sciencemag.org/>.
Jacques, et al., "Imaging Superficial Tissues With Polarized Light," Lasers in Surgery and Medicine, vol. 26, No. 2, Apr. 25, 2000, pp. 119-129.
Jenson, et al. "Types of imaging, Part 2: An Overview of Fluorescence Microscopy." The Anatomical Record, vol. 295, No. 10, Oct. 1, 2012, pp. 1621-1627.
Kner, P., "Phase diversity for three-dimensional imaging," Journal of the Optical Society of America A, vol. 30, No. 10, Oct. 1, 2013, pp. 1980-1987. <doi:10.1364/JOSAA.30.001980>.
Sarder, et al. "Deconvolution Methods for 3-D Fluorescence Microscopy Images," IEEE Signal Processing Magazine, vol. 23, No. 3, May 2006, pp. 32-45.
Sankaranarayanan, Aswin C., et al., "CS-MUVI: Video Compressive Sensing for Spatial-Multiplexing Cameras," Proceedings of the IEEE International Conference Computational Photography (ICCP), Apr. 2012, pp. 11. <doi:10.1109/ICCPhot.2012.6215212>.
Wills, S., "Synthetic Apertures for the Optical Domain," Optics & Photonics News Article [webpage], The Optical Society (OSA), Apr. 18, 2017, pp. 2. <URL: https://www.osa-opn.org/home/newsroom/2017/april/synthetic_apertures_for_the_optical_domain/>.
Zheng, G., et al., "Wide-field, high-resolution Fourier ptychographic microscopy," Nature Photonics, vol. 7, Sep. 2013, Published Online Jul. 28, 2013, pp. 739-746. <doi:10.1038/NPHOTON.2013.187>.
U.S. Appl. No. 15/963,966, filed Apr. 26, 2018, Ou et al.
U.S. Appl. No. 15/959,050, filed Apr. 20, 2018, Horstmeyer et al.
Preliminary Amendment dated Jun. 13, 2018 filed in U.S. Appl. No. 15/820,295.
U.S. Final Office Action dated Nov. 29, 2018 in U.S. Appl. No. 14/065,280.
U.S. Office Action dated Jun. 26, 2019 issued in U.S. Appl. No. 14/065,280.
U.S. Office Action dated Dec. 26, 2018 in U.S. Appl. No. 15/963,966.
U.S. Notice of Allowance dated Apr. 19, 2019 in U.S. Appl. No. 15/963,966.
U.S. Office Action dated Dec. 26, 2018 in U.S. Appl. No. 15/959,050.
U.S. Final Office Action dated Jun. 3, 2019 in U.S. Appl. No. 15/959,050.
U.S. Notice of Allowance dated Sep. 17, 2018 in U.S. Appl. No. 15/820,295.
U.S. Notice of Allowance dated Jan. 14, 2019 in U.S. Appl. No. 15/820,295.
U.S. Notice of Allowance dated Apr. 16, 2019 in U.S. Appl. No. 15/820,295.
U.S. Notice of Allowance dated Jul. 25, 2018 in U.S. Appl. No. 14/710,947.
U.S. Office Action dated Mar. 8, 2019 in U.S. Appl. No. 16/171,270.
U.S. Office Action dated Dec. 13, 2018 in U.S. Appl. No. 14/960,252.
U.S. Notice of Allowance dated Aug. 12, 2019 in U.S. Appl. No. 14/960,252.
U.S. Notice of Allowance dated Sep. 17, 2019 in U.S. Appl. No. 14/960,252.
US Ex Parte Quayle Action dated Aug. 8, 2019 issued in U.S. Appl. No. 16/242,934.
U.S. Notice of Allowance dated Oct. 5, 2018 in U.S. Appl. No. 15/636,494.
U.S. Notice of Allowance dated Jul. 16, 2018 in U.S. Appl. No. 15/007,159.
U.S. Office Action dated Apr. 4, 2019 in U.S. Appl. No. 16/162,271.
U.S. Office Action dated Sep. 7, 2018 in U.S. Appl. No. 14/979,154.
U.S. Final Office Action dated May 30, 2019 in U.S. Appl. No. 14/979,154.
U.S. Final Office Action dated Dec. 10, 2018 issued in U.S. Appl. No. 15/003,559.
U.S. Office Action dated Jun. 26, 2019 issued in U.S. Appl. No. 15/003,559.
U.S. Office Action dated Jan. 17, 2019 issued in U.S. Appl. No. 15/068,389.
U.S. Final Office Action dated Jun. 19, 2019 issued in U.S. Appl. No. 15/068,389.
U.S. Notice of Allowance dated Sep. 16, 2019 issued in U.S. Appl. No. 15/068,389.
U.S. Notice of Allowance dated Oct. 19, 2018 issued in U.S. Appl. No. 15/160,941.
U.S. Notice of Allowance dated Jan. 15, 2019 issued in U.S. Appl. No. 15/620,674.
U.S. Notice of Allowance dated Apr. 29, 2019 issued in U.S. Appl. No. 15/620,674.
U.S. Notice of Allowance dated Aug. 14, 2019 issued in U.S. Appl. No. 15/620,674.
U.S. Notice of Allowance dated Sep. 25, 2019 issued in U.S. Appl. No. 15/620,674.
U.S. Office Action dated Oct. 11, 2019 issued in U.S. Appl. No. 16/179,688.
Chinese Third Office Action dated Jul. 13, 2018 issued in CN 201480057911.6.
Japanese First Office Action dated Aug. 7, 2018 issued in Application No. JP 2016-531919.
Chinese First Office Action dated Jan. 28, 2019 issued in CN 201580072950.8.
Extended European Search Report dated Aug. 8, 2018 issued in Application No. EP 16744002.3.
European Extended Search Report dated Aug. 14, 2018 issued in EP 16744003.1.
Chinese First Office Action dated Dec. 28, 2018 issued in Application No. CN 201680005491.6.
Chinese Office Action [Description in English] dated May 31, 2016 issued in Application No. CN 201380068831.6.
Chinese Second Office Action [Description in English dated Jan. 22, 2017 issued in Application No. CN201380068831.6.
Chinese First Office Action dated Apr. 19, 2019 issued in Application No. CN 201680006738.6.
Chinese First Office Action dated Dec. 26, 2018 issued in Application No. CN 201580067354.0.
Extended European Search Report dated Sep. 12, 2018 issued in Application No. EP 16740769.1.
Chinese Second Office Action dated Jul. 3, 2018 issued in Application No. CN 201480054301.0.
Extended European Search Report dated Oct. 25, 2018 issued in Application No. EP 16765505.9.
Chinese First Office Action dated Apr. 19, 2019 issued in Application No. CN 201680014898.5.
International Search Report and Written Opinion dated Feb. 22, 2019 issued in PCT/US2018/059059.
Adie, et al., "Computational adaptive optics for broadband optical interferometric tomography of biological tissue," Proc. Natl. Acad. Sci. USA 109, 7175-7180 (May 8, 2012).
Bian, et al., "Content adaptive illumination for Fourier ptychography," Optics Letters, vol. 39, Aug. 2014, pp. 1-6.
Bioucas-Dias, et al., "Total variation-based image deconvolution: a majorization-minimization approach," ICASSP (2), pp. 861-864 (May 14, 2006).
Booth, "Adaptive optical microscopy: the ongoing quest for a perfect image," Light Sci. Appl. 3, e165 (Apr. 25, 2014).
Chung, et al., "Computational aberration compensation by coded-aperture-based correction of aberration obtained from optical Fourier coding and blur estimation," Optica, vol. 6, May 10, 2019, pp. 647-661.
Desjardins, et al., "Angle-resolved Optical Coherence Tomography with sequential selectivity for speckle reduction" Optics Express, vol. 15, No. 10, May 14, 2007, pp. 6200-6209.
Dowski, et al., "Extended depth of field through wavefront coding," Applied Optics, vol. 34, No. 11, Apr. 10, 1995, pp. 1859-1866.

(56) References Cited

OTHER PUBLICATIONS

Evered, et al., "Accuracy and perceptions of virtual microscopy compared with glass slide microscopy in cervical cytology," Cytopathology, vol. 22, Feb. 2, 2010, pp. 82-87.
Fergus, et al., "Removing camera shake from a single photograph," ACM Trans. Graph. 25, 787-794 (2006).
Fienup and Miller, "Aberration correction by maximizing generalized sharpness metrics," J. Opt. Soc. Am. A 20, pp. 609-620 (Apr. 2003).
Fried, D.L.,"Anisoplanatism in adaptive optics," J. Opt. Soc. Am. vol. 72, No. 1, Jan. 1982, pp. 52-61.
Gunjala, et al., "Aberration recovery by imaging a weak diffuser," Optics Express vol. 26, No. 16, Aug. 6, 2018, pp. 21054-21068.
McConnell, et al., "A novel optical microscope for imaging large embryos and tissue volumes with sub-cellular resolution throughout," eLife 5, e18659, Sep. 23, 2016, pp. 1-15.
Muyo, et al., "Wavefront coding for athermalization of infrared imaging systems," Proc. SPIE 5612, Dec. 6, 2004, pp. 227-235.
Muyo, et al., "Infrared imaging with a wavefront-coded singlet lens," Optics Express, vol. 17, Nov. 5, 2009, pp. 21118-21123.
Ginner, et al., "Holographic line field en-face OCT with digital adaptive optics in the retina in vivo," Biomed. Opt. Express 9, 472-485 (Feb. 1, 2018).
Ginner, et al., "Noniterative digital aberration correction for cellular resolution retinal optical coherence tomography in vivo," Optica, vol. 4, Aug. 2017, pp. 924-931.
Godden, T.M. et al., "Ptychographic microscope for three-dimensional imaging," Optics Express, vol. 22, No. 10, May 19, 2014, pp. 12513-12523.
Gustafsson, M.,"Nonlinear structured-illumination microscopy: wide-field fluorescence imaging with theoretically unlimited resolution," Proc. Natl. Acad. Sci. USA 102, 13081-13086 (Sep. 13, 2005).
H. Hofer, L. Chen, G. Y. Yoon, B. Singer, Y. Yamauchi, and D. R. Williams, "Improvement in retinal image quality with dynamic correction of the eye's aberrations," Opt. Express 8, 631-643 (May 21, 2001).
Hillmann, et al., "Aberration-free volumetric high-speed imaging of in vivo retina," Sci. Rep. 6, 35209 (Oct. 20, 2016).
Kamal, et al., "In situ retrieval and correction of aberrations in moldless lenses using Fourier ptychography," Opt. Express, vol. 26, No. 3, pp. 2708-2719 (Feb. 5, 2018).
Kuang, et al., "Digital micromirror device-based laserillumination Fourier ptychographic microscopy," Optics Express, vol. 23, Oct. 5, 2015, pp. 26999-27010.
Kubala, et al., "Reducing complexity in computational imaging systems," Optics Express vol. 11, Sep. 8, 2003, pp. 2102-2108.
Kumar, et al., "Subaperture correlation based digital adaptive optics for full field optical coherence tomography," Optics Express, vol. 21, May 6, 2013, pp. 10850-10866.
Kundur, et al., "Blind Image Deconvolution," IEEE Signal Processing Magazine, vol. 13, No. 3, May 1996, pp. 43-64.
Levin et al., "Image and depth from a conventional camera with a coded aperture," ACM Transactions on Graphics, vol. 26, No. 3, Article 70, Jul. 2007, pp. 70-71-70-9.
Levin, et al., "Understanding blind deconvolution algorithms," IEEE Trans. Pattern Anal. Mach. Intell., vol. 33, No. 12, Dec. 2011, pp. 2354-2367.
Li, et al., "Separation of threedimensional scattering effects in tilt-series Fourier ptychography," Ultramicroscopy 158, 1-7 (Jun. 14, 2015).
Li, et al., "GPU accelerated parallel FFT processing for Fourier transform hyperspectral imaging," Applied Optics, vol. 54, No. 13, May 1, 2015, pp. D91-D98.
Maiden, A.M., et al., "Ptychographic transmission microscopy in three dimensions using a multi-slice approach," Journal of the Optical Society of America A., vol. 29, No. 8, Aug. 1, 2012, pp. 1606-1614.
Marcos, et al., "Vision science and adaptive optics, the state of the field," Vision Research, vol. 132, Feb. 27, 2017, pp. 3-33.
Martins da Silva et al., "Photosensitivity and epilepsy: current concepts and perspectives—a narrative review," Seizure, vol. 50, Apr. 4, 2017, pp. 209-218.
Neumaier, "Solving ill-conditioned and singular linear systems: a tutorial on regularization," SIAM Rev. 40, (1998), pp. 636-666.
Pan, et al., "Subwavelength resolution Fourier ptychography with hemispherical digital condensers," Opt. Express 26, 23119-23131 (Sep. 3, 2018).
Pan, et al., "System calibration method for Fourier ptychographic microscopy," J. Biomed. Opt. 22, 096005 (Sep. 12, 2017).
Pan, et al., "Three-dimensional space optimization for near-field ptychography," Opt. Express 27, 5433-5446 (Feb. 18, 2019).
Pankajakshan, P., "Blind Deconvolution for Confocal Laser Scanning Microscopy," Doctoral dissertation, Universite Nice Sophia Antipolis, 2009. <URL: https://tel.archives-ouvertes.fr/tel-00474264>.
Qian, et al., "Large-scale 3D imaging of insects with natural color," Opt. Express 27, 4845-4857 (Feb. 18, 2019).
Reinig, et al., "Adaptative optics microscopy enhances image quality in deep layers of CLARITY processed brains of YFP-H mice" Proc., of SPIE, vol. 9690, (Mar. 9, 2016) pp. 969008-1-969008-12, <doi: 10.1117/12.2213283>.
Rha, et al., "Adaptive optics flood-illumination camera for high speed retinal imaging," Opt. Express vol. 14, May 15, 2006, pp. 4552-4569.
Shemonski, et al., "Computational high-resolution optical imaging of the living human retina," Nat. Photonics, vol. 9, Jul. 2015, pp. 440-443.
Soulez, et al., "Blind deconvolution of 3D data in wide field fluorescence microscopy" In 2012 9th IEEE International Symposium on Biomedical Imaging (ISBI) May 2, 2012, pp. 1735-1738.
Sun, et al., "Efficient positional misalignment correction method for Fourier ptychographic microscopy," Biomedical Optics Express vol. 7, No. 4, Mar. 17, 2016, pp. 1336-1350.
Sun, et al., "Resolution-enhanced Fourier ptychographic microscopy based on high-numerical-aperture illuminations," Scientific Reports, vol. 7, No. 1187, Apr. 26, 2017, pp. 1-11.
Sun, et al., "Sampling criteria for Fourier ptychographic microscopy in object space and frequency space," Optics Express vol. 24, No. 14, Jul. 11, 2016, pp. 15765-15781.
Thiébaut and Conan, "Strict a priori constraints for maximumlikelihood blind deconvolution," J. Opt. Soc. Am. A, vol. 12, No. 3, Mar. 1995, pp. 485-492.
Tian and Waller, "3D intensity and phase imaging from light field measurements in an LED array microscope," Optica vol. 2, No. 2, Feb. 2015, pp. 104-111.
Tomer et al., "Advanced CLARITY for rapid and high-resolution imaging of intact tissues," Nat. Protoc., vol. 9, No. 7, Jul. 2014, pp. 1682-1697.
Wade, et al., "A fast, robust pattern recognition system for low light level image registration and its application to retinal imaging," Optics Express vol. 3, No. 5, Aug. 31, 1998, pp. 190-197.
Williams, D., "Imaging Single Cells in the Living Retina," Vis. Res. 51, pp. 1379-1396 (Jul. 1, 2011).
Yaroslavsky, "Image Resampling and Building Continuous Image Models", Chapter 6, Theoretical Foundations of Digital Imaging Using MATLAB , pp. 293-342 (CRC Press, 1 edition, Nov. 26, 2012).
Yuan, et al., "Image deblurring with blurred/noisy image pairs," ACM Trans. Graph. 26, Jul. 29, 2007, pp. 1-10.
Zhou, et al., "What are Good Apertures for Defocus Deblurring?" in 2009 IEEE International Conference on Computational Photography (IEEE, Apr. 16-17, 2009), pp. 1-8.
U.S. Office Action dated Sep. 23, 2019 issued in U.S. Appl. No. 16/252,465.
U.S. Appl. No. 16/252,465, filed Jan. 18, 2019, Ou et al.
U.S. Appl. No. 16/552,948, filed Aug. 27, 2019, Chung et al.
U.S. Appl. No. 16/572,497, filed Sep. 16, 2019, Ou et al.
U.S. Notice of Allowance dated Jan. 29, 2020 issued in U.S. Appl. No. 14/065,280.
U.S. Notice of Allowance dated Nov. 20, 2019 in U.S. Appl. No. 15/959,050.

(56) References Cited

OTHER PUBLICATIONS

U.S. Notice of Allowance dated Jan. 6, 2020 in U.S. Appl. No. 14/960,252.
U.S. Notice of Allowance dated Nov. 4, 2019 issued in U.S. Appl. No. 16/242,934.
U.S. Notice of Allowance dated Feb. 18, 2020 issued in U.S. Appl. No. 16/242,934.
U.S. Notice of Allowance dated Dec. 9, 2019 in U.S. Appl. No. 16/162,271.
U.S. Notice of Allowance dated Apr. 3, 2020 in U.S. Appl. No. 16/162,271.
U.S. Notice of Allowance dated Mar. 2, 2020 in U.S. Appl. No. 14/797,154.
U.S. Notice of Allowance dated Jan. 17, 2020 issued in U.S. Appl. No. 15/003,559.
U.S. Notice of Allowance dated Jan. 24, 2020 issued in U.S. Appl. No. 15/068,389.
U.S. Final Office Action dated May 1, 2020 issued in U.S. Appl. No. 16/252,465.
U.S. Notice of Allowance dated Apr. 7, 2020 issued in U.S. Appl. No. 16/179,688.
Chinese First Office Action dated Apr. 16, 2020 issued in Application No. CN 201810576437.8.
Chinese Second Office Action dated Dec. 31, 2019 issued in CN 201580072950.8.
Chinese Second Office Action dated Nov. 12, 2019 issued in Application No. CN 201680005491.6.
Chinese Third Office Action dated May 15, 2020 issued in Application No. CN 201680005491.6.
Chinese Second Office Action dated Nov. 28, 2019 issued in Application No. CN 201680006738.6.
Chinese Second Office Action dated Mar. 19, 2020 issued in Application No. CN 201680014898.5.
U.S. Appl. No. 16/864,618, filed May 1, 2020, Zheng et al.
Chinese First Office Action dated Jan. 4, 2021 issued in Application No. CN 201811585066.6.
Chinese First Office Action dated Jan. 28, 2021 issued in Application No. CN 201910181199.5.
European First Examination Report dated Jan. 21, 2021 issued in Application No. EP 16744002.3.
Chinese First Office Action dated Oct. 11, 2020 issued in CN 201811184731.0.
European First Examination Report dated Jan. 27, 2021 issued in EP 16744003.1.
U.S. Office Action dated Aug. 28, 2020 in U.S. Appl. No. 16/572,497.
U.S. Office Action dated Aug. 7, 2020 issued in U.S. Appl. No. 16/552,948.
European First Examination Report dated Sep. 28, 2020 issued in Application No. 14837844.1.
International Preliminary Report on Patentability dated May 14, 2020 issued in PCT/US2018/059059.
Chinese Second Office Action dated Oct. 8, 2021 issued in Application No. CN 201811585066.6.
CN Office Action dated Oct. 8, 2021, in application No. CN201811585067 with English translatio.
CN Office Action dated Oct. 11, 2021, in Application No. CN201910181199.5 with English translation.
U.S. Appl. No. 17/455,640, Inventors Zheng et al., filed Nov. 18, 2021.
U.S. Notice of Allowance dated Apr. 6, 2021 issued in U.S. Appl. No. 16/552,948.
U.S. Office Action dated May 25, 2021 issued in U.S. Appl. No. 16/864,618.
Chinese Second Office Action dated Oct. 11, 2021 issued in Application No. CN 201910181199.5.
U.S. Appl. No. 17/455,640, filed Nov. 18, 2021, Zheng et al.

* cited by examiner

FREE ORIENTATION FOURIER CAMERA

CROSS-REFERENCES TO RELATED APPLICATIONS

This application claims benefit of and priority to U.S. Provisional Patent Application No. 61/952,318 titled "Free Orientation Fourier Camera," filed on Mar. 13, 2014, which is hereby incorporated by reference in its entirety and for all purposes.

BACKGROUND

Certain embodiments described herein are generally related to imaging techniques, and more specifically, to methods, devices, and systems for Fourier camera imaging in applications such as, for example, photography for mole tracking.

Melanoma is currently the leading cause of cancer-related deaths among Americans (almost 10,000 deaths annually) with over 75,000 new cases annually. The incidence of melanoma has been rising steadily. Though excision can be curative at early stages, many melanomas are not detected in time and may become locally extensive or metastasize to other locations. Early detection of melanoma is critical to reduce its morbidity and mortality. In approximately 75% of cases, melanomas arise de novo. In the remaining 25%, they arise from pre-existing moles. It is therefore critical to have a method for longitudinally following the behavior of moles in order to rapidly detect any growth or other changes that may signal transformation of the mole towards more concerning behavior. Hence, tracking moles is an important part of screening patients for melanoma.

The American Academy of Dermatology (AAD) has endorsed a protocol that can be utilized to identify moles which may be of concern. This protocol is abbreviated as ABCDE: where A=asymmetry, B=border, C=color, D=diameter and E=evolution. The first four criteria are utilized to identify already existing moles that may be concerning for atypia or malignancy. However, evolution is probably the most important consideration. A changing mole indicates some cellular activity, and these evolving moles are of greatest concern for malignant transformation. Dermatologists therefore recommend serial examinations of patients ('skin checks') to assess for the possibility of skin cancer.

With conventional cameras, the same distance to the skin surface and same orientation of the camera needs to be maintained at each clinic visit to take comparable, quantifiable measurements of moles between clinic visits. If distance and orientation are not maintained, magnification, focus, and orientation of the mole images may vary, making it difficult to distinguish mole growth from image distortion. Also, conventional cameras have a single adjustable plane of focus. When imaging a mole on a curved skin surface (such as on the bridge of the nose), a single adjustable plane may provide poor image quality across the mole. For these reasons, it can be difficult to use conventional cameras to detect subtle changes in moles.

BRIEF SUMMARY

Aspects of this disclosure concern imaging techniques, and more specifically Fourier camera systems and methods thereof, which may be particularly useful in applications such as, for example, mole tracking.

Embodiments pertain to a Fourier camera comprising a first optical system, a second optical system, a variable aperture filter, and a light detector. The first optical system configured to receive illumination reflected from a curved sample surface. The variable aperture filter configured to move an aperture to a plurality of aperture locations in a Fourier plane, wherein the aperture filters light from the first optical system to the second optical system. The light detector configured to receive light from the second optical system, and configured to acquire a plurality of raw intensity images of the curved sample surface corresponding to the plurality of aperture locations, wherein the raw images are iteratively updated in overlapping regions in Fourier space to generate a focused, substantially uniform resolution image of the curved sample surface, and wherein the overlapping regions correspond to the plurality of aperture locations. In some cases, the Fourier camera further comprising a processor in communication with the light detector to receive the acquired raw intensity images. The processor is configured to divide the acquired raw intensity images into a plurality of tiles, and for each tile, iteratively update regions in Fourier space with data associated with the acquired raw intensity images for the tile to determine a complex tile image and then focus the complex tile image. The processor is further configured to combine the focused complex tile images to construct a focused, substantially uniform resolution image of the curved sample surface.

Embodiments pertain to a method of using a Fourier camera to capture one or more focused, substantially uniform resolution images of a curved sample surface, the Fourier camera comprising a first optical system, a second optical system, a variable aperture filter, and a light detector. The method comprises (a) receiving at a first optical system illumination reflected from the curved sample surface; (b) moving, with a variable aperture filter, an aperture to a plurality of aperture locations at a Fourier plane, wherein the aperture filters illumination from the first optical system to the second optical system; and (c) acquiring a plurality of raw intensity images of the curved sample surface based on light received from the second optical system, wherein each raw intensity image is acquired while the aperture is at a different aperture location of the plurality of aperture locations, wherein the raw images are iteratively updated in overlapping regions in Fourier space to generate a focused, substantially uniform resolution image of the curved sample surface, and wherein the overlapping regions correspond to the plurality of aperture locations.

These and other features are described in more detail below with reference to the associated drawings.

DETAILED DESCRIPTION

Figure 1:
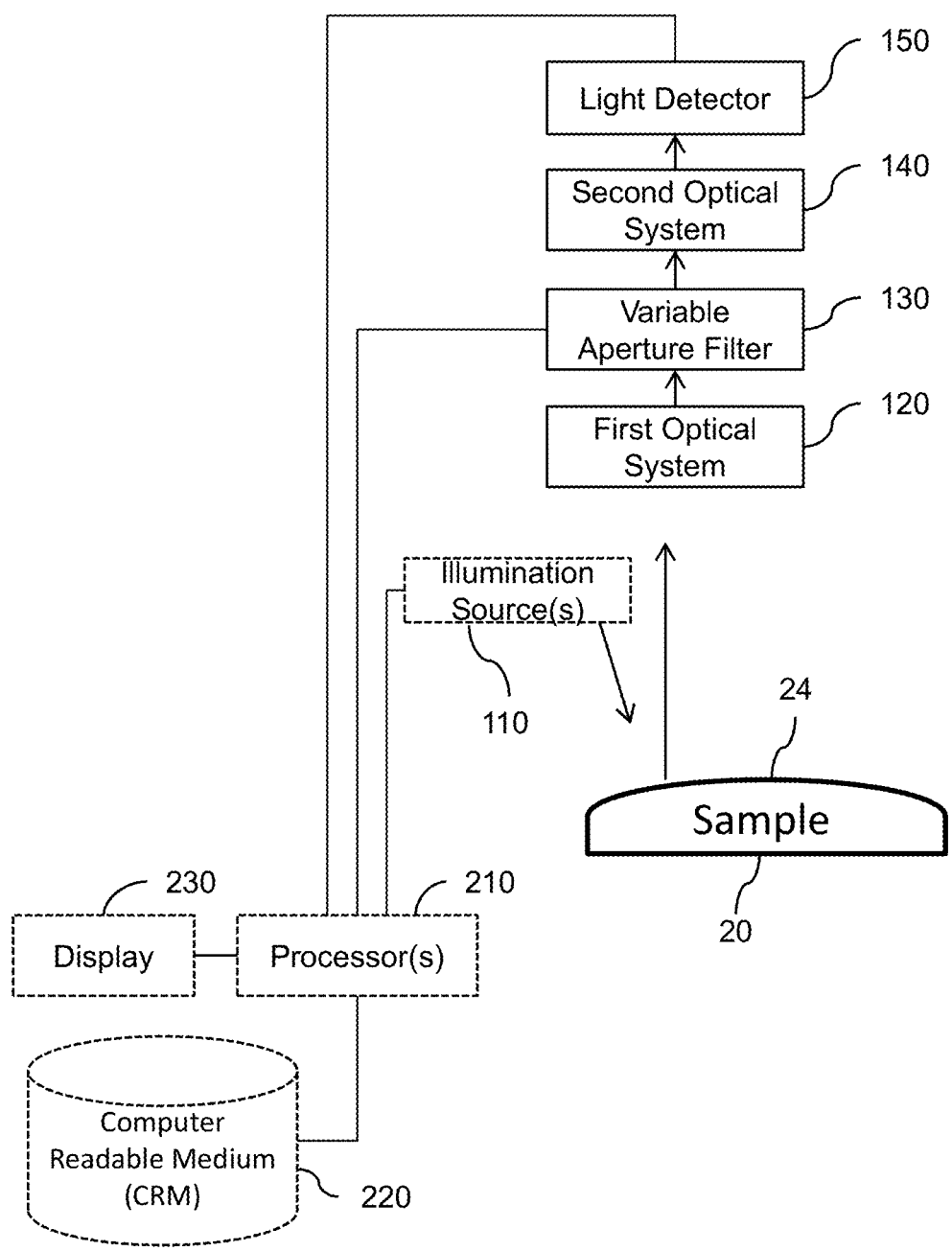
FIG. 1 is a schematic drawing of components of a Fourier camera system, according to embodiments.

Embodiments of the present invention will be described below with reference to the accompanying drawings. The features illustrated in the drawings may not be to scale. Certain aspects described herein pertain to Fourier camera systems and Fourier camera methods.

I. Fourier Camera Systems

Certain embodiments pertain to Fourier camera systems/methods that can generate a topological 3-D and substantially uniformly high resolution image of a curved sample surface at each imaging cycle. These Fourier camera systems/methods can use these uniform resolution 3-D profile images to account for position, orientation, and magnification changes between imaging cycles as may occur, for example, in a handheld imaging device. Embodiments of Fourier camera systems and methods that can account for position and orientation changes between imaging cycles are described as "free orientation," which may provide robust techniques for tracking mole growth or changes to another object of interest.

According to certain embodiments, Fourier camera systems are point-and-shoot devices that can capture and render an objective topology image of an object (e.g., mole) on a curved surface that is highly tolerant to device position and orientation variations. In some cases, the Fourier camera systems operate using a phase retrieval technique to render a final 3D profile image. To operate these point-and-shoot devices, an operator points the Fourier camera system at the sample surface being imaged and activates by, for example, pressing a button or other activating mechanism. Within the Fourier camera system of embodiments, there is a variable aperture filter that translates an aperture to different positions in a Fourier plane while the light detector captures (snaps) a series of images, one for each unique aperture configuration. In some cases, the Fourier camera system comprises a digitally addressable spatial light modulator (SLM) that acts as the variable aperture filter. In these cases, associated instructions (to SLM and/or light detector) may be used to translate the SLM aperture while capturing the images with the light detector so that each image captured has a unique aperture configuration. After image acquisition, instructions may be used to process the image sequence into a high-resolution topological reconstruction.

In certain embodiments, a Fourier camera system comprises a variable aperture filter in the form of a spatial light modulator (SLM). In one example, the SLM may be digitally addressed to quickly shift a pupil function by using a liquid crystal based modulator, which selectively blocks light depending upon which SLM pixels are electronically triggered. In one exemplary operation of the Fourier camera system, an operator points the system at a sample surface and activates the system. The Fourier camera system projects an illumination light beam on the sample surface. The Fourier camera system then acquires a sequence of images of the sample surface while using the SLM to selectively block different areas of the light field entering into the camera's pupil plane. The sequence of images comprises M raw image frames (e.g., low resolution intensity images), where M equals N, the number of total shifted SLM pupil functions. The SLM display creates angular diversity in the raw image frames using the SLM screen to selectively transmit different angular components of the light field. The sequence of raw images may be transformed into the final topological image using a phase retrieval technique. This phase retrieval technique can be used to synthesize image information collected at a light detector as modulated by different apertures at a Fourier plane to determine amplitude and phase (complex) profile of the light field emerging from the sample surface. In embodiments, the phase retrieval technique determines phase without direct measurement or mechanical scanning Using this phase retrieval technique, the Fourier camera system can refocus images after the images are acquired. In certain embodiments, the Fourier camera system can capture unfocused intensity images of a curved sample surface where the images are associated with different aperture locations and use these intensity images to recover a focused, high resolution, complex image of the curved sample surface.

In certain aspects, a Fourier camera system comprises a first optical system, a variable aperture filter (e.g., spatial light modulator) for generating an aperture at an intermediate plane, a second optical system, and a light detector configured to capture intensity images. The Fourier camera system may also comprise one or more illumination sources for providing illumination to a sample surface. In certain cases, the first optical system, second optical system, light detector, and sample plane of the sample surface may be arranged in a 4-f optical arrangement. The Fourier camera system may further comprise other components such as, for example, one or more of: a processor(s) (e.g., microprocessor) for performing function(s) of the Fourier camera system, a computer readable medium (CRM) for storing data, a display for providing output to a user of the Fourier camera system, and a housing for enclosing one or more components of the Fourier camera system. The housing may be compact allowing the Fourier camera system to be in a hand held form. In embodiments of the Fourier camera system that comprise a processor and CRM, the CRM may be in communication with the processor to store data to and retrieve from the CRM. In embodiments that further comprise a display, the display may be in communication with the processor to receive output data and instructions for providing output to a user. Electronic communication between components of the Fourier camera system of embodiments may be in wired or wireless form.

In certain aspects, a Fourier camera system performs one or more imaging cycles to image the sample surface, for example, during different visits to a melanoma screening clinic. Each cycle generally comprises an acquisition process, a recovery process, a screening process, and optionally an output process. During the acquisition process of an embodiment, M intensity (lower resolution) images of the sample surface corresponding to different aperture locations are acquired. During the recovery process of an embodiment, each of the M intensity images is divided into tiles, the M intensity tile images are iteratively stitched together in Fourier space to recover a complex image of the tile, each of the complex tile images are propagated to a best focal plane, and the focused (higher resolution) tile images are combined to generate a focused image of the sample surface including an object of interest. That is, if a tile complex image is not in focus, the Fourier camera system focuses the tile image. During the screening process, the images of the sample surface at different cycles are aligned and the images of the object at different cycles are compared. During the optional output process, the recovered images of the sample surface and object, a comparison of the images of the object taken over multiple cycles, and other output may be generated on a display.

In one aspect of a Fourier camera method, the Fourier camera system performs an exemplary acquisition process that acquires M intensity images at M sample times ($t_i$, i=1 to M) corresponding to different aperture locations. During this method, the illumination source illuminates the sample surface. The first optical system receives light reflected from the sample surface and the variable aperture filter generates an aperture at a plurality of N aperture locations at the Fourier plane of the sample. In many cases, there is an overlapping area between adjacent aperture regions provided at the Fourier plane. The second optical system receives light filtered by the aperture. The light detector receives light from the second optical system as modulated by the aperture at the N different aperture locations. The light detector captures a plurality of M intensity images at M sample times ($t_i$, i=1 to M) corresponding to different aperture locations of the plurality of N aperture locations. In some cases, M=N.

In one aspect of a Fourier camera method, a Fourier camera system performs an exemplary recovery process for recovering a focused 3-D profile image of the sample surface and/or a uniform resolution, focused 2-D image of the sample surface. During this recovery process, the M intensity images are divided into tiles, and the M overlapping intensity images of the tiles are iteratively stitched together in Fourier space to recover a wide-field, complex image of the tile. The tile images are propagated to different planes to determine a best focal plane and the depth at the best focal plane for each tile is determined. The Fourier camera system combines the tile images at different depths to generate a focused 3-D profile image of the sample surface and/or combines the tile images to generate a uniform resolution, focused 2-D image of the sample surface. During the recovery process, the Fourier camera system can recover a focused, higher resolution, complex image of a curved sample surface from the unfocused, lower resolution intensity images associated with different aperture locations taken during the acquisition process.

In one aspect of a Fourier camera method, a Fourier camera system performs an exemplary screening process for determining changes in the images of the object over multiple cycles. During this screening process, either the focused 3-D profile image or 2-D image of the sample surface is aligned. In one case, the images are aligned based on curvature of the sample surface as determined from the depths of the best focal planes of the tile images. Once the images from different cycles are aligned, different quantifiable object characteristics may be determined from the images of the objects within the sample surface images. For example, the boundary of the object at each cycle may be determined and then a change in the boundary may be determined to calculate a change (e.g., percentage increase or decrease) in area or a change in shape. As another example, intensity changes across the object image can be compared to determine whether there is a change of darkness in the object. As another example, the number of objects having distinct boundaries within the sample surface may be counted at each cycle and the change in the number of objects determined.

FIG. 1 is a schematic diagram of components of a Fourier camera system 100, according to embodiments. The Fourier camera system 100 comprises a first optical system 120 configured to receive light reflected from a sample surface 24 of a sample 20, a variable aperture filter 130 configured to generate an aperture at a plurality of N aperture locations in an intermediate plane (e.g., Fourier plane of sample surface 24), a second optical system 140 for receiving light through the aperture, and a detector 150 for capturing M intensity images based on incident light from the second optical system 140. The first optical system 120 may comprise a first objective lens in some cases. The second optical system 140 may comprise a second objective lens in some cases.

One or more illumination sources 110 provide illumination to sample surface 24. As denoted by the dashed box, Fourier camera system 100 may comprise the illumination source(s) 110 or the illumination source(s) 110 may be a separate component from the Fourier camera system 100. In some cases, illumination source(s) 110 provides a coherent illumination beam of illumination such as, for example, from a laser. In other cases, illumination source(s) 110 provides incoherent illumination such as, for example, from one or more light emitting diodes (LEDs). In some aspects, illumination source(s) 110 provides a collimated light. In other cases, illumination source(s) 110 provides un-collimated light.

Optionally (as denoted by the dashed boxes), Fourier camera system 100 may further comprise a processor(s) 210 for performing certain function(s) of the Fourier camera system 100 and a CRM 220 (e.g., memory) in electrical communication with the processor 210 to store information (e.g., image data) to and retrieve from the CRM 220. Also optionally (as denoted by the dashed box), the Fourier camera system 100 may further comprise a display 230 in communication with the processor 210 to receive instructions and image data for displaying images and other output on the display to, for example, a user of Fourier camera system 100. Electronic communication between certain components of Fourier camera system 100 may be in wired or wireless form. One or more of these optional components may be located separately than other components of Fourier camera system 100. For example, one or more of the optional components may be a part of a separate computing device such as, for example, a smartphone, laptop, desktop, tablet, etc.

The processor 210 is shown in electronic communication with light detector 150 to send signal(s) with control instructions to the light detector 150 to trigger sampling M intensity images at M sample times and/or to receive signal(s) with image data associated with the acquired M intensity images. Each intensity image is an intensity distribution measured over the surface of the light detector 150. The processor 210 is in electronic communication with illumination source 110 to send signal(s) with control instructions to trigger illumination at different times, for example, when activated by a user of the Fourier camera system 100. The processor 210 is in electronic communication with variable aperture filter 130 to send signal(s) with control instructions to trigger generating an aperture at different aperture locations. In one case, processor 210 may be in electrical communication with variable aperture filter 130, light detector 150, and illumination source 110, for example, to synchronize intensity image acquisition sampling times to occur while the sample surface is illuminated and an aperture is generated at the Fourier plane.

During an example of an acquisition process of a cycle performed by the Fourier camera system 100, illumination 112 is provided to the sample surface 24 and variable aperture filter 130 generates an aperture at a plurality of N aperture locations, $(X_i, Y_j)$, i=1 to m, j=1 to n, in a plane (e.g., Fourier plane of the optical arrangement). The first optical system 120 receives incident light reflected from the sample surface 24. The second optical system 140 receives light as modulated by the aperture. The light detector 150 receives light propagated by the second optical system 140. The light detector 150 acquires an intensity distribution $I_{i,j}$, i=1 to o, j=1 to p at M (=o×p) sample times, $t_{i=1\ to\ M}$, to capture a plurality of M intensity images of the sample surface 24 at this screening cycle. In one aspect, each of the M intensity images uniquely corresponds to an aperture location of the plurality of N aperture locations.

During an example of a recovery process of a cycle performed by the Fourier camera system 100, each of the intensity images of the sample surface captured by the Fourier camera system 100 is divided into multiple tile images such as, for example, a two-dimensional matrix of tiles. In some embodiments, the dimensions of a two-dimensional matrix of tiles may be in powers of two when expressed in number of pixels of the light detector such as, for example, a 256 by 256 matrix, a 64×64 matrix, etc. Fourier camera system 100 iteratively "stitches" together the tile intensity images in Fourier space to recover a wide-field, complex tile image at the sample plane. In one example, a best focal plane may be determined for each complex tile image by propagating each complex tile image to multiple focal planes and determining which of the planes is the best focal plane. The tile image is then propagated to that determined best focal plane. The depth at the best focal plane for each tile is also determined. The Fourier camera system 100 may combine the focused tile images at different depths to generate a focused 3-D profile image of the sample surface and/or combines the tile images to generate a uniform resolution and focused 2-D image of the sample surface. In certain aspects, the tile images may be recovered in parallel.

In one embodiment, the illumination source(s) 110 may provide illumination at different wavelengths (RGB) and the Fourier camera system 100 may determine a focused 3-D profile image of a uniform resolution or a focused 2-D image for the different illumination wavelengths (RGB), and combine the images to generate a complex color image.

In certain aspects, a Fourier camera system comprises a processor(s) (e.g., 210) to execute instructions stored on one or more CRM (e.g., 220) to perform one or more functions of the acquisition process, recovery process, screening process, and output process of the Fourier camera system. In some cases, components of the Fourier camera system may comprise their own processor that executes instructions for performing functions of that component. For example, the light detector, variable aperture filter, and/or illumination source(s) may include one or more processors. In one example, a processor(s) of the variable aperture filter may execute instructions for generating an aperture at the plurality of aperture locations at the intermediate plane. As another example, a processor(s) of an illumination source(s) may execute instructions for generating illumination at particular sample times. As another example, a processor(s) of the light detector may execute instructions for sampling intensity distributions at different sample times. In some cases, the Fourier camera system may comprises a main processor(s) that provides control instructions to the different components of the Fourier camera system.

The Fourier camera system may also comprise a processor(s) for performing certain functions of the recovery process, screening process, and output process. For example, the processor(s) may execute instructions stored on the CRM to perform one or more of the following functions: 1) interpreting image data from the plurality of intensity images of the sample surface, 2) dividing up the intensity images into tile images, 3) recovering a complex image from the intensity tile images, 4) determining a best focal plane of each tile image, 5) determining a depth of each focal plane, 6) propagating each tile image to its best focal plane, 7) combining the complex images propagated to the best focal plane at the associated depth to determine a 3-D profile image, 8) combining the complex images propagated to the best focal plane to determine a 2-D profile image, 9) aligning the images to match the best curvatures and/or determining changes to an object of interest in the images of the sample surface, and 10) displaying one or more images or other output from the Fourier camera method on the display.

In certain aspects, a Fourier camera system comprises a CRM (e.g., memory) such as CRM 220 in FIG. 1. The CRM can store instructions for performing one or more functions of components of the Fourier camera system and/or store image data or other data related to the cycles. Such image data may comprise, for example, one or more of: intensity distributions taken at each sampling time during an acquisition process, combined focused, 2-D and 3-D images of the sample surface, images of the objects taken at different cycles, quantifiable comparisons between the object images between cycles, aperture locations during a particular cycle, and other related data to the processes performed by the Fourier camera system.

In certain aspects, a Fourier camera system comprises a display (e.g., display 230 in FIG. 1) in electronic communication with one or more processor(s) to receive data to output, for example, to an operator of the Fourier camera system. The display may be a color display or a black and white display. In addition, the display may be a two-dimensional display (i.e. device for displaying two-dimensional images) or a three-dimensional display (i.e. device for displaying three dimensional images). In one case, the display may be capable of displaying multiple views simultaneously.

For simplicity, the first and second optical systems of certain Fourier camera systems are described having the same focal length, f, in a 4f optical arrangement. It will be understood that the first optical system can have a different focal length than the second optical system. For example, the first optical system may have a first focal length of $f_1$ that is different that the second focal length $f_2$ of the second optical system. In this case, the sample plane is located at a distance of first focal length $f_1$ from the first optical system, the detector plane will be at a distance of the second focal length $f_2$ from the second optical system, and the Fourier plane will be at a distance of $f_1$ from the first optical system and a distance of $f_2$ from the second optical system.

In many aspects described herein, the aperture can be generated at a plurality of N aperture locations in a Fourier plane of the sample. However, it would be understood that the aperture could be generated in another intermediate plane conjugate to the sample such as, for example, the aperture plane of a compound lens system or the back-focal plane of an objective.

According to certain aspects, a Fourier camera system comprises a variable aperture filter configured to generate aperture(s) at N locations at different sample times in an intermediate plane of its optical arrangement. In many cases, the variable aperture filter generates a single aperture at the intermediate plane. In other cases the variable aperture filter may generate a plurality of apertures that are moved as a whole to different locations at the intermediate plane. The intermediate plane may be, for example, a Fourier plane conjugate the sample plane. Although a single aperture is typically generated by the variable aperture filter at a particular sample time, a plurality of apertures may be used in other cases. In these cases, the plurality of apertures is shifted as a whole to different locations at different sample times at the intermediate plane. Such a plurality of apertures may be in pattern form (e.g., checkered pattern) or in a random order.

An aperture generated by the variable aperture filter can refer to an area at the intermediate plane that allows light to pass to the next optical element in the optical arrangement while the area surrounding the aperture blocks/reflects or otherwise prevents light from passing. In certain aspects, the aperture may be an optically transparent or substantially optically transparent area. In these aspects, the surrounding area may reflect or absorb the incident light. For example, the aperture may be a light transmissive region (e.g., hole) in an opaque plate. In other aspects, the aperture may be a reflective area (e.g., one or more micromirrors or one or more reflective pixels in a display) that reflects incident light to the next optical element or a transmitted area (e.g., one or more transmissive elements) that transmits incident light to the next optical element. In these aspects, the surrounding area may either absorb incident light or reflect incident light away from the next optical element. In one example, the aperture may be comprised of one or more micromirrors oriented at an angle that reflects incident light to the next optical element. In this example, one or more micromirrors in the surrounding area may be oriented at a different angle that reflects light away from the next optical element. In some cases, an aperture location may correspond to a centroid of the area of the aperture.

Although apertures described with reference to certain examples are circular in shape having a diameter denoted as "l," other shapes such as a rectangular shape having dimensions of width l and height h, or a triangular shape, etc., may be used. In one case, the aperture is a circular shape having a diameter size of about 0.5 mm. In another case, the aperture is a circular shape having a diameter size of about 5 mm. In another case, the aperture is a circular shape having a diameter size in the range of about 0.5 mm to 5 mm.

The variable aperture filter of a Fourier camera system may be a display-based device or a mechanically-based device. A display-based variable aperture filter may digitally generate an aperture at different locations, for example, by displaying an aperture and surrounding area on a display. An example of a display-based variable aperture filter is a spatial light modulator (SLM) comprising an SLM display that can display the aperture(s) and surrounding area. A mechanically-based variable aperture filter which can mechanically shift an aperture to different aperture locations. For example, a mechanically-based variable aperture filter may comprise an X-Y translational stage that can translate/rotate a structure (e.g., plate of opaque material having an aperture in the form of a light transmissive region such as a hole in the plate) having the aperture to shift the aperture to the plurality of aperture locations in the intermediate plane.

In embodiments that have a variable aperture filter in the form of a spatial light modulator (SLM), the SLM may realize spatial modulation of a light field where the modulation includes attenuation (fully block or partially block the light) and phase change (retardation of light). In some cases, the SLM may use an electrical and/or optical signal from an SLM light source to modulate phase, $\varphi$, and/or amplitude of light. In some cases, the SLM light source may be a collimated light source such as a laser (e.g., Excelsior® 532 SLM). For example, a suitable laser source provides 532 nm quasi-monochromatic laser light, with spatial coherence length of multiple meters. In other cases, the SLM light source may not be collimated light. For example, the light may be spatially filtered light from a light emitting diode (spatial coherence length of approximately 1 mm, spectral bandwidth of 20 nm), or light from a laser source (e.g., 532 nm quasi-monochromatic laser light, spatial coherence length of multiple meters). Certain SLMs may be commercially available. In embodiments that have a SLM, the SLM can be digitally addressed to quickly shift a liquid-crystal based pupil function, which selectively blocks light depending upon which SLM display pixels are electronically triggered.

In certain aspects, an SLM display comprises SLM display elements. Each SLM display element can be set to function as an aperture or part of an aperture (aperture setting) or to function as the area surrounding the aperture (field setting). In transmitted SLM configurations, an SLM display element in an aperture setting is transparent or nearly transparent to pass incident light and a display element in a field setting may block/reflect or nearly bock/reflect incident light. In reflective SLM configurations, certain SLM display elements may be reflective. In these cases, a display element in the aperture setting is oriented at a (first) angle to reflect incident light to the next optical element in the optical arrangement and a display element in a field setting is oriented at a different (second) angle that reflects incident light away from the next optical element. In the both of these configurations, the SLM display can generate an aperture at one or more SLM display elements by setting these display elements in an aperture setting and/or setting the surrounding display elements in a field setting. At different sample times, $t_i$, different sets of one or more display elements are at appropriate settings to generate the aperture at the corresponding aperture location. In some cases, the SLM display may have a refresh rate in the range of 30 per second to 100 per second.

Figure 5:
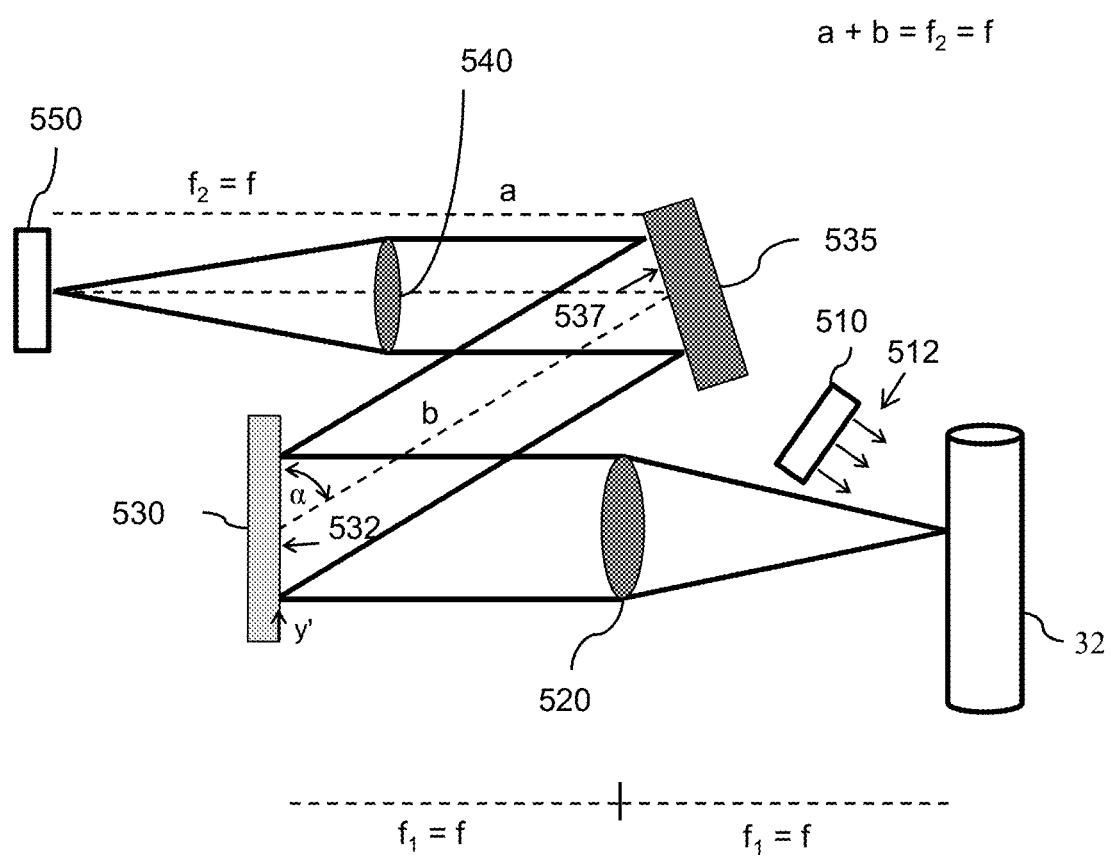
FIG. 5 is a schematic drawing of components of a Fourier camera system, according to an embodiment.
Figure 6:
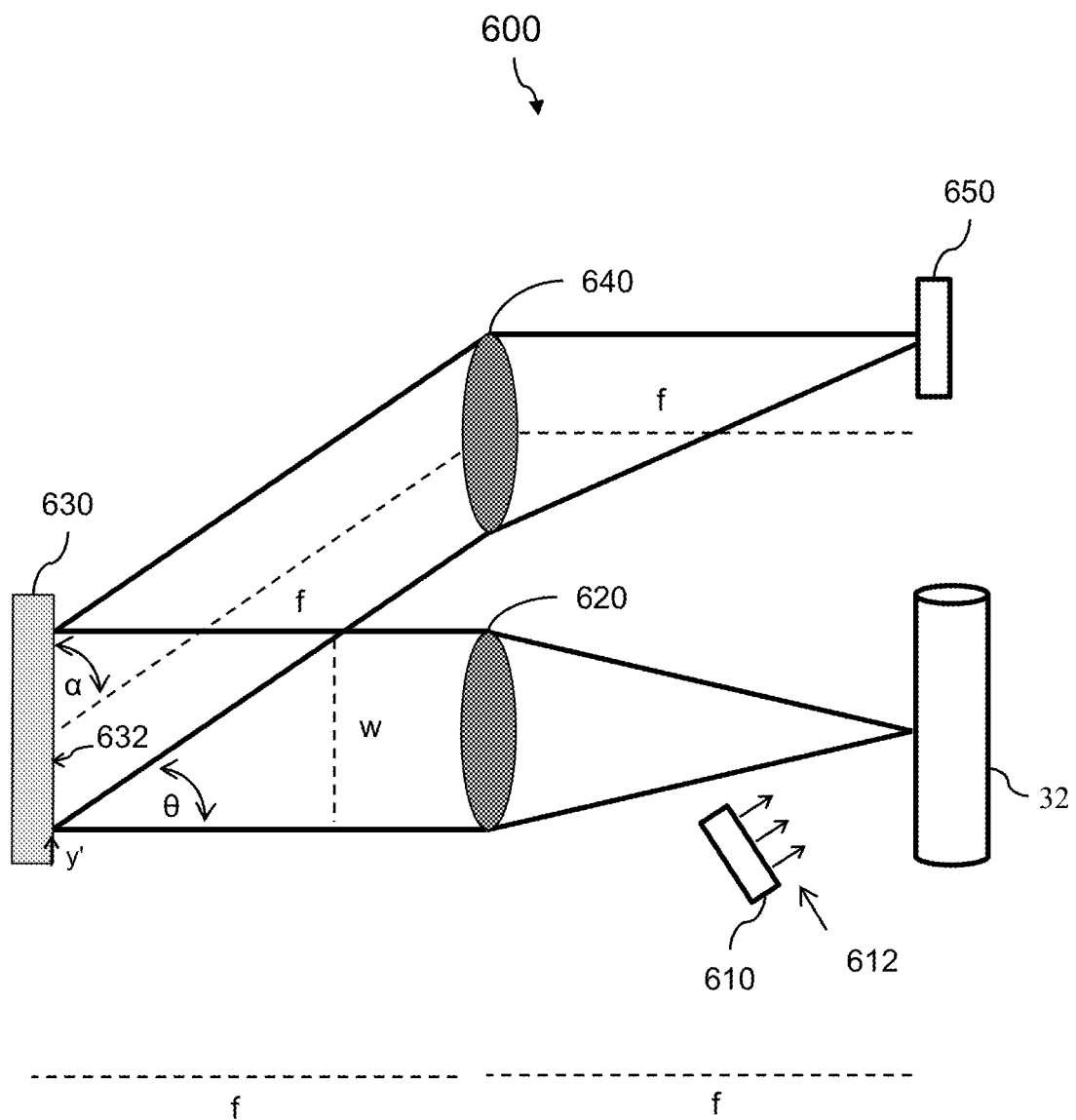
FIG. 6 is a schematic drawing of components of a Fourier camera system, according to an embodiment.

In Fourier camera systems comprising an variable aperture filter in the form of an SLM, different types of SLM displays may be used such as, for example, a reflective or transmitted liquid-crystal on silicon (LCoS) display, a digital micromirror device (DMD), etc. A liquid-crystal on silicon (LCoS) display is a display having a plurality of either reflective or transmitted display elements. An example of a commercially available LCoS display is the HOLOEYE® SLM, Pluto, phase only LCoS, 8 μm pixel size, 1080×1920 pixels display. A DMD can refer to an optical semiconductor chip having on its surface multiple microscopic micromirrors. In certain aspects, each micromirror can be individually rotated to an angle, $\alpha$. In this way, each micromirror can be transitioned to either an aperture setting at angle, α, or to a field setting at no rotation, or visa versa Although these micromirrors are usually arranged in a rectangular array (dimensions o×p), other arrangements may be used. In certain aspects, each micromirror of the DMD may correspond to one or more light detector pixels. In one case, one or more of the micromirrors in the aperture setting may be oriented so that an optical axis orthogonal to the surface of the micromirror is oriented at an angle, α, from the Fourier plane. An example of this case is shown in FIGS. 5 and 6.

In Fourier camera systems comprising a variable aperture filter in the form of an SLM, the SLM display may be located so that its display plane at the intermediate plane (e.g., Fourier plane). In some cases, the SLM display may be in the form of a two-dimensional matrix of SLM display elements (e.g. pixels) at the display plane. The two-dimensional matrix has dimensions of $Pix_1 \times Pix_2$, where $Pix_1$ is the number of pixels in a first direction and $Pix_2$ is the number of pixels in a second direction orthogonal to the first direction. In one example, the SLM display is a 1920-by-1080 pixel display where $Pix_1$ is 1920 and $Pix_2$ is 1080. In certain aspects, the display elements of the SLM are programmed to have particular settings at different sample times according to illumination instructions.

The plurality of N aperture locations may be described in the form of a one-dimensional array, a two-dimensional matrix, a hexagonal array, etc. In some cases, the plurality of aperture locations may be a two-dimensional matrix in the form of a rectilinear grid (e.g., square grid), a curvilinear grid, etc. If the plurality of N aperture locations is in a rectilinear grid arrangement having dimensions m×n, then the aperture locations may be designated as $(X_i, Y_j)$, i=1 to m, j=1 to n and the number of aperture locations, N=m×n. If such a rectilinear grid has square dimensions of n×n, then the aperture locations may be designated as $(X_i, Y_j)$, i=1 to n, j=1 to n and $N=n^2$.

The N aperture locations can be generated in any order (e.g., sequential, random, row by row, column by column, etc.) over time during the acquisition process. For example, a sequential column by column order through a rectilinear grid may be: $(X_1, Y_1), (X_1, Y_2), (X_1, Y_3), \ldots (X_1, Y_n), (X_2, Y_1), (X_1, Y_2), (X_1, Y_3), \ldots (X_2, Y_n), \ldots (X_m, Y_n)$ at sample times $t_i=1$ to M, where M=m×n. Alternatively, a random order may be used. The order, timing, and locations of the apertures being generated may be defined in controls instructions stored on and retrieved from the CRM. An example of a sequence of aperture locations in a particular cycle is provided on FIG. 4 where the apertures are displayed sequentially row by row in a rectangular grid.

Figure 4:
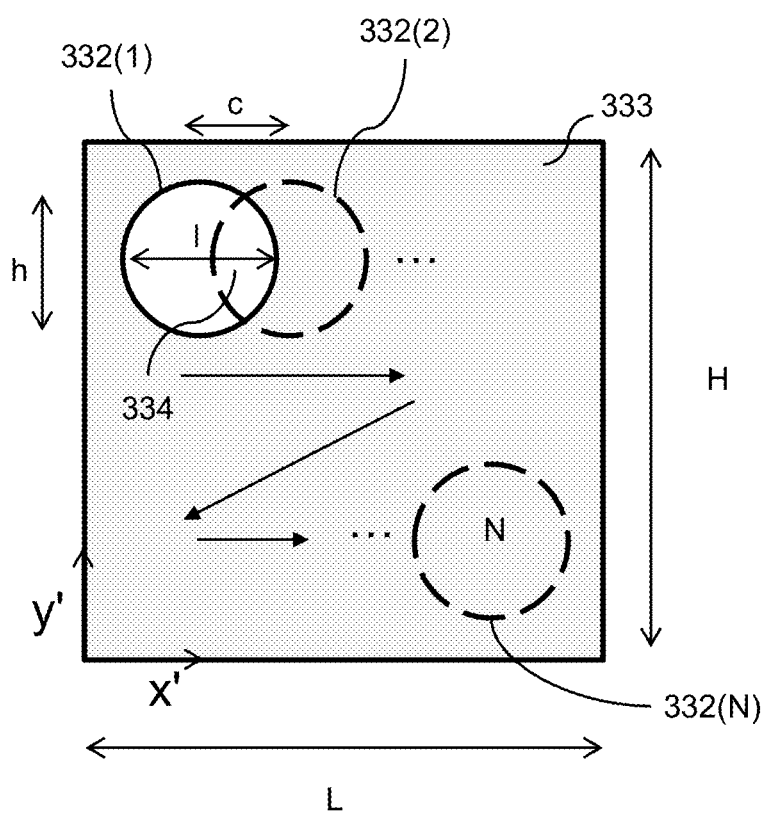
FIG. 4 is a schematic drawing of a front view of a display of the variable aperture filter, which is in the form of a spatial light modulator, of FIG. 3.

In certain aspects, the locations of the apertures are defined to have an overlapping area between neighboring apertures. For example, FIG. 4 shows an overlapping area 334 between aperture 332(1) and aperture 332(2). In one example, the overlapping area may be about 70% of the area of the apertures. In another example, the overlapping area may be about 75% of the area of the apertures. In another example, the overlapping area may be between about 20% and 90% of area of the apertures.

The Fourier camera system of embodiments comprises a light detector (e.g., 150) that receives light reflected by the sample surface and modulated by the aperture at different aperture locations in the intermediate plane. The light detector is configured to acquire a plurality of M (low resolution) intensity images corresponding to the N different aperture locations. The light detector acquires an intensity image of the sample surface by measuring/recording an intensity distribution of incident radiation at the detector plane at a particular sample (acquisition) time.

During an acquisition process, the light detector may acquire a plurality of M intensity images at M sample times, $t_{i=1 \; to \; M}$. In some cases, M=N so that the Fourier camera system acquires an intensity image at each aperture location. The Fourier camera system can synthesize multiple intensity images in the frequency domain to recover a complex, improved resolution image of tiled segments of the sample surface. The Fourier camera system can refocus the tiled images by propagating them to a best focal plane. The Fourier camera system can then combine these focused tiled images into a complex, improved resolution, and focused image of the sample surface.

In certain cases, each of the plurality of M intensity images acquired by the light detector corresponds to a different aperture location of the plurality of N aperture locations. The number of aperture locations N and/or number of intensity images M may be in the range of 1 to several thousand. In one case, N and/or M may be a value in a range from 1 to 1000. In another case, N and/or M may be a value in a range from 1 to 2000. In another case, N and/or M may be a value in a range from 1 to 3000. In some examples, N=M.

If radiation in the visible spectrum is being measured, the light detector may be in the form of a charge coupled device (CCD), a CMOS imaging sensor, an avalanche photo-diode (APD) array, a photo-diode (PD) array, a photomultiplier tube (PMT) array, or like device. These examples of light detectors and others are commercially available. In some cases, the light detector may be a color detector e.g., an RGB detector. In other cases, the light detector need not be a color detector. In certain cases, the light detector may be a monochromatic detector.

Certain Fourier camera systems described herein may be used for luminescence (e.g., fluorescence, phosphorescence, chemluminescence, bioluminescence, etc.) imaging applications. In luminescence imagin, fluorophores in the sample are excited by excitation illumination of a certain wavelength(s) from the illumination source and emit light of a different wavelength(s) (emissions). These emissions tend to have a weak signal compared to the excitation light so that collection efficiency may be important. By directing excitation illumination to the sample but away from the first optical system, the optical arrangement of the Fourier camera system can substantially avoid propagating excitation illumination through the system to the light detector and more efficiently collecting emissions at the light detector. In luminescence imaging, a reagent (e.g., fluorescence/phosphorescence dye) may be mixed with the sample to mark or tag portions under investigation with fluorophore. A fluorophore can refer to a component of a molecule that causes the molecule to fluoresce or phosphoresce. A fluorophore can absorb energy from excitation light of a specific wavelength(s) and re-emit the energy at a different wavelength(s). In luminescence imaging examples, the illumination source illuminates the sample with excitation light of predetermined wavelength(s) (e.g., blue light) to activate the fluorophore in the sample. In response, the fluorophore release emissions of a different wavelength(s) (e.g., red light).

A sample surface (e.g., skin) being imaged by a Fourier camera system of certain embodiments may comprise one or more objects of interest such as a mole. The sample may be a biological sample (e.g., arm, leg or other body part) or inorganic entity. The sample surface may have curvature in one or more directions. For example, the sample surface may be a skin surface of a limb or other body part such as an ear where the skin surface has curvature in one or more directions. In certain embodiments, the Fourier camera system can capture unfocused intensity images of the curved sample surface associated with different aperture locations and use these intensity images to recover a focused, high resolution, complex 2-D image of the curved sample surface and a focused, high resolution, 3D profile of the curved sample surface. In one example, the FPM camera system can be used to image multiple objects (e.g., 10, 20, 30, 40, 50, 100, etc.) on a sample surface. Although the imaged objects may be of different sizes, in one case the objects being imaged are at least 2 mm in diameter.

The Fourier camera system of embodiments comprises an illumination source(s) configured to provide illumination to the sample being imaged. The illumination source may be a component of or separate from the Fourier camera system. For example, an illumination source may be located within a housing with other components of the system. Although a single illumination source is described in many cases, it would be understood that multiple illumination sources may be used. In some cases, the Fourier camera system comprises an illumination source that illuminates the sample by a single arbitrarily patterned coherent illumination beam from a particular direction. Typically, the angle of illumination does not vary during the acquisition process. In some cases, the illumination may be monochromatic. In another case, the illumination source may provide illumination of different wavelengths (e.g., wavelengths associated with RGB) at different sample times as discussed below. Although the illumination source(s) may be coherent source(s), incoherent source(s) may also be used and computational corrections may be applied in the recovery process. Some examples of a discrete element of an illumination source providing visible light illumination include an LCD pixel and a pixel of an LED display. In color imaging applications, the illumination source may provide RGB illumination of three wavelengths $\lambda_1, \lambda_2,$ and $\lambda_3$ corresponding to red, green, blue colors, respectively.

As used herein, a sample time can refer to an instant in time that the light detector records an intensity distribution of incident light received at the light detector surface to acquire an intensity image. During acquisition processes of embodiments, the light detector captures a plurality of M intensity images. Generally, the aperture is at different aperture locations when the light detector captures different intensity images in this plurality of M intensity images. In certain Fourier camera methods, an intensity image may be acquired at each sample time designated as t where i=1 to M. The number of intensity images, M, acquired in an acquisition process of embodiments may be in the range of 2 to 10,000. M may have any suitable value such as, for example, 2, 5, 10, 20, 30, 50, 100, 1000, 10000, etc. The light detector has a sampling rate at which it samples intensity images. The sampling rate refers to the number of intensity images acquired per second. In certain cases, the sampling rate of the light detector may range from 0.1 to 1000 frames per second. As used herein, a frame can refer to a measured intensity distribution measured at a particular sample time.

In certain aspects, the light detector may have discrete light detecting elements such as, for example, pixels. Depending on the type of light detector used, the light detecting elements may be of various sizes such as, for example, sizes in the range of 1-10 microns. Also, the light detector elements may have different shapes (e.g., circular, rectangular, square, etc.). For example, in embodiments that use a CMOS or CCD, the light detecting elements may have a size in the range of 1 to 10 microns. As another example, in embodiments that use an APD or PMT, the light detecting elements may have a size in the range of 1 to 4 mm. In one embodiment, the light detector has light detecting elements that are square pixels having a size of about 5.5 μm.

In embodiments, a Fourier camera system generates and/or manipulates image data. For example, the light detector can generate image data of intensity distributions of incident light received at the detector surface at different sample times associated with different aperture locations. The Fourier camera system may also generate image data of complex, high resolution images based on these intensity distributions measured by the light detector. Image data may also comprise data related to the intensity distributions such as sample times and other related data. Image data may be communicated in signal(s) to various components of the Fourier camera system.

Fourier space can refer to a mathematical space spanned by wavevectors $k_x$ and $k_y$, being the coordinate space in which the two-dimensional Fourier transforms of the spatial images created by the Fourier camera system reside. Fourier space may also refer to the mathematical space spanned by wavevectors $k_x$ and $k_y$ in which the two-dimensional Fourier transforms of the spatial images collected by the light detector reside.

Each of the plurality of M intensity images captured by the light detector as modulated by a particular aperture location is associated with a different region in Fourier space. In Fourier space, each of the different regions corresponds to apertures at different locations provided by the variable aperture filter. In Fourier space, neighboring regions may share an overlapping area over which they sample the same Fourier domain data. This overlapping area in Fourier space corresponds to the overlapping area of neighboring apertures at the intermediate plane of the Fourier camera system. In certain aspects, the plurality of N aperture locations may be designed so that the overlapping area of neighboring aperture locations will generate a certain amount of overlapping area in the Fourier domain data. In one aspect, the plurality of aperture locations are designed to generate an overlapping area in the Fourier domain data in the range of about 2% to about 99.5% of the area of one of the regions in the Fourier domain. In another aspect, the overlapping area between neighboring regions may have an area that is in the range of 65% to 75% the area of one of the regions in the Fourier domain. In another aspect, the overlapping area between neighboring regions may have an area that is about 65% of the area of one of the regions in the Fourier domain. In another aspect, the overlapping area between neighboring regions may have an area that is about 70% of the area of one of the regions in the Fourier domain. In another aspect, the overlapping area between neighboring regions may have an area that is at least about 70% of the area of one of the regions in the Fourier domain.

During certain acquisition processes, the variable aperture filter of a Fourier camera system generates an aperture at a plurality of N aperture locations, for example, at spatial coordinates of $(X_i, Y_j)$, i=1 to n,j=1 to m, M=n×m. At neighboring aperture locations in the plurality of aperture locations there is an overlapping region (e.g., 334 in FIG. 4) between neighboring aperture locations. At the detector plane, the light detector may be configured to acquire an intensity image while the aperture is at a particular aperture position. During the acquisition process, the light detector acquires a plurality of M intensity images corresponding to different aperture locations. The M intensity images (e.g., intensity images designated as $I_{i,j}$, i=1 to, o,j=1 top and M=oxp) are acquired at the detector plane at sample times, $t_{i,j}$, i=1 to o, j=1 top. During certain image recovery processes, a Fourier camera system divides each of the intensity images into tiles and recovers a higher resolution, complex field $E_l(x, y)$ at the sample plane of each tile from the plurality of M intensity tile images. In certain aspects, the complex field at the sample plane can then be propagated to various planes (e.g., planes parallel to the sample plane). The best focal plane can be determined from the images at the various planes. The propagated tile images at their corresponding best focal planes and the associated depths of those best focal planes can be used to form a 3D profile image of a sample surface.

Details of certain acquisition and recovery processes can be found in Section II below. An example of a recovery process can be used by the Fourier camera system can be found in Guoan Zheng, Roarke Horstmeyer, and Changhuei Yang, "Wide-field, high-resolution Fourier ptychographic microscopy," Nature Photonics 6, pp. 739-745 (2013), which is hereby incorporated by reference in its entirety. Certain details of a Fourier camera system can be found in Dong, Siyuan et al., "Aperture-scanning Fourier ptychography for 3D refocusing and super-resolution macroscopic imaging," pp. 13586-13599 (Jun. 2, 2014), which is hereby incorporated by reference in its entirety.

Figure 2:
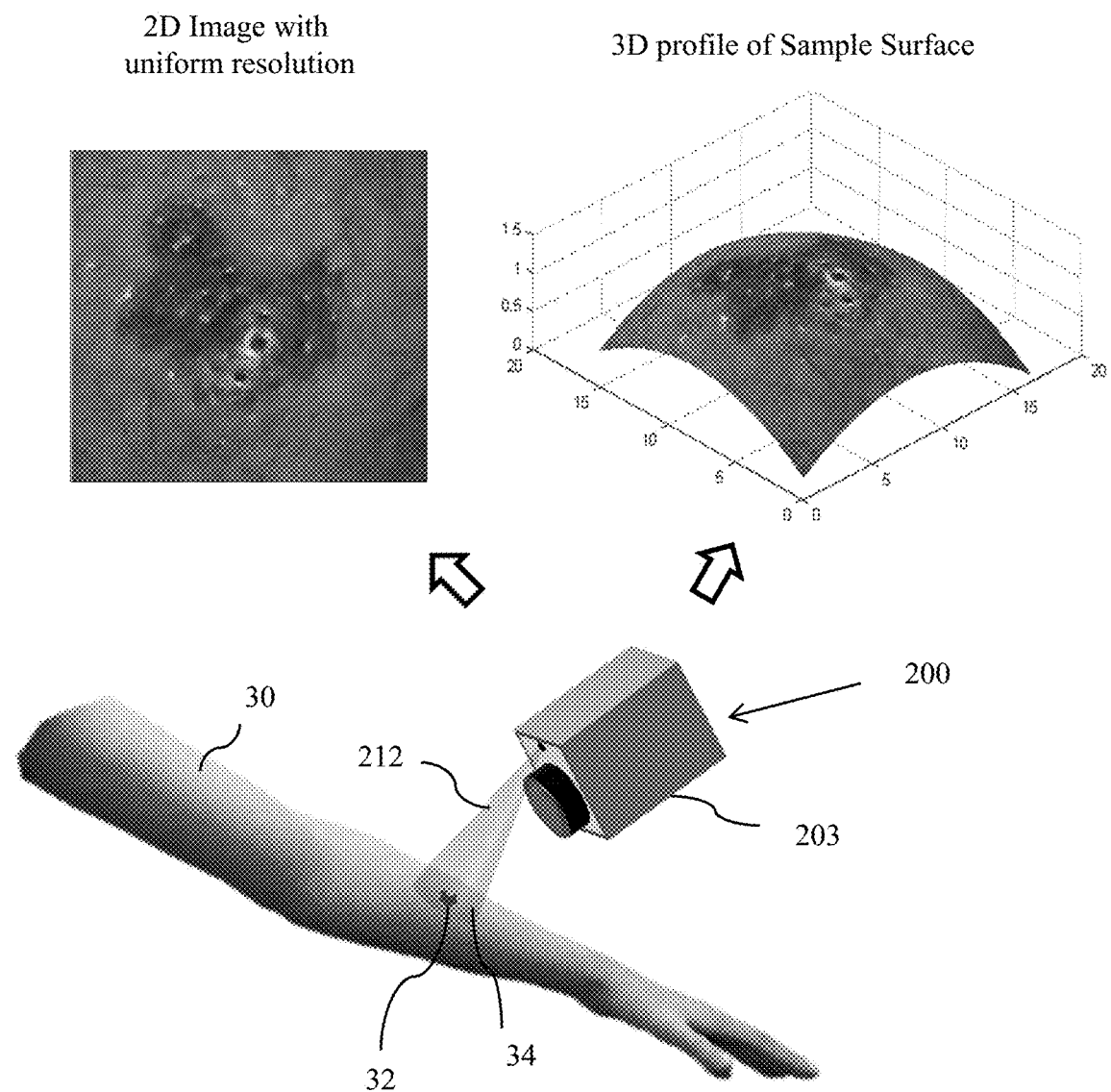
FIG. 2 is a schematic drawing of a Fourier camera system and generated 2-D and 3-profile images with at least substantially uniform resolution over a curved sample surface, according to embodiments.

FIG. 2 is a schematic drawing of a Fourier camera system 200 shown in operation during an acquisition process of an image of a sample 30, according to embodiments. In some embodiments, components of the Fourier camera system 200 may be similar to components of the Fourier camera system 100 shown with respect to FIG. 1.

In FIG. 2, the sample 30 is depicted as an arm. Other samples may be used as well. In the illustration, the Fourier camera system 200 is shown providing illumination 212 to a sample surface 34 having an object 32 being imaged. The Fourier camera system 200 comprises a housing 203, which is shown in this example as having a rectangular shape. In this example, the housing 203 is designed to be held in position during the acquisition process by a human hand similar to as would be done with a conventional camera. It would be understood that other shapes of housings may be used. In this example, the housing includes an aperture through which illumination 212 is passed and the illumination source (not shown) is located within the housing 203.

As depicted by the arrows to the two images at the top portion of FIG. 2, Fourier camera system 200 can be used to generate a 2-D image and/or a 3D profile with uniform resolution (i.e. all regions in focus) or substantially uniform resolution over the sample surface 34. In this case, the Fourier camera system 200 is used to capture both a 2-D image and a 3D profile image with uniform resolution of a mole on an arm.

Figure 3:
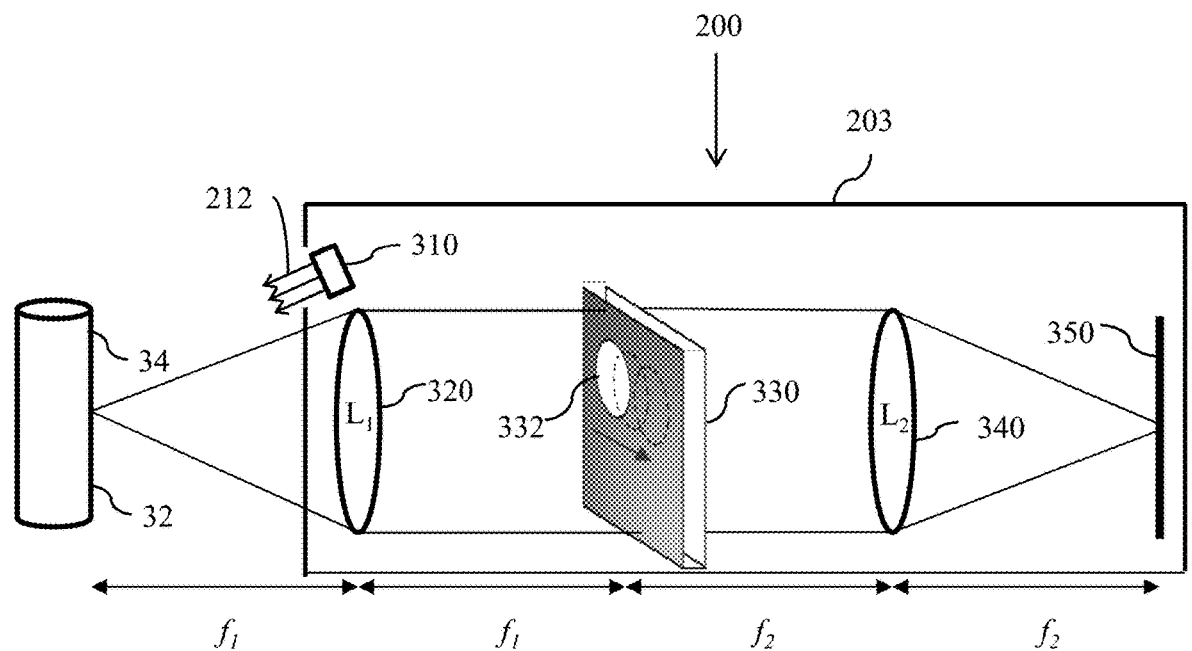
FIG. 3 is a schematic drawing of components of the Fourier camera system of FIG. 2.

There may be similarities between certain components of Fourier camera system 100 in FIG. 1, and the components of Fourier camera system 200 in FIGS. 2 and 3.

FIG. 3 is a schematic drawing of components of Fourier camera system 200 shown in FIG. 2, according to embodiments. Fourier camera system 200 is shown in operation during an acquisition process of an image of a sample surface 34 of a sample 32. The Fourier camera system 200 comprises an illumination source 310 configured to provide illumination 212 to a sample surface 34 of a sample 32. The illumination source 310 may provide a single arbitrarily patterned coherent illumination beam.

The Fourier camera system 200 further comprises a first optical system (e.g., lens) 320 having a first focal length $f_1$ (where $f_1=f$), a variable aperture filter 330 having an aperture 332, and a second optical system (e.g., lens) 340 having a second focal length $f_2$ (where $f_1=f$). Variable aperture filter 330 is configured to provide an aperture 332 to a plurality of N locations at a Fourier plane of the sample 32. Variable aperture filter 330 is in the form of a spatial light modulator (SLM) in the illustrated example. In other examples, such as those shown in FIGS. 5-7, other types of variable aperture filters may be used. Certain details of using a spatial light modulator for shifting a aperture at a display plane can be found in Horstmeyer, Roarke et al., "Overlapped Fourier coding for optical aberration removal," (2014), which is hereby incorporated by reference in its entirety.

The Fourier camera system 200 further comprises a light detector 350 with a (active) detecting surface at a detector plane. In FIG. 3, the Fourier camera system 200 is in a 4f optical arrangement with the first optical system 320 located at a distance from the second optical system 340 equal to their combined focal lengths 2f The sample 32 is located at a first focal length ($f_1=f$) from the first optical system 320 and the detector plane of the detector 350 is located at an optical path distance of the second focal length (where $f_2=f$) from the second optical system 340. The Fourier plane of the sample is located at an optical path distance of the first focal length (where $f_1=f$) of the first optical system 320 away from the first optical system 320 and located at an optical path distance of the second focal length (where $f_2=f$) of the second optical system 340 away from the second optical system 340.

Although not illustrated, Fourier camera system 200 may further comprise a processor, a display, a computer readable medium, and other components of a computing device. These components may be located within or external to the housing 203 of FIG. 2.

FIG. 4 is a schematic drawing of a front view of a display 333 of the variable aperture filter 330, which is in the form of a spatial light modulator, of FIG. 3. FIG. 4 includes an x'-axis and a y'-axis at the display plane. The display 333 is a rectangular display with dimensions of width L and height H. The variable aperture filter 330 may be configured (e.g., programmed) to digitally generate an aperture on its display 333 at a plurality of N locations. In this illustrated example, the plurality of N aperture locations is in the form of a square grid (n×n dimensions) with equally-spaced locations (i.e. equal spacing between neighboring apertures). In other cases, the spacing between neighboring aperture locations may not be equally spaced and/or the aperture may have different sizes at different locations. In square arrangements of aperture locations, the N aperture locations can be may be described as $(X_i, Y_j)$, i=1 to n, j=1 to n, in the display plane and the number of aperture locations is $N=n^2$.

In FIG. 4, the display 333 is shown at acquisition (sample) time, $t_1$, when an aperture 332(1) (shown in sold line) is generated on the display 333. The illustration also includes a neighboring aperture 332(2) (shown in dotted line) that is displayed at another sample time (e.g., $t_2$) in the sequence of sample times, as denoted by a dotted line to illustrate the spatial overlapping relationship between the neighboring apertures. As shown, neighboring apertures 332(1) and 332(2) have an overlapping region 334. The distance between the aperture location is distance, c, in the x'-direction. The illustration also includes a last aperture 332(N) in the sequence of apertures displayed at the last sample time $t_N$ in the sequence of N sample times. In the illustrated square arrangement of apertures, the total number of apertures in the sequence is $N=n^2$. In one aspect, the overlapping region may have an area of at least about 70% of the area of the aperture. In one aspect, the overlapping region may have an area of at least about 75% of the area of the aperture 332.

In one aspect, the overlapping region may have an area of at least about 20-90% of the area of the aperture 332. In one aspect, the distance between the neighboring (adjacent) apertures locations may provide n>L/l. For example, if n=9, setting L/l=2.5 will generate an overlapping region having an area of more than 75% of the area of an aperture.

In FIG. 4, apertures 332(1), 332(2), and 332(N) have a constant circular shape with a diameter l. In other embodiments, the apertures may have different sizes and/or shapes (e.g., rectangular). Display control instructions may be used by variable aperture filter 330 to generate an aperture on the display 333. The control instructions may be provided by a processor and/or stored on a computer readable medium of the Fourier camera system 200.

Figure 7:
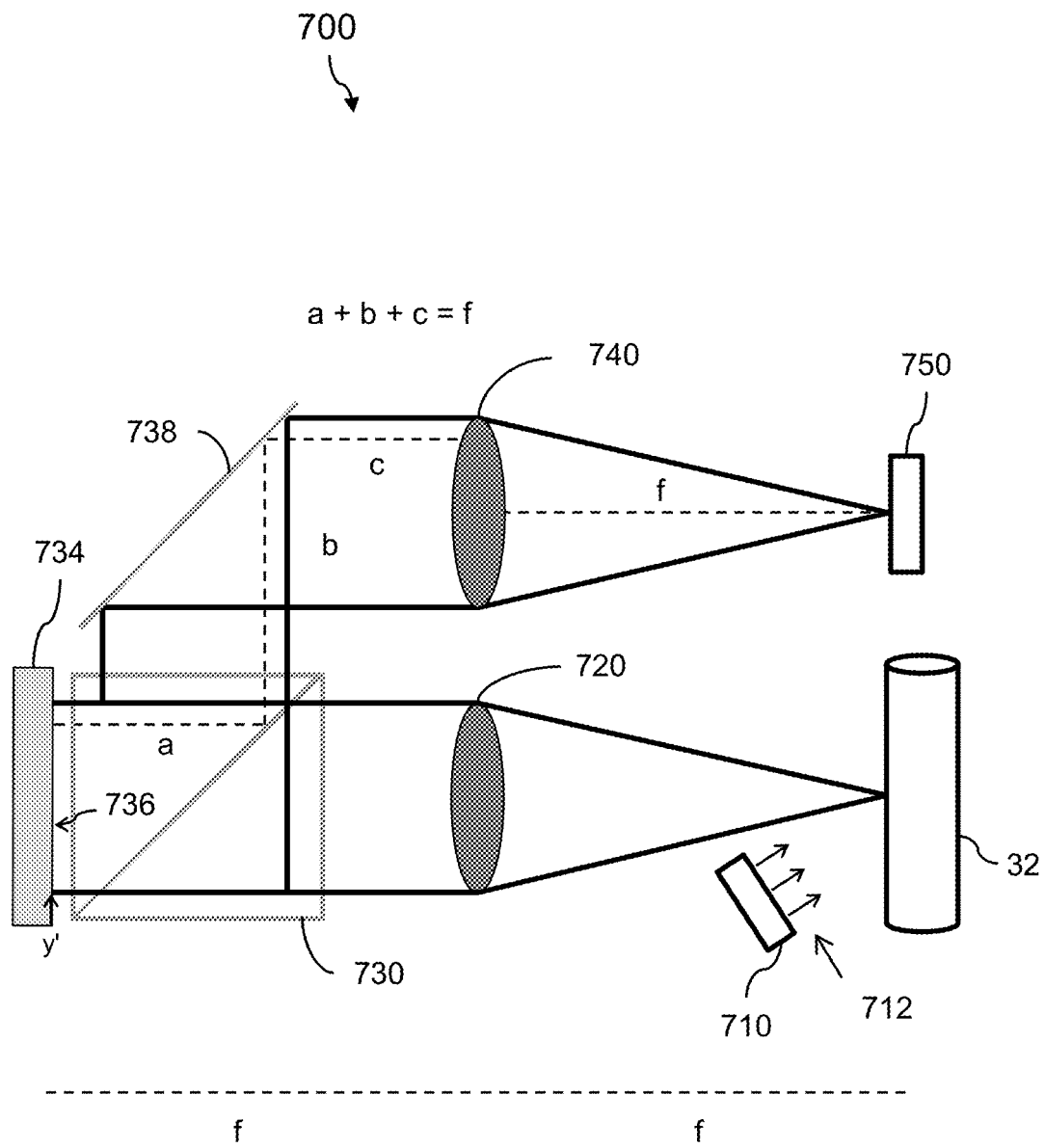
FIG. 7 is a schematic drawing of components of a Fourier camera system, according to an embodiment.

FIGS. 5-7 are schematic drawings illustrating three examples of configurations of components of Fourier camera system 200 described with reference to FIG. 3.

FIG. 5 is a schematic drawing of components of a Fourier camera system 500, according to an embodiment. Fourier camera system 500 comprises a first optical system (e.g., objective lens) 520, a variable aperture filter comprising a DMD array 530 having a display surface 532 and a sequence of one or more mirrors 535 having a reflective surface 537, a second optical system (e.g., objective lens) 540, and a light detector 550. First optical system 520 is shown as having a first focal length $f_1=f$. Second optical system 540 is shown as having a second focal length $f_2=f$. The display surface 532 of the DMD array 530 includes a y'-axis and an x'-axis (not shown) orthogonal to the y'-axis, both in the plane at the display surface 532. A sample 32 is shown at a sample plane of the Fourier camera system 500 during operation of an acquisition process.

In FIG. 5, Fourier camera system 500 comprises an illumination source 510 configured to provide illumination 512. In other examples, illumination source 510 may be a separate component. Although a single illumination source 510 is shown in this example, multiple illumination sources may be used. In this configuration, illumination source 510 is configured to illuminate the sample surface so that incident light reflected from the sample surface is directed back to first optical system 520. This configuration also directs illumination 512 from the illumination source 510 away from first optical system 520. This configuration is also suitable for receiving emissions from the sample 32.

The Fourier camera system 500 has a 4f optical arrangement with the first optical system 520 located at an optical path distance from the second optical system 540 equal to their combined first and second focal lengths 2f. The sample plane is located at an optical path distance of the first focal length $f_1=f$ from the first optical system 520. In this 4f arrangement, the detector plane is located at an optical path length of the second focal length $f_2=f$ from the second optical system 540. The DMD array 530 is located at an optical path length of the first focal length $f_1=f$ away from the first optical system 520. The sequence of one or more mirrors 535 is located at an optical path length, b, from the DMD array 530 and at an optical path length, a, from the second optical system 540. The combined optical path distance between the DMD array 530 and the second optical system 540 is a+b=f. The Fourier plane of the sample is located at an optical path length of the first focal length $f_1=f$ of the first optical system 520 away from the first optical system 520 and located at a combined optical path length a+b=f from the second optical system 540. In FIG. 5, a sample 32 being imaged is shown located at the sample plane, the light detector 550 is located so that the active detecting surface is at a detector plane, and DMD array 530 is located so that the display surface 532 is at the Fourier plane associated with the sample plane of the sample 32.

The DMD array 530 is configured to provide an aperture at a plurality of N aperture locations at the Fourier plane of the sample 32 at different sample times. The DMD array 530 comprises a plurality of micromirrors. At each sample time, DMD array 530 generates an aperture at particular aperture location at display surface 532 by rotating a set of one or more micromirrors of the DMD array 530 to reflect incident light at an angle, α, directed to the one or more mirrors 535. The set of one or more micromirrors corresponds to the aperture location. In some cases, other micromirrors surrounding the set of micromirrors are oriented at an angle that reflects incident light away from the one or more mirrors 535.

In FIG. 5, the one or more mirrors 535 are configured to receive light reflected by the aperture generated by the DMD array 530 to second optical system 540. In some aspects, the sequence of one or more mirrors 535 may be configured to correct the differences in optical path length at the different locations along the y'-axis to the surface of the mirrors 535. The illustration indicates an optical path b of a center ray between the surface 532 of the DMD array 530 and the surface 532 of the mirror(s) 535 and the optical path length a between the mirror(s) 535 and the second optical system 540. The combined optical path of the center ray between first optical system 520 and the second optical system is a+b=f. However, the optical path distance between the sequence of mirrors 535 and the DMD array 530 is not the same from edge to edge of these devices. To correct these differences, the sequence of one or more mirrors 535 may have locations and/or orientations that correct for these differences. For example, a binary grating pattern (i.e., a blazed grating) may be super-imposed on top of the sub-aperture pattern displayed on the DMD array 530. Alternatively, an algorithm similar to the simulated annealing correction approach discussed in Horstmeyer, Roarke et al., "Overlapped Fourier coding for optical aberration removal," (2014) may be used to find an arbitrarily-shaped pattern of mirrors to offer optimized correction performance. This reference is hereby incorporated by reference in its entirety for details of this approach.

Although not shown, Fourier camera system 500 may also include one or more components of a computing device, which comprises a processor, a display in electrical communication with the processor, and a computer readable medium in electrical communication with the processor. Components of Fourier camera system 500 may be similar to components of other Fourier camera systems. For example, first optical system 520 and second optical system (e.g., objective lens) 540 may be similar to first optical system 320 and second optical system 340 described with respect to FIG. 3. As another example, illumination source 510 may be similar to illumination source 310 described with respect to FIG. 3. As another example, light detector 550 may be similar to light detector 350 described with respect to FIG. 3.

FIG. 6 is a schematic drawing of components of a Fourier camera system 600, according to an embodiment. Fourier camera system 600 comprises a first optical system (e.g., objective lens) 620 having a first focal length $f_1=f$, a second optical system (e.g., lens) 640 having a second focal length $f_2=f$, and a light detector 650. Fourier camera system 600 further comprises a variable aperture filter in the form of a DMD array 630 having a display surface 632. The display surface 632 includes a y'-axis and an x'-axis (not shown) orthogonal to the y'-axis, both in the plane at the surface 632.

In the illustration, a sample 32 is shown at a sample plane of the Fourier camera system 600 during operation of an acquisition process.

Fourier camera system 600 comprises an illumination source 610 configured to provide illumination 612. In other examples, illumination source 610 may be a separate component. Although a single illumination source 610 is shown in this example, multiple illumination sources may be used. In this configuration, illumination source 610 is configured to illuminate the sample surface so that incident light reflected from the sample surface is directed back to first optical system 620. This configuration also directs illumination 612 from the illumination source 610 away from first optical system 620. This configuration is also suitable for receiving emissions from the sample 32. In one aspect, illumination source 710 may provide a single arbitrarily patterned coherent illumination beam from any selected direction.

In the illustrated example, an angle, θ, between the center ray optical paths between first optical system 620 and the DMD array 630 and the second optical system 640 and the DMD array 630 is small angle. Since the angle, θ, is small in this configuration, the optical path distances for these center rays can be approximated as parallel and of equal distances. In one aspect, the angle, θ, may be between about 1 degree and about 10 degrees. In another aspect, the angle, θ, is about 10 degrees. In another aspect, the angle, θ, is about 15 degrees.

With this above-discussed approximation, Fourier camera system 600 may be approximated as a 4f optical arrangement with first optical system 620 located at an optical path distance from second optical system 640 that is approximated as equal to the combined first and second focal lengths 2f. The sample plane is located at the first focal length $f_1=f$ from the first optical system 620 and the detector plane is located at the second focal length $f_2=f$ from the second optical system 640. The Fourier plane of the sample is located at an optical path length of the first focal length $f_1=f$ of the first optical system 620 away from the first optical system 620 and located at an optical path length of approximately the second focal length $f_2=f$ of the second optical system 640 away from the second optical system 640.

In FIG. 6, a sample 32 being imaged is shown located at the sample plane and the light detector 650 is located so that the active detecting surface is approximately at the detector plane. The DMD array 630 is located at an optical path length of the first focal length $f_1=f$ away from the first optical system 620 and located at an optical path length of approximately the second focal second focal length $f_2=f$ from the second optical system 640.

The DMD array 630 is configured to provide an aperture at a plurality of N aperture locations at the Fourier plane of the sample 32 at different sample times. The DMD array 630 comprises a plurality of micromirrors. At each sample time, DMD array 630 generates an aperture at particular aperture location at display surface 632 by rotating a set of one or more micromirrors of the DMD array 630 to reflect incident light at an angle, α, directed to the one or more mirrors 635. The set of one or more micromirrors corresponds to the aperture location. In some cases, other micromirrors surrounding the set of micromirrors are oriented at an angle that reflects incident light away from the one or more mirrors 635.

Although not shown, Fourier camera system 600 may also include one or more components of a computing device, which comprises a processor, a display in electrical communication with the processor, and a computer readable medium in electrical communication with the processor. Components of Fourier camera system 600 may be similar to components of other Fourier camera systems. For example, first optical system 620 and second optical system (e.g., objective lens) 640 may be similar to first optical system 620 and second optical system 640 described with respect to FIG. 3. As another example, illumination source 610 may be similar to illumination source 610 described with respect to FIG. 3. As another example, light detector 650 may be similar to light detector 650 described with respect to FIG. 3.

FIG. 7 is a schematic drawing of a view of components of a Fourier camera system 700, according to an embodiment. Fourier camera system 700 comprises a first optical system (e.g., objective lens) 720, a variable aperture filter, a second optical system (e.g., objective lens) 740, and a light detector 750. First optical system (e.g., objective lens) 720 is shown as having a first focal length $f_1=f$. Second optical system (e.g., lens) 740 is shown as having a second focal length $f_2=f$. In this example, the variable aperture filter comprises a beam splitter 730, a LCOS array 734 having a display surface 736, and a mirror 738. The surface 736 includes a y'-axis and an x'-axis (not shown) that is orthogonal to the y'-axis.

Fourier camera system 700 comprises an illumination source 710 configured to provide illumination 712. In other examples, illumination source 710 may be a separate component. Although a single illumination source 710 is shown in this example, multiple illumination sources may be used. In this configuration, illumination source 710 is configured to illuminate the sample surface so that incident light reflected from the sample surface is directed back to first optical system 720. This configuration also directs illumination 712 from the illumination source 710 away from first optical system 720. This configuration is also suitable for receiving emissions from the sample 32.

Fourier camera system 700 is in a 4f optical arrangement with the first optical system 720 located at an optical path distance from the second optical system 740 equal to their combined first and second focal lengths 2f. The sample plane is located at an optical path distance of the first focal length $f_1=f$ from the first optical system 720. In this 4f arrangement, the detector plane is located at an optical path length of the second focal length $f_2=f$ from the second optical system 740. The LCOS array 734 is located at an optical path length of the first focal length $f_1=f$ away from the first optical system 720.

The beam splitter 730 is configured to pass incident light of first wavelength(s) received from the first optical system 720 and to absorb/reflect incident light of second wavelength(s) received from the first optical system 720. For example, the beam splitter 730 may be configured to pass incident light of wavelengths associated with emissions from fluorophore in a sample illuminated by excitation illumination in a fluorescent imaging application. The beam splitter 730 is further configured to absorb incident light of the second wavelength(s) received from the LCOS array 734, and reflect incident light of the first wavelength(s) received from the LCOS array 734 to the mirror 738. Alternatively, a conventional beam splitter may be used with the addition of a spectral filter placed anywhere in the optical path between the sample and the detector, which can pass light of wavelengths associated with emissions from fluorophore and absorb excitation illumination in a fluorescent imaging application.

In FIG. 7, the optical path distance between the LCOS array 734 and the beam splitter 730 is designated as, a. The optical path distance between the beam splitter 730 and the mirror 738 is b. The optical path distance between the mirror 738 and the second optical system 740 is c. The combined optical path distance between the LCOS array 734 and the second optical system 740 is a+b+c=f. The Fourier plane of the sample in this optical arrangement is at an optical path length of the first focal length $f_1$=f from the first optical system 720 and located at a combined optical path length a+b+c=f from the second optical system 740. In FIG. 4, a sample 32 being imaged is shown located at the sample plane, the detector 750 is located so that the active detecting surface is at the detector plane, and display surface 736 of the LCOS array 734 is located at the Fourier plane associated with the sample plane.

Advantages of this configuration may be that the optical path is of equal length between the first and second optical systems 720 and 740 and that the optical elements do not need to be placed at challenging angles.

The LCOS array 734 is configured to provide an aperture at a plurality of N aperture locations at an intermediate plane, which in this case is the Fourier plane associated with the sample plane. The LCOS array 734 comprises display comprised of a plurality of display elements that can be set to be reflective. The LCOS array 734 generates an aperture at each aperture location at the display surface by setting one or more display elements to be reflective in order to reflect incident light back to the beam splitter 730. In some cases, the surrounding elements are set to be substantially transmissive or absorptive.

Although not shown, Fourier camera system 700 may also include one or more components of a computing device, which comprises a processor, a display in electrical communication with the processor, and a computer readable medium in electrical communication with the processor. Components of Fourier camera system 700 may be similar to components of other Fourier camera systems. For example, first optical system 720 and second optical system (e.g., objective lens) 740 may be similar to first optical system 720 and second optical system 740 described with respect to FIG. 3. As another example, illumination source 710 may be similar to illumination source 710 described with respect to FIG. 3. As another example, light detector 750 may be similar to light detector 750 described with respect to FIG. 3.

Modifications, additions, or omissions may be made to any of the Fourier camera systems of embodiments without departing from the scope of the disclosure. In addition, the components of a Fourier camera system may be integrated or separated according to particular needs. For example, processors(s) may be integrated into one or more of the components of the Fourier camera system.

II. Fourier Camera Methods

Fourier camera methods generally comprise an acquisition process, a recovery process, screening process, and an optional display process. During an exemplary acquisition process, M intensity (lower resolution) images of the sample surface corresponding to different aperture locations are acquired. During an exemplary recovery process, each of the M intensity images is divided into tile images, the M intensity tile images are iteratively stitched together in overlapping regions in Fourier space to recover a complex and higher resolution image of the tile, each complex tile image is propagated to a best focal plane, and the focused and higher resolution tile images are combined to generate a substantially uniform resolution image of the sample surface. In some cases, the best focal plane for each tile is determined by propagating each complex tile image to multiple focal planes and determining which of the focal planes is the best focal plane. During this exemplary recovery process, each tile is focused individually so that an entire curved sample surface can be uniformly focused and have a uniform resolution. Using this exemplary recovery process, unfocused intensity raw (low resolution) images of a curved surface can be used to generate a focused and higher resolution image of the curved surface. During an exemplary screening process, the higher resolution images of the sample surface taken at different imaging cycles may be aligned to be able to compare the images. For example, images of an object (e.g., mole) on the sample surface may be aligned and compared to determine changes in the object over time. During an exemplary output process, the recovered images of the sample surface, results from a comparison of the images over multiple cycles, and other output may be generated on a display or other output device. In certain aspects, a Fourier camera system may perform one or more cycles to image the sample surface, for example, during different visits to a melanoma screening clinic. Although the Fourier camera methods described in this Section are described with respect to the Fourier camera system with an SLM of FIG. 3, other embodiments of a Fourier camera system can be used. One or more steps of these methods may be performed by a processor(s) of the Fourier camera system.

Figure 8:
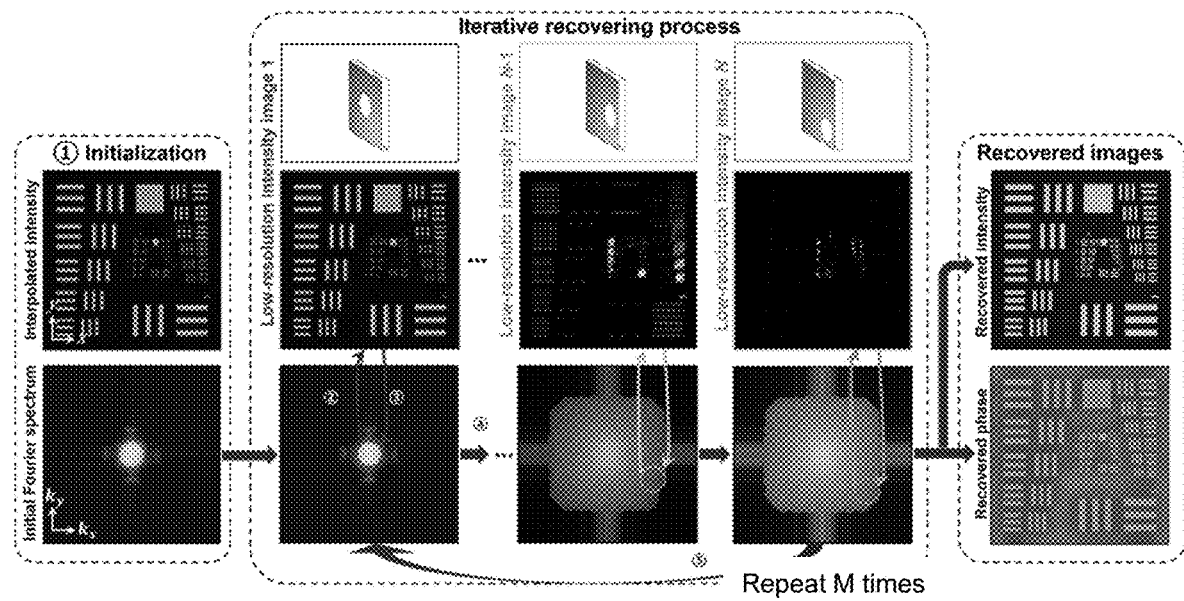
FIG. 8 is a diagram depicting steps of a phase retrieval technique that can be used as part of a Fourier camera method to reconstruct the intensity and phase information of the sample, according to embodiments.

In certain aspects, a recovery process of a Fourier camera method comprises phase retrieval technique to reconstruct intensity and phase information of light reflected from a sample surface. FIG. 8 is a diagram depicting steps of a phase retrieval technique that can be used as part of a Fourier camera method to reconstruct the intensity and phase information of the sample, according to embodiments. Using this phase retrieval technique, both amplitude and phase variations of light reflected from a sample surface can be determined. Once both amplitude and phase variations are determined, the Fourier camera method can use this information to propagate the light field wavefront forward or backwards to sharpen image focus, accurately stitch together different overlapping images in the Fourier domain to enhance resolution, and/or measure the distance from the Fourier camera system to any point on the sample surface.

Returning to the diagram in FIG. 8, the phase retrieval technique extracts phase information from a sequence of raw intensity images. In an "Initialization" step, the phase retrieval technique projects an initial guess of the light's phase onto a series of known constraints. In an "Iterative Recovery" step, the initial guess is led to converge to an accurate phase solution. The constraints are in the signal's Fourier domain, which corresponds to the light's wavefront at the SLM plane. Each SLM pupil function displayed by the Fourier camera during image capture (acquisition) corresponds to a unique constraint on this wavefront at the SLM plane. By selecting pupil functions that overlap (i.e., overlapping apertures), the constraints being applied may more rapidly and accurately converge. The "Iterative Recovery" process results in recovering both intensity and phase images as illustrated. An example of certain details of an exemplary phase retrieval technique used by a Fourier camera system is described with respect to FIG. 10.

In certain aspects, the image of the sample surface is split into smaller tiles before implementing the phase retrieval technique on each tile. Having determined each tile's amplitude and phase distribution, the light field wavefront can be propagated forward and backwards, for example, to achieve the sharpest image acuity and thereby find the corresponding tile's correct (best) focal plane. This computation also yields an accurate measure of the distance from the camera to the tile. These distance measurements for the tiles along with the focused tile images may be composed and rendered into a topological plot of the entire sample surface.

Figure 9:
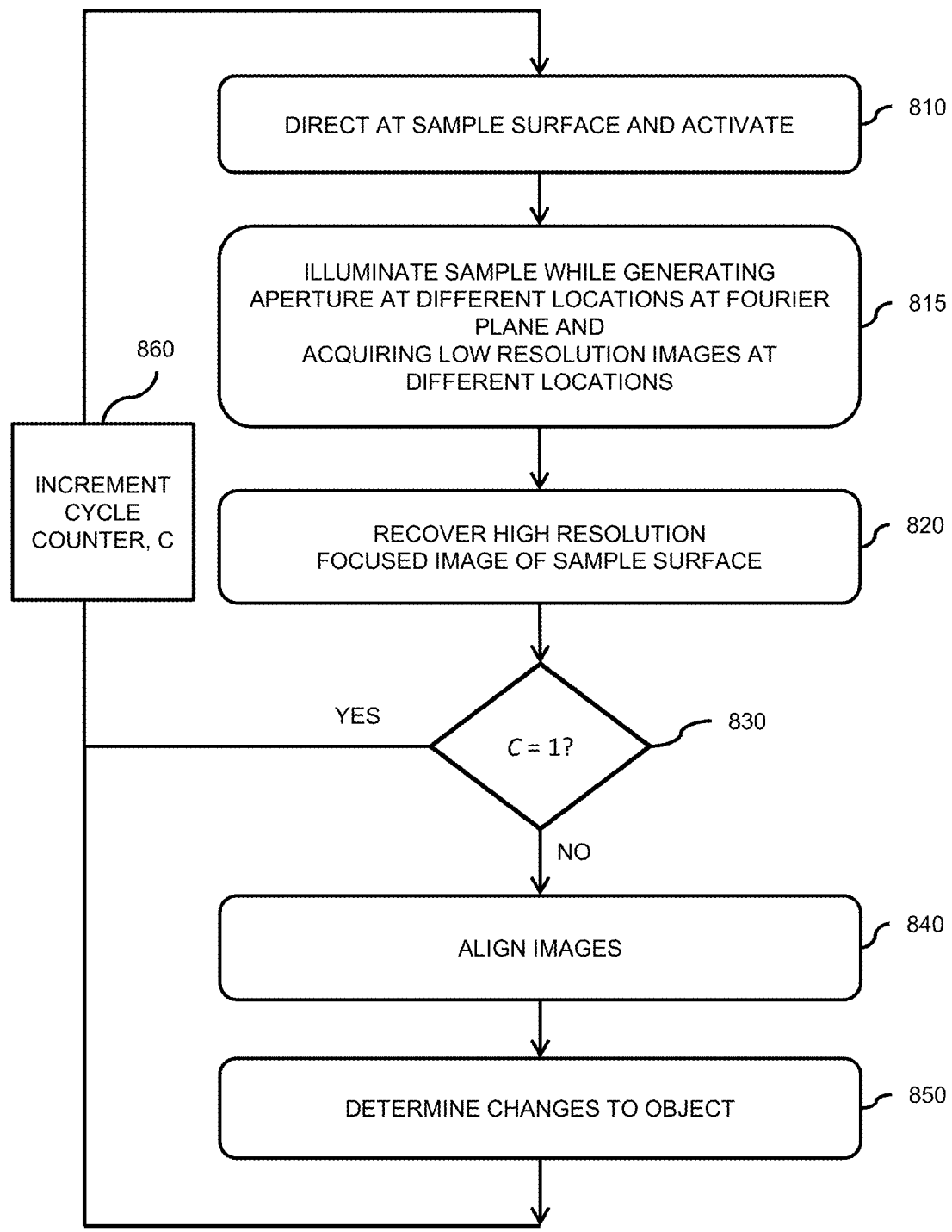
FIG. 9 is a flowchart of a Fourier camera method performed by a Fourier camera system, according to embodiments.

FIG. 9 is a flowchart of a Fourier camera method performed by a Fourier camera system, according to embodiments. The Fourier camera method generally comprises an acquisition process (steps 810 and 815), a recovery process (step 820), and a screening process (steps 830, 840, and 850, and 860). Although not shown, the Fourier camera method may optionally comprise a display process.

At step 810, a Fourier camera system is pointed at the sample surface with the object of interest being imaged and the camera is activated to start an acquisition process of an imaging cycle. For example, an operator may point the Fourier camera system at the sample surface having an object of interest and activate the system to start the acquisition process by, for example, touching/pressing a button, switch, or other activation device. At the first imaging cycle used to image the sample surface, the cycle counter, C, is set to 1.

Once activated, the Fourier camera system starts the acquisition process to acquire M raw intensity images of the sample surface (step 815). At step 815, the Fourier camera system uses its illumination source(s) to provide an illuminate beam to the sample surface and the light detector captures a sequence of images of the sample surface while the SLM shifts an aperture to different locations across its display in an overlapping sequence. In one example, the illumination beam is similar to a conventional camera flash. In some cases, the SLM may be digitally addressed to rapidly shift a liquid-crystal based pupil function, which selectively blocks different areas of the light field entering into the camera's pupil plane depending upon which SLM display pixels are electronically triggered. The overlapping sequence has overlapping regions between certain neighboring apertures. An example of an overlapping region 334 on an SLM display 333 and an overlapping sequence of N aperture locations is shown in FIG. 4. At each sample time, the light detector acquires an intensity distribution of a raw image associated with a particular aperture location. During the acquisition process, the light detector acquires M raw intensity images of the sample surface associated with different aperture locations.

At step 820, the Fourier camera system recovers a focused, high resolution image of the sample surface using the raw images acquired during the acquisition process. The image may be a uniform resolution two-dimensional image or a three dimensional profile image. At step 820, generally, each of the M intensity images is divided into tiles, the M intensity tile images are iteratively stitched together in overlapping regions in Fourier space to recover a complex and higher resolution image of the tile, each complex tile image is propagated to a best focal plane, and the focused and higher resolution tile images are combined to generate a focused image of the sample surface. In some cases, the best focal plane for each tile is determined by propagating each complex tile image to multiple focal planes and determining which of the focal planes is the best focal plane. During the recovery process, each tile may be focused so that an entire curved sample surface can be uniformly focused to have a uniform resolution. Details of this step 820 are described with reference to FIG. 10.

At step 830, the Fourier camera system determines whether the cycle counter, C, =1 (i.e. first cycle). If C=1, the Fourier camera system increments the cycle counter, C, for the next cycle at step 860 and returns to step 810. If C does not equal 1, the Fourier camera system aligns images acquired during multiple cycles at step 840. The Fourier camera system may align the images based on, for example, the determined curvature of the sample surface by surface matching process, higher resolution images by pattern matching. The curvature of the sample surface may be determined from the distances between the Fourier camera system and the sample surface (depths) determined at step 820. In some cases, the Fourier camera system may align the images to within 5% of each other for different orientations. In other cases, the Fourier camera system may align the images to within 10% of each other for different orientations. In other cases, the Fourier camera system may align the images to within 1% of each other for different orientations.

At step 850, the Fourier camera system compares the aligned images to determine changes in one or more objects on the sample surface. For example, the Fourier camera system may outline the one or more objects on the sample surface (i.e. determine the boundary(s)) in sequential cycles to determine the growth of the one or more objects between sequential cycles. The outlines determined at different imaging cycles can be used to determine areas of the objects and/or percentage change in an areas of the objects between cycles. These determinations may be used as a measurement of growth of the objects. As another example, the Fourier camera system may determine a shade/color of the one or more objects to determine changes of the shades/colors between cycles. At step 860, the cycle counter, C, is incremented for the next cycle time at step 810.

Figure 10:
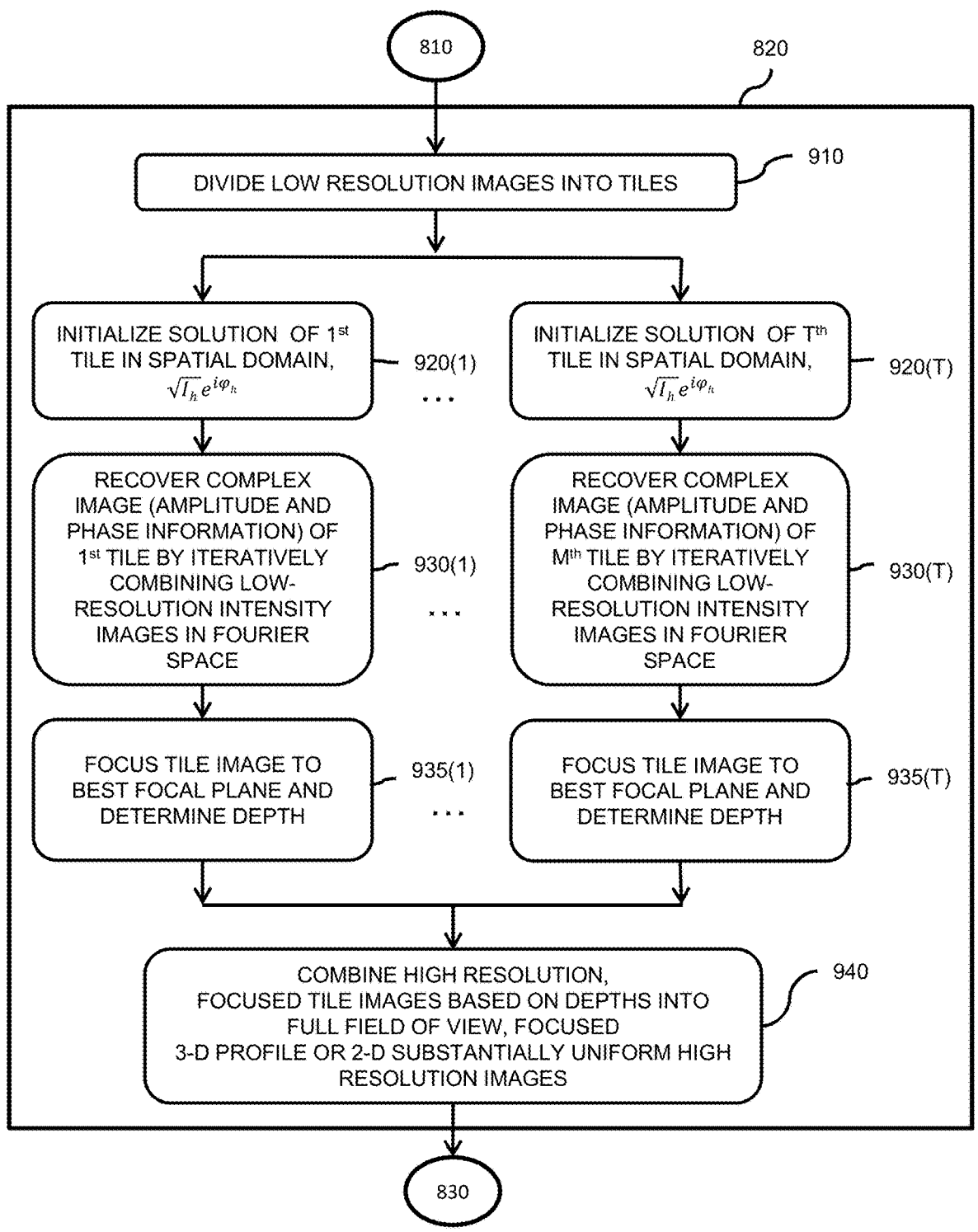
FIG. 10 is a flowchart of details of one of the steps of FIG. 9, according to embodiments.

FIG. 10 is a flowchart of sub-steps of step 820 of FIG. 9. An example of a recovery process of the Fourier camera method is described with respect to FIG. 10. Generally, during this exemplary recovery process, intensity images captured during the acquisition cycle are divided into a plurality of intensity tile images, a higher resolution, complex image of the tiles are independently determined, the tile images are propagated to the best focal plane, and the higher resolution focused tile images are combined to generate a full field-of-view higher resolution image.

At step 910, the Fourier camera system divides the full field-of-view into a plurality of T tiles. In one example, the plurality of tiles may be in the form of a two-dimensional matrix of tiles. In one case, the plurality of tiles may be a two-dimensional square matrix of tiles with dimensions of, for example, 256×256, 64×64, or the like. In another case, the plurality of tiles may be a two-dimensional rectangular matrix with dimensions of, for example, 5,280×4,380. Each tile may correlate to a set of one or more discrete light detecting elements (e.g., pixels) of the light detector.

Steps 920(1) to 920(T), 930(1) to 930(T), and 935(1) to 935(T) are computations made for the $1^{st}$ to the $T^{th}$ tile. In some cases, each of the parallel steps for each tile (e.g., step 920(1), step 930(1), step 935(1) for $1^{st}$ tile, step 920(2), step 930(2), step 935(2) for $2^{nd}$ tile, ... step 920(T), step 930(T), step 935(T) for $T^{th}$ tile) may be acquired independently and/or in parallel. In some of these cases, parallel computing may be used, which may reduce computation time and/or memory requirements. To take advantage of parallel processing capabilities, the Fourier camera system may comprise a processor with parallel processing capabilities such as, for example, the GPU unit or a processor having multiple cores (i.e. independent central processing units).

At each of steps 920(1) . . . 920(T), the Fourier camera system initializes a higher resolution image solution, $\sqrt{I_h}e^{i\varphi_h}$, for each tile respectively in the spatial domain and a Fourier transform is applied to the initial solution of each tile to generate a Fourier transform of the higher-resolution image denoted as $\tilde{I}_h$. T is the number of tiles used. In some cases, the initial solution may be a random complex two dimensional matrix of values for both intensity and phase. In other cases, the initial solution may be an interpolation of the intensity measurement with a random phase. An example of an initial solution may be φ=0 and the intensity image matrix of the tile area. Another example of an initial solution may be a constant value. In one example, the Fourier transform of the initial solution may be a broad spectrum in the Fourier domain.

At step 930(1) . . . step 930(M), the Fourier camera system recovers a complex (amplitude and phase information) image of each tile respectively by iteratively combining raw intensity images in Fourier space. Details of step 930(1) . . . step 2501(M) are described with reference to FIG. 11.

At step 935(1) . . . step 935(M), the Fourier camera system focuses each tile to the best focal plane and determines the distance of that best focal plane to the Fourier camera system. The Fourier camera system may determine the best focal plane by propagating the complex tile image to multiple planes and determining which of the propagated images has the highest contrast. Once the best focal plane is determined, the Fourier camera system can determine the distance between the best focal plane and the focal plane of the Fourier camera system. In one embodiment, a Fourier camera system may measure the image contrast at each plane by using Root mean square (RMS) contrast in the following Eqn. 1:

$$\sqrt{\frac{1}{MN}\sum_{i=0}^{N-1}\sum_{j=0}^{M-1}(I_{ij}-\bar{I})^2}, \quad \text{(Eqn. 1)}$$

Where intensities $I_{ij}$ are the i-th and j-th element of the two dimensional image of size M by N, $\bar{I}$ is the average intensity of all pixel values in the image. With the measured RMS contrast at different planes, the Fourier camera system can determine the best focal plane (i.e. plane at which the image contrast is the highest).

At step 940, the Fourier camera system combines focused higher-resolution tile images at their determined depths to generate a field-of view higher-resolution 3-D profile image or a uniform resolution 2-D image of the entire sample surface. In some cases, combining the tile images comprise an imaging-blending process such as, for example, alpha blending. An example of an image blending process is alpha blending which can be found in PCT publication WO1999053469, entitled "A system and method for performing blending using an over sampled buffer," filed on Apr. 7, 1999, which is hereby incorporated by reference in its entirety for this example. After step 940, the Fourier camera system continues to step 830 of FIG. 9.

Figure 11:
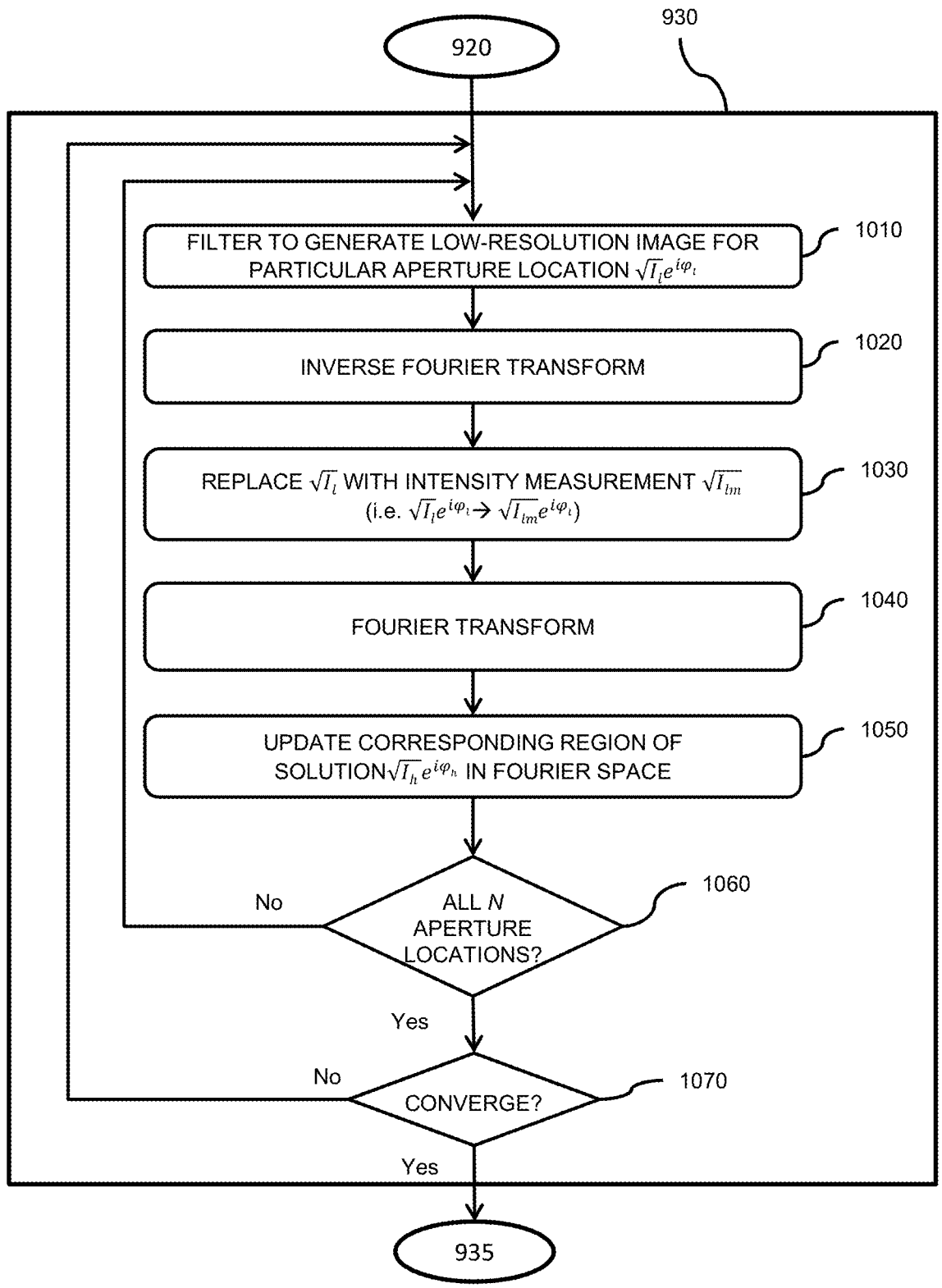
FIG. 11 is a flowchart of details of one of the steps of FIG. 10, according to embodiment.

FIG. 11 is a flowchart of sub-steps of step 930 of FIG. 10, according to embodiments. In step 930, the Fourier camera system recovers a complex image (amplitude and phase information) of each tile respectively by iteratively combining raw intensity images in Fourier space. In certain cases, recovering a complex image of each tile from a sequence of raw images may be accomplished using a phase retrieval technique. Using this phase retrieval technique, both amplitude and phase variations of light reflected from a sample surface can be determined. Once both amplitude and phase variations are determined, the Fourier camera method can use this information to propagate the light field wavefront forward or backwards to sharpen image focus, stitch together different overlapping images in the Fourier domain to enhance resolution, and/or measure the distance from the Fourier camera system to any point on the sample surface.

At step 1010, the Fourier camera system performs low-pass filtering of the high-resolution image $\sqrt{I_h}e^{i\varphi_h}$ in the Fourier domain to generate a low-resolution image $\sqrt{I_l}e^{i\varphi_l}$ for a particular aperture location. The Fourier transform of the high-resolution image is $\tilde{I}_h$ and the Fourier transform of the low-resolution image for a particular aperture location is $\tilde{I}_l$. In the Fourier domain, this phase retrieval technique filters a low-pass region from the spectrum $\tilde{I}_h$ of the high-resolution image $\sqrt{I_h}e^{i\varphi_h}$.

At step 1020, the Fourier camera system inverse Fourier transforms $\sqrt{I_l}e^{i\varphi_l}$ to generate low resolution image in spatial domain.

At step 1030, the Fourier camera system determines the amplitude component $\sqrt{I_l}$ of the low-resolution image, $\sqrt{I_l}e^{i\varphi_l}$, and replaces it with the square root of the low-resolution intensity measurement, $\sqrt{I_{lm}}$, as measured by the light detector while the variable aperture filter provides the aperture at the particular aperture location ($\sqrt{I_l}e^{i\varphi_l} \rightarrow \sqrt{I_{lm}}e^{i\varphi_l}$). This determination provides an updated low resolution target image: $\sqrt{I_{lm}}e^{i\varphi_l}$.

At step 1040, the Fourier camera system applies a Fourier transform to the updated target image.

At step 1050, the Fourier camera system updates the corresponding region of high-resolution solution $\sqrt{I_h}e^{i\varphi_h}$ in the Fourier space with the updated target image in the region in Fourier space corresponding to the aperture at the particular location as provided by the variable aperture filter (e.g., spatial light modulator).

The phase retrieval technique used by the Fourier camera system is an iterative process. In each round of iteration, the phase information of the sample's Fourier spectrum is corrected, using the intensity measurement in steps 1030-1050. Iteratively, the complex sample Fourier spectrum reconstructed is corrected and approaching the real sample Fourier spectrum. This phase retrieval technique uses raw intensity image information associated with different aperture locations at the intermediate (e.g., Fourier) plane to arrive at an amplitude and phase profile of the light field emerging from the sample surface.

At step 1060, the Fourier camera system determines whether steps 1010 to 1050 have been completed for all N aperture locations. If steps 1010 through 1050 have not been completed for all N aperture locations ("No" response), steps 1010 to 1050 are repeated for the at the next aperture location. If steps 1010 through 1050 have been completed for all N aperture locations ("Yes" response), the method returns to step 935 of FIG. 10.

In most embodiments, the neighboring regions in Fourier space, which are iteratively updated for each aperture location, overlap each other. In the overlapping area between updated overlapping regions, the Fourier camera method has multiple samplings over the same Fourier space. The aperture locations determine the area of the overlapping area. In one embodiment, the overlapping area between neighboring regions may have an area that is between about 2% to 99.5% of the area of one of the neighboring regions. In another embodiment, the overlapping area between neighboring regions may have an area that is between about 65% to 75% of the area of one of the neighboring regions. In another embodiment, the overlapping area between neighboring regions may have an area that is about 65% of the area of one of the neighboring regions. In another embodiment, the overlapping area between neighboring regions may have an area that is about 70% of the area of one of the neighboring regions. In certain embodiments, each overlapping region has the same area.

At step 1070, the Fourier camera system determines whether the high-resolution solution has converged. If the Fourier camera system determines that the high-solution has not converged ("No" response), then steps 1010 through 1060 are repeated in another iteration. If the solution has converged ("Yes" response), the Fourier camera system inverse Fourier transforms the converged solution to the spatial domain to recover a high-resolution image $\sqrt{I_h}e^{i\varphi_h}$ and the method returns to step 935 of FIG. 10. In some cases, the Fourier camera system may determine that the high-resolution solution has converged if it is determined that the current solution is a self-consistent solution. For example, the Fourier camera system may compare the high-resolution solution of the previous iteration to the current high-resolution solution, and if the difference is less than a certain value, the solution may have converged to a self-consistent solution.

Figure 12:
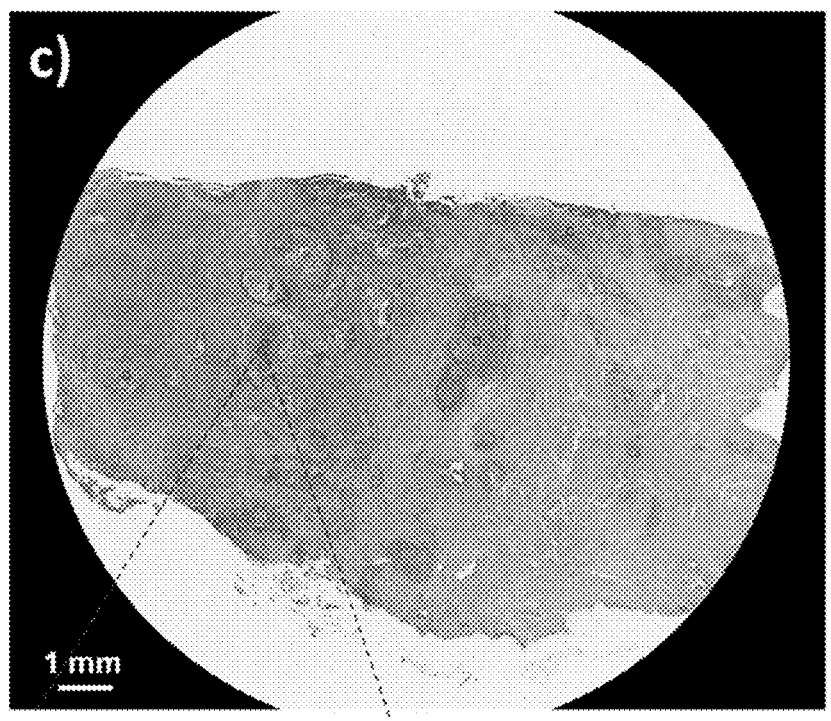
FIG. 12 is an image acquired by an FPM.
Figure 13:
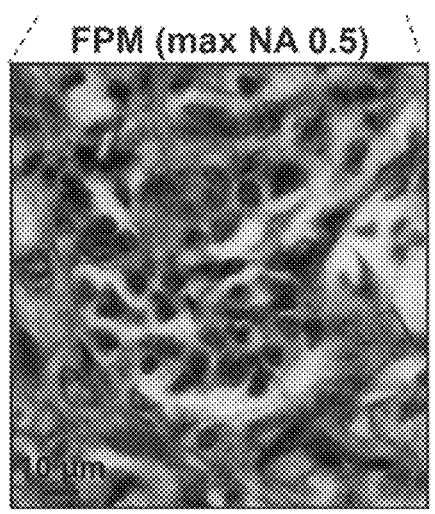
FIG. 13 is a zoomed in view of detail of the image of FIG. 12.
Figure 14:
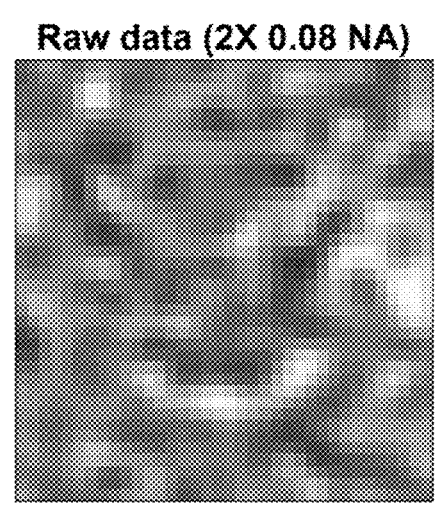
FIG. 14 is one of the lower resolution raw images captured by the objective lens of the FPM that is used to determine the high resolution image shown in FIG. 12.

A different phase retrieval technique that uses intensity images based on illuminating the sample by different illumination angles has been used in a Fourier Ptychographic Microscope (FPM). The FPM is a system that may enable a low-quality microscope to perform like an 'optically-perfect' microscope offering a large field-of-view, high-resolution and long depth-of-field. Certain details of this different phase retrieval technique can be found in U.S. patent application Ser. No. 14/448,850, titled "APERTURE SCANNING FOURIER PTYCHOGRAPHIC IMAGING," filed on Jul. 31, 2014, in Zheng, G., R. Horstmeyer, and C. Yang, "Wide-field, high-resolution Fourier ptychographic microscopy," Nature Photonics, vol. 7(9), pp. 739-745 (2013), in Ou, X., et al., "Quantitative phase imaging via Fourier ptychographic microscopy," Optics Letters, vol. 38(22): pp. 4845-4848 (2013), and in Horstmeyer, R. and C. Yang, "A phase space model of Fourier ptychographic microscopy," Optics Express, vol. 22(1), pp. 338-358 (2014), in Ou, X., G. Zheng, and C. Yang, "Embedded pupil function recovery for Fourier ptychographic microscopy," Optics Express, vol. 22(5), pp. 4960-4972 (2014), and in Bian, Z., S. Dong, and G. Zheng, "Adaptive system correction for robust Fourier ptychographic imaging," Optics express, 21(26), pp. 32400-32410 (2013), which are hereby incorporated by reference in its entirety for details regarding aberration correction. The FPM techniques can convert a low-quality microscope with poor resolution (~4 um), depth of field (~110 um) and an image pixel count of 56 megapixels, into a high performance microscope with a resolution of 0.78 um, a depth of field of 300 um and an image pixel count of 1 gigapixel. FIG. 12 is a large field-of-view, high-resolution and long depth-of-field image acquired by an FPM. FIG. 13 is a zoomed in view of detail of the image of FIG. 12. FIG. 14 is one of the plurality of raw lower resolution images captured by the objective lens of the FPM, wherein the plurality of raw lower resolution images is used to determine the high resolution image shown in FIG. 12. The raw lower resolution image in FIG. 14 is shown for comparison with higher resolution image in FIG. 12.

The phase retrieval technique used by the Fourier camera system is different from conventional phase retrieval methods in at least the following respects. First, the Fourier camera system uses reflective illumination. Second, the Fourier camera system uses angular diversity based on the shifting aperture at the intermediate plane which selectively transmits different angular components of the light field at the camera aperture. In addition, the Fourier camera system renders a topological profile of a curved sample surface.

Color imaging capability is pivotal for pathology and histology. In certain embodiments, a Fourier camera system may be configured for color imaging. For example, a Fourier camera system may comprise the illumination source configured to provide red, green, and blue illumination (e.g., red, green, and blue LEDs) at different sample times. This Fourier camera system can combine the images resulting from these illuminations to form a color image.

In certain hand-held device embodiments, a Fourier camera system comprises components of a point-and-shoot camera and a spatial light modulator in place of a conventional aperture stop. The SLM can be digitally addressed to quickly shift a liquid-crystal based pupil function, which selectively block lights depending upon which SLM pixels are electronically triggered. To use the Fourier camera system, and operator simply points the system at the sample surface and activates the system. The Fourier camera system first projects an illumination light beam on the sample surface (i.e., similar to a camera flash). Next, the Fourier camera system snaps a sequence of images of the skin while using the SLM to selectively block different areas of the light field entering into the camera's pupil plane. The complete image sequence thus contains M raw image frames, where M may equal the number N of total shifted SLM pupil functions (apertures displayed).

In one exemplary hand-held device embodiment, a Fourier camera system comprises components of a digital camera (e.g., Nikon® D3200 camera) while replacing the aperture stop with an SLM. In one case, the digital camera has a sensor pixel count of 24.2 million and the capability of acquiring images at a continuous frame rate of 4 frames per second. Optical elements are added to ensure the camera's aperture plane is accessible. The SLM (e.g., EPSON® HDTV LCD) is placed in that back focal plane. A trio of high intensity LED at red, green and blue wavelengths is used as a set of illumination sources. The sample surface was varied by +/−30 degrees rotation along x- and y-axis to test the robustness of the change in orientation relative to the Fourier camera system. The computing system having a processor (e.g., a GTX 780 GPU) was used to process the raw images. In one case, 81 raw images were acquired in the acquisition process. The SLM was configured to generate a 1.6 mm diameter transmissive circular pupil function that would be sequentially translated in step increments of 0.6 mm in a square grid pattern. This particular square grid pattern provides raw images acquired by the light detector that will subtend a spatial frequency range of $-0.06\pi/\lambda \sim 0.06\pi/\lambda$ in the Fourier domain, and the sequential pupil will overlap by 60%. The Fourier camera method described with respect to FIGS. 9, 10 and 11 were used to render amplitude and phase information of the target sample. In one example, the convergence criterion for halting the iterative process in FIG. 11 was when the image improvement changed to 1%. The full image was divided into 1600 tiles. Upon reaching a converged solution for each tile image, the tile image can be refocused to its sharpest acuity by propagating the computed complex field to its proper plane of focus (e.g. determined best focal plane). A focus index, measuring image sharpness, may be used to determine the best focal plane to refocus each tile. This method may be used to bring each tile of the final image into focus. In addition, the method can determine the distance between the best focal plane and the camera. With this distance and focused tile images, the method can render a final image in a 3-D topology. In this example, the Fourier camera system imaged a sample surface with a resolution of 100 um, an angular range of ~30°~30° and a distance-from-camera-to-target accuracy of 100 um over a distance range of 45 mm-55 mm.

One or more aspects of a Fourier camera methods and systems may provide one or more technical advantages. One advantage of an aspect is that a Fourier camera method/system may be able to refocus an image after initial images are acquired. That is, the Fourier camera method/system may digitally tune the image focus after the initial images are captured so that the Fourier camera system/method can bring all areas of a variably blurred image into sharp focus. This Fourier camera method/system can refocus the image to different planes without a reduction in resolution in the final image. Another advantage of an aspect is that a Fourier camera method/system may be able to provide substantially to entirely uniform high resolution across the entire image of a curved sample surface. Another advantage of an aspect is that a Fourier camera method/system may be able to automatically compute a focused topological profile of the image surface regardless of camera position or orientation. Another advantage of an aspect is that a Fourier camera method/system may be able to allow patients to track their own moles. The operational simplicity and cost-effective design of the Fourier camera method/system coupled with its ability to perform refocusing and image reorientation post-data acquisition, may make it practical for patients to image their own moles and provide these images (e.g., uploaded to a clinician's database) to a clinician for detailed inspection and mole tracking By keeping the metric of assessment as simply mole growth rate, the Fourier camera method/system can provide an objective quantification of the mole size over time that fully aligns with the primary hallmark of cancer—growth ('evolution'). One advantage of an aspect is that a Fourier camera method/system may be able to improve resolution between the raw images and the 3-D profile image to 100 microns or better. One advantage of an aspect is that a Fourier camera method/system may be able to acquire objective and high-resolution images of objects that are independent of camera position and orientation, which may allow for more accurate tracking of mole size and a direct assessment of a mole's abnormal development. One advantage of an aspect is that the Fourier camera method/system may be able to accurately measure mole size from the objective topological image at each cycle. First, with the 3-D profile, the method/system can account for any camera position change. Since we get 3-D profile of the sample, the change in position and orientation can be accounted for by aligning the images. The alignment process includes image magnification, movement and rotation, which can compensate for the position and orientation change of the camera between different capture imaging cycles. Second, the method/system does not require any pressure on the skin which rules out skin elasticity and muscle tone variations from our longitudinal size measurements. Another advantage of an aspect of the Fourier camera system is its simple operation and compact and cost-effective design.

III. Subsystems

Figure 15:
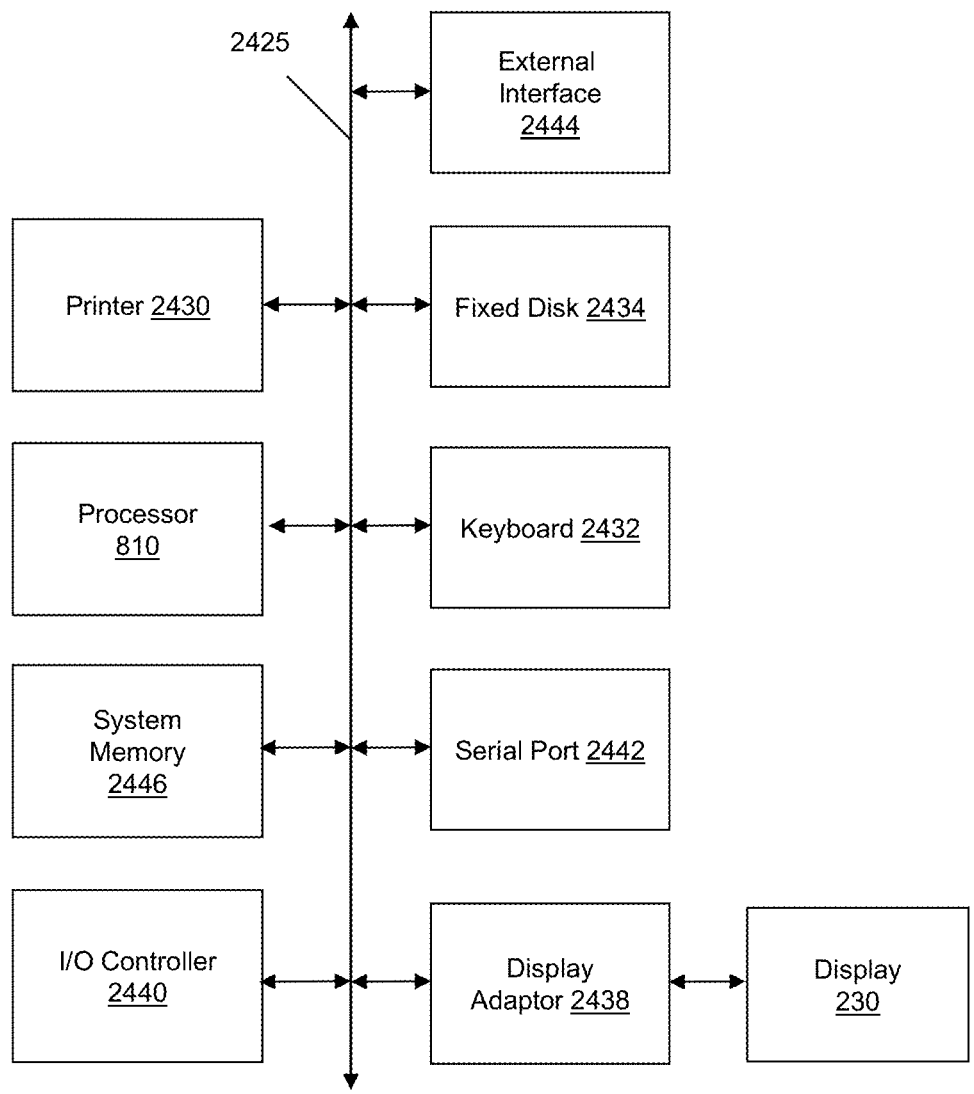
FIG. 15 is a block diagram of one or more subsystems that may be present in certain Fourier camera systems, according to embodiments.

FIG. 15 is a block diagram of one or more subsystems that may be present in certain Fourier camera systems, according to embodiments. For example, a Fourier camera system may include a processor. The processor may be a component of the Fourier camera system in some cases. The processor may be a component of the light detector in some cases.

The various components previously described in the Figures may operate using one or more of the subsystems to facilitate the functions described herein. Any of the components in the Figures may use any suitable number of subsystems to facilitate the functions described herein. Examples of such subsystems and/or components are shown in a FIG. 15. The subsystems shown in FIG. 15 are interconnected via a system bus 2425. Additional subsystems such as a printer 2430, keyboard 2432, fixed disk 2434 (or other memory comprising computer readable media), display 230, which is coupled to display adapter 2438, and others are shown. Peripherals and input/output (I/O) devices, which couple to I/O controller 2440, can be connected by any number of means known in the art, such as serial port 2442. For example, serial port 2442 or external interface 2444 can be used to connect components of a computing device to a wide area network such as the Internet, a mouse input device, or a scanner. The interconnection via system bus 2425 allows the processor to communicate with each subsystem and to control the execution of instructions from system memory 2446 or the fixed disk 2434, as well as the exchange of information between subsystems. The system memory 2446 and/or the fixed disk 2434 may embody the CRM 220 in some cases. Any of these elements may be present in the previously described features.

In some embodiments, an output device such as the printer 2430 or display 230 of the Fourier camera system can output various forms of data. For example, the Fourier camera system can output 2D color/monochromatic images (intensity and/or phase), data associated with these images, or other data associated with analyses performed by the Fourier camera system.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM, such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A Fourier camera comprising:
a first optical system configured to collect illumination reflected from a curved sample surface of a sample being imaged during operation;
a variable aperture filter comprising a plurality of elements, the variable aperture filter configured to cause one or more elements of the plurality of elements to generate at least one aperture at each of a plurality of aperture locations in a Fourier plane, wherein the at least one aperture is configured to receive and filter light reflected from the curved sample surface that is propagated by the first optical system;
a second optical system configured to collect light propagated by the at least one aperture at the Fourier plane; and
a light detector configured to receive light from the second optical system, and configured to acquire a plurality of raw intensity images of the curved sample surface, wherein each of the plurality of raw intensity images is based on light propagated by the at least one aperture at one of the plurality of aperture locations at the Fourier plane;
wherein data derived from the raw intensity images is updated in overlapping regions in Fourier space to generate data used to generate a focused, substantially uniform resolution image of the curved sample surface,
wherein data derived from the raw intensity images is updated in overlapping regions in Fourier space to recover phase information,
wherein the overlapping regions correspond to the plurality of aperture locations, and
wherein the Fourier plane is between the object plane and the image plane in the optical path.

2. The Fourier camera of claim 1, further comprising a processor in communication with the light detector to receive signals with the raw intensity images, the processor configured to:
divide each of the raw intensity images into a plurality of tile images;
for each tile image, update region in Fourier space with data associated with the raw intensity images for the tile image to generate data used to determine a complex tile image, and focus the complex tile image; and
combine the focused complex tile images to construct a focused, substantially uniform resolution image of the curved sample surface.

3. The Fourier camera of claim 2, wherein the processor is configured to focus the complex tile image by:
determining a best focal plane for each tile; and
determining a distance between the best focal plane of each tile and the first optical system for each tile.

4. The Fourier camera of claim 3,
wherein the focused, substantially uniform resolution image is a 3-D profile, and
wherein the processor is further configured to combine the focused complex tile images at the distances determined of the corresponding tiles to construct the 3-D profile.

5. The Fourier camera of claim 3, wherein the processor is configured to determine the best focal plane for each tile by:
propagating the complex tile image to multiple planes;
measuring an image contrast for each of the propagated complex tile images;
determining a highest contrast image for each of the propagated complex tile images; and
determining a best focal plane associated with the highest contrast image determined.

6. The Fourier camera of claim 2,
further comprising a computer readable medium in communication with the processor,
wherein one or more of the focused, substantially uniform resolution images of the curved sample surface are stored on the computer readable medium.

7. The Fourier camera of claim 1,
further comprising a processor in communication with the light detector to receive signals with the raw intensity images,
wherein the processor is configured to:
generate a plurality of focused, substantially uniform resolution images during a plurality of imaging cycles;
align the focused, substantially uniform resolution images at different imaging cycles to each other; and
compare the focused, substantially uniform resolution images at different imaging cycles to determine changes to an object at the curved sample surface between cycles.

8. The Fourier camera of claim 7, wherein the processor is further configured to determine a change in size of the object based on the comparison.

9. The Fourier camera of claim 1,
wherein the variable aperture filter is a spatial light modulator,
wherein the plurality of elements comprises a plurality of display elements, and
wherein the spatial light modulator is configured to generate the at least one aperture by activating one or more sets of display elements of the plurality of display elements.

10. The Fourier camera of claim 9, wherein the plurality of display elements comprise one or more transmissive display elements or one or more reflective display elements.

11. The Fourier camera of claim 1, further comprising one or more illumination sources configured to provide illumination to the curved sample surface.

12. The Fourier camera of claim 11, wherein the one or more illumination sources comprises at least one light emitting diode or a laser source.

13. The Fourier camera of claim 1, wherein the variable aperture filter is further configured to generate the at least one aperture at each of the plurality of aperture locations at each sample time of the light detector.

14. The Fourier camera of claim 1, wherein the at least one aperture overlaps at neighboring aperture locations of the plurality of apertures locations.

15. The Fourier camera of claim 14, wherein the at least one aperture overlaps at neighboring aperture locations in an overlapping area that is at least about 70% of an area of the at least one aperture.

16. The Fourier camera of claim 14, wherein the at least one aperture overlaps at neighboring aperture locations by between 20% and 90% of the area of at least one aperture.

17. The Fourier camera of claim 1, wherein the first optical system and the second optical system are in a 4f configuration.

18. The Fourier camera of claim 1, wherein each of the plurality of elements of the variable aperture filter is a micromirror.

19. The Fourier camera of claim 1, wherein the at least one aperture generated has the same area at two or more of the plurality of aperture locations.

20. A method of using a Fourier camera to capture one or more focused, substantially uniform resolution images of a curved sample surface of a sample being imaged, the Fourier camera comprising a first optical system, a second optical system, a variable aperture filter comprising a plurality of elements, and a light detector, the method comprising:
  (a) collecting, at the first optical system, illumination reflected from the curved sample surface of the sample being imaged during operation;
  (b) causing one or more elements of the plurality of elements of the variable aperture filter to generate at least one aperture at each of a plurality of aperture locations at a Fourier plane during each sample time, wherein the Fourier plane is between the object plane and the image plane in the optical path, wherein the at least one aperture receives and filters illumination reflected from the curved sample surface that is propagated by the first optical system;
  (c) collecting, using the second optical system, light propagated by the at least one aperture located at the Fourier plane;
  (d) acquiring a plurality of raw intensity images of the curved sample surface based on light received from the second optical system, wherein each of the raw intensity images is acquired while the at least one aperture is at one of the plurality of aperture locations at the Fourier plane; and
  (e) updating data derived from the raw intensity images in overlapping regions in Fourier space to generate a focused, substantially uniform resolution image of the curved sample surface, wherein the overlapping regions correspond to the plurality of aperture locations, wherein data derived from the raw intensity images is updated in overlapping regions in Fourier space to recover phase information.

21. The method of claim 20, wherein the variable aperture filter is a spatial light modulator.

22. The method of claim 20, further comprising:
  dividing each of the raw intensity images into a plurality of tile images;
  for each tile image, updating region in Fourier space with data associated with the raw intensity images for the tile image to generate data used to determine a complex tile image and focus the complex tile image; and
  combining the focused complex tile images to construct the focused, substantially uniform resolution image of the curved sample surface.

23. The method of claim 20, further comprising illuminating the curved sample surface.

24. The method of claim 20, wherein focusing the complex tile image comprises:
  determining a best focal plane for each tile; and
  determining a distance between the best focal plane for each tile and the first optical system for each tile.

25. The method of claim 24,
  wherein the focused, substantially uniform resolution image is a 3-D profile; and
  further comprising combining the focused complex tile images at the distances determined of the corresponding tiles to construct a 3-D profile.

26. The method of claim 9, determining the best focal plane for each tile comprises:
  propagating the complex tile image to multiple planes;
  measuring an image contrast for each of the propagated complex tile images;
  determining a highest contrast image for each of the propagated complex tile images; and
  determining a best focal plane associated with the highest contrast image determined.

27. The method of claim 20, wherein the focused, substantially uniform resolution image is a 3-D profile.

28. The method of claim 20, further comprising:
  repeating steps (a), (b), (c), (d), and (e) to determine a plurality of focused, substantially uniform resolution images;
  aligning two or more of the plurality of focused, substantially uniform resolution images of the curved sample surface; and
  comparing the aligned two or more images to determine one or more changes in an object at the curved sample surface.

29. The method of claim 28, wherein the one or more changes comprise a change in size of the object.

30. The method of claim 20, wherein updating overlapping regions in Fourier space with data derived from the raw intensity images comprises:
  generating an initial solution in Fourier space;
  inverse Fourier-transforming the initial solution to generate a low resolution image;
  replacing data derived from the low resolution image with data derived from one of the plurality of raw intensity images to provide updated data;
  Fourier-transforming the updated data; and
  updating an overlapping region in Fourier space with the updated data.

* * * * *